United States Patent [19]
Morgante et al.

[11] Patent Number: 5,955,276
[45] Date of Patent: Sep. 21, 1999

[54] COMPOUND MICROSATELLITE PRIMERS FOR THE DETECTION OF GENETIC POLYMORPHISMS

[75] Inventors: Michele Morgante, Udine, Italy; Julie Marie Vogel, Malvern, Pa.

[73] Assignee: E.I. du Pont de Nemours and Company, Wilmington, Del.

[21] Appl. No.: 08/849,021

[22] PCT Filed: Jul. 3, 1997

[86] PCT No.: PCT/US95/15150

§ 371 Date: May 27, 1997

§ 102(e) Date: May 27, 1997

[87] PCT Pub. No.: WO96/17082

PCT Pub. Date: Jun. 6, 1996

Related U.S. Application Data

[63] Continuation-in-part of application No. 08/346,456, Nov. 28, 1994, abandoned.

[51] Int. Cl.⁶ ............................. C12Q 1/68; C12P 19/34
[52] U.S. Cl. ............................................... 435/6; 435/91.2
[58] Field of Search .............................. 435/6, 91.2, 91.1

[56] References Cited

U.S. PATENT DOCUMENTS

| | | | |
|---|---|---|---|
| 5,126,239 | 6/1992 | Livak et al. | 435/6 |
| 5,206,137 | 4/1993 | Ip et al. | 435/6 |

FOREIGN PATENT DOCUMENTS

| | | |
|---|---|---|
| WO 92/13968 | 8/1992 | European Pat. Off. |
| WO 92/13969 | 8/1992 | European Pat. Off. |
| 0534858 | 3/1993 | European Pat. Off. |
| 0552545 | 7/1993 | European Pat. Off. |
| 3834636 | 4/1990 | Germany. |
| 2 221 909 | 2/1990 | United Kingdom. |

OTHER PUBLICATIONS

Senior et al Genomics 36:884–889, 1993.
Grist et al Biotechniques 15:304–309, 1993.
Moore, S.S., et al., Genomics, 10, 654–660 (1991).
Epplen, J.T., The Journal Of Heredity, 79(6), 409–417 (1988).
Weber, J.L., et al., Genomics, 11, 695–700 (1991).
Wu, K. et al., Mol. Gen. Genet., 241, 225–235 (1993).
Weber, J.L., In Tilgman, S., Daves, K. (Eds.), Genome Analysis Vol. 1: Genetic and Physical Mapping, Cold Spring Harbor Labratory Press, 159–181 (1990).
Hing, A.V. et al., Am. J. Hum. Genet., 55, 509–517 (1993).
Beckmann, J.S. et al., Bio/Technology, 8, 930–932 (1990).
Litt, M. et al., Am. J. Hum. Genet., 44, 397–401 (1989).
Ellegren, H. et al., Animal Genetics, 23, 133–142 (1992).
Weber, J.L. et al., Am. J. Hum. Genet., 44, 388–396 (1989).
Slettan, A. et al., Animal Genetics, 24, 195–197 (1993).
Condit, R. et al., Genome, 34, 66–71 (1991).
Browne, D.L. et al., Nucleic Acids Research, 20(1) (1991).
Beckmann, J.S. et al., Genomics, 12, 627–631 (1992).
Botstein, D. et al., Am. J. Hum. Genet., 32, 314–331 (1980).
Buchanan, F.C. et al., Mammalian Genome, 4, 258–264 (1993).
Weber, J.L., Genomics, 7, 524–530 (1990).
Zietkiewicz, E. et al., Genomics, 20, 001–007 (1994).
Wu, K., et al., Nucleic Acids Research, 22(15), 3257–3258 (1994).
Morgante, M. et al., The Plant Journal, 3(1), 175–182 (1993).
Akkaya, M.S. et al., "Length Polymorphisms Of Simple Sequence Repeat DNA In Soybean", Soybean And Alfalfa Res. Lab., US Dept. Of Ag. Res. Service, Beltsville Ag Res. Ctr., Beltsville, MD 20705–2350 (1992).
Southern, E.M., J. Mol. Biol., 98, 503–517 (1975).
Williams, J.G.K. et al., Nucleic Acids Res., 18(22), 6531–6535 (1990).
Zietkiewicz et al., "Genomic Fingerprinting By SSR Anchored Polymerase Chain Reaction" Genomics 20: 176–183, 1994.
Buchanan et al., "Microsatellites And Associated Repetitive Elements In The Sheep Genome" Mammalian Genome 4:258–264, 1993.
Weber, "Human DNA Polymorphisms Based On Length Variations In Simple–Sequence Tandem Repeats" In Genome Analysis vol. 1: Genetic And Physical Mapping, pp. 159–181, 1990, CSHP.

*Primary Examiner*—Eggerton A. Campbell

[57] ABSTRACT

Compound microsatellites used as self-anchoring primers for screening genomes to detect polymorphisms are provided. The preferred compound microsatellite primers are perfect compound dinucleotide primers wherein the adjacent dinucleotide pairs contain a common nucleotide which is in-phase across the compound junction. In a useful embodiment, these in-phase compound primers have been adapted to other known screening assays including variations of the AFLP assays.

24 Claims, 22 Drawing Sheets

FIG. 1b

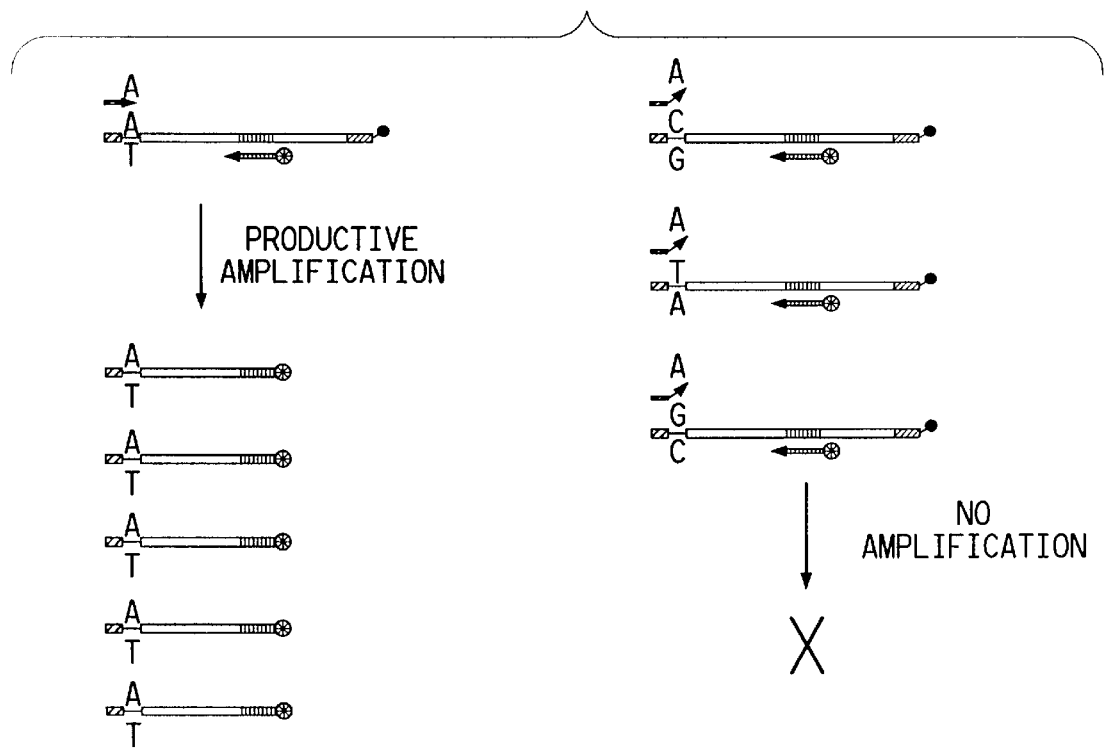

FIG. 1c

IN-PHASE PERFECT COMPOUND SSR LOCUS: $(AT)_{11.5}(GT)_{10}$

PRIMER:
$(AT)_{2.5}(GT)_{6.5}$           TATATATGTGTGTGTGTGTG →
$(AT)_{6.5}(GT)_{4.5}$         TATATATATATATGTGTGTGTG →
$(AT)_{8.5}(GT)_{3.5}$       TATATATATATATATATGTGTG →
    5'..NNTATATATATATATATATATATATATGTGTGTGTGTGTGTGTGTNN..3'
    3'..NNTATATATATATATATATATATATATCACACACACACACACACANN..5'
$(CA)_{4.5}(TA)_{7.5}$   ← TATATATATATATATACACACACA
$(CA)_{6.5}(TA)_{4.5}$    ← TATATATACACACACACACA
$(CA)_{4.5}(TA)_{7.5}$     ← TATATACACACACACACACA

| REC FRAC. | DIST cM | MARKER ID | NAME |
|---|---|---|---|
| | | (159) | 6011 |
| (6.9%) | 7.4 | (160) | 3807 |
| (7.3%) | 7.9 | (161) | 1029.00 |
| (8.0%) | 8.8 | (162) | 4510 |
| (19.5%) | 24.7 | (163) | 1201.00 |
| (13.3%) | 15.5 | (164) | 618.00 |
| (20.2%) | 25.9 | (165) | 6903.10 |
| (7.8%) | 8.5 | (166) | 1510.00 |
| (5.7%) | 6.0 | (167) | 4501.2 |
| (7.5%) | 8.1 | (323) | 94-23.p7 |
| (7.7%) | 8.4 | (168) | OLEO |
| (2.4%) | 2.4 | (169) | 1148.10 |
| (8.3%) | 9.1 | (170) | 3415 |
| (8.3%) | 9.0 | (171) | 6411.20 |
| (5.4%) | 5.7 | (172) | 7320.00 |
| (3.0%) | 3.0 | (173) | 1351.00 |
| (4.9%) | 5.1 | (174) | 2311 |

| REC FRAC. | DIST cM | MARKER ID | NAME |
|---|---|---|---|
| (2.3%) | 2.4 | (175) | 2611.00a |
| (3.1%) | 3.2 | (176) | 718.00 |
| (5.8%) | 6.1 | (177) | 506.00 |
| (5.3%) | 5.6 | (178) | 169.10 |
|  |  | (179) | 1233.00 |
| (10.0%) | 11.1 |  |  |
|  |  | (180) | 3217.00 |
| (9.2%) | 10.1 |  |  |
|  |  | (181) | 1080.00 |
| (7.3%) | 7.9 |  |  |
| (6.5%) | 6.9 | (182) | 6006.00 |
|  |  | (183) | 6501.00 |
| (11.7%) | 13.4 |  |  |
| (2.2%) | 2.3 | (184) | 5719.00 |
| (6.9%) | 7.4 | (185) | 5220.00 |
| (1.6%) | 1.6 | (186) | 1461.00 |
|  |  | (187) | 452.00 |
| (11.4%) | 12.9 |  |  |
|  |  | (188) | 4404.00 |
| (3.0%) | 3.1 | (326) | 94-23.p10 • |
| (7.1%) | 7.6 | (189) | 1503.00 |
| (12.8%) | 14.8 |  |  |
|  |  | (307) | 94-23.p5 • |
| (3.8%) | 4.0 | (190) | 1434.00 |
| (7.9%) | 8.6 |  |  |
|  |  | (191) | 3524.00 |
| (17.7%) | 21.9 |  |  |
|  |  | (192) | 5703.00 |

LG11

COMPOUND MICROSATELLITE PRIMERS FOR THE DETECTION OF GENETIC POLYMORPHISMS

This application is a 371 of PCT/US95/15150, filed on Nov. 21, 1995; which is a CIP of Application No. 08/346, 456, filed on Nov. 28, 1994, abandoned.

FIELD OF INVENTION

The present invention relates the use of perfect, compound simple sequence repeats (SSR) as self-anchoring primers for the identification and analysis of DNA sequence polymorphisms. More specifically it has been observed that any one type of simple sequence repeat (SSR) in both plant and animal genomes often exists directly adjacent to an SSR of a different type, usually with perfect periodicity of one of the component nucleotides shared by both SSRs. This observation has allowed the design of self-anchoring 15 primers in new variations of polymerase chain reaction-based multiplexed genome assays, including inter-repeat amplification and amplified fragment length polymorphism assays. These method variations collectively have been termed selective amplification of microsatellite polymorphic loci (SAMPL).

BACKGROUND

The ability to map eukaryotic genomes has become an essential tool for the diagnosis of genetic diseases, and for plant breeding and forensic medicine. An absolute requirement for elucidation of any genetic linkage map is the ability to identify DNA sequence variation. The realization that genetic (DNA) polymorphisms between phenotypically identical individuals are present and can be used as markers for genetic mapping has produced major advances in the art of developing eukaryotic linkage maps.

Techniques for identifying genetic polymorphisms are relatively few and to date have been time consuming and labor intensive. One of the most common techniques is referred to as restriction fragment length. polymorphism or RFLP (Botstein et al. *Am. J. Hum. Genet.* 342, 314, (1980)). Using RFLP technology, genetic markers based on single or multiple point mutations in the genome may be detected by differentiating DNA banding patterns from restriction enzyme analysis. As restriction enzymes cut DNA at specific target site sequences, a point mutation within this site may result in the loss or gain of a recognition site, giving rise in that genomic region to restriction fragments of different length. Mutations caused by the insertion, deletion or inversion of DNA stretches will also lead to a length variation of DNA restriction fragments. Genomic restriction fragments of different lengths between genotypes can be detected with region-specific probes on Southern blots (Southern, E. M.,*J. Mol. Biol.* 98, 503, (1975). The genomic DNA is typically digested with nearly any restriction enzyme of choice. The resulting fragments are electrophoretically size-separated, transferred to a membrane, and then hybridized against a suitably labelled probe for detection of fragments corresponding to a specific region of the genome. RFLP genetic markers are particularly useful in detecting genetic variation in phenotypically silent mutations and serve as highly accurate diagnostic tools. RFLP analysis is a useful tool in the generation of codominant genetic markers but suffers from the need to separate restriction fragments electrophoretically and often requires a great deal of optimization to achieve useful background to signal ratios where significant polymorphic markers can be detected. In addition, the RFLP method relies on DNA polymorphisms existing within actual restriction sites. Any other point mutations in the genome usually go undetected. This is a particularly difficult problem when assaying genomes with inherently low levels of DNA polymorphism. Thus, RFLP differences often are difficult to identify.

Another method of identifying polymorphic genetic markers employs DNA amplification using short primers of arbitrary sequence. These primers have been termed 'random amplified polymorphic DNA', or "RAPD" primers, Williams et al., *Nucl. Acids. Res.*, 18, 6531 (1990) and U.S. Pat. Nos. 5,126,239; (also EP0 543 484 A2, WO 92/07095, WO 92/07948, WO 92/14844, and WO 92/03567). The RAPD method amplifies either double or single stranded nontargeted, arbitrary DNA sequences using standard amplification buffers, dATP, dCTP, dGTP and TTP nucleotides, and a thermostable DNA polymerase such as Taq polymerase. The nucleotide sequence of the primers is typically about 9 to 13 bases in length, between 50 and 80% G+C in composition and contains no palindromic sequences. Differences as small as single nucleotides between genomes can affect the RAPD primer's binding/target site, and a PCR product may be generated from one genome but not from another. RAPD detection of genetic polymorphisms represents an advance over RFLP in that it is less time consuming, more informative, and readily adaptable to automation. The use of the RAPD assay is limited, however, in that only dominant polymorphisms can be detected; this method does not offer the ability to examine simultaneously all the alleles at a locus in a population. Nevertheless, because of its sensitivity for the detection of polymorphisms, RAPD analysis and variations based on RAPD/PCR methods have become the methods of choice for analyzing genetic variation within species or closely related genera, both in the animal and plant kingdoms.

A third method more recently introduced for identifying and mapping genetic polymorphisms is termed amplified fragment length polymorphism or AFLP (M. Zabeau, EP 534,858). AFLP is similar in concept to RFLP in that restriction enzymes are used to specifically digest the genomic DNA to be analyzed. The primary difference between these two methods is that the amplified restriction fragments produced in AFLP are modified by the addition of specific, known adaptor sequences which serve as the target sites for PCR amplification with adaptor-directed primers. Briefly, restriction fragments are generated from genomic DNA by complete digestion with a single or double restriction enzyme combination, the latter using a "frequent" cutter combined with a "rare" cutter. Optimal results are obtained when one of these enzymes has a tetranucleotide recognition site, and the other enzyme a hexanucleotide site. Such a double enzyme digestion generates a mixture of single- and double-digested genomic DNA fragments. Next, double-stranded adaptors composed of synthetic oligonucleotides of moderate length (10–30 bases) are specifically ligated to the ends of the restriction fragments. The individual adaptors corresponding to the different restriction sites all carry distinct DNA sequences.

One of the adaptors, usually the one corresponding to the hexanucleotide-site restriction enzyme, carries a biotin moiety. The application of biotin-streptavidin capture methodology leads to the selective removal of all nonbiotinylated restriction fragments (those bordered at both ends by the tetranucleotide restriction site), and thus effectively enriches the population for fragments carrying the biotinylated adaptor at one or both ends. As a result, the DNA fragment mixture is also enriched for asymmetric fragments, those carrying a different restriction site at each end. The selected fragments serve as templates for PCR amplification using oligonucleotide primers that correspond to the adaptor/restriction site sequences. These adaptor-directed primers also can include at their 3' ends from 1 to 10 arbitrary nucleotides, which will anneal to and prime from the genomic sequence directly adjacent to the restriction site on the DNA fragment.

A PCR reaction using this type of pooled fragment template and adaptor-directed primers results in the co-amplification of multiple genomic fragments. Any DNA sequence differences between genomes in the region of the restriction sites or the 1–10 nucleotides directly adjacent to the restriction sites leads to differences, or polymorphisms (dominant and codominant), in the PCR products generated. Multiple fragments are simultaneously co-amplified, and some proportion of these will be polymorphic between genomes.

A fourth method of assaying polymorphisms has involved utilizing the high degree of length variation resulting from certain repeating nucleotide sequences found in most genomes. Most if not all eukaryotic genomes are populated with repeating base sequences variously termed simple sequence repeats (SSR), simple sequence length polymorphisms (SSLP), dinucleotide, trinucleotide, tetranucleotide, or pentanucleotide repeats, and microsatellites. Simple sequence repeats have been demonstrated to be useful as genetic markers (DE 38 34 636 A, Jackle et al.; Weber, et al, *Am J Hum Genet* 44, 388, (1989); Litt et al., *Am J Hum Genet* 4, 397, (1989)). Weber et al., (*Genomics* 11, 695, (1991)) have successfully used SSRs for comparative analysis and mapping of mammalian genomes, and several groups (Akkaya, et al., *Genetics* 132, 1131 (1992), Morgante & Olivieri, *Plant J* 3, 175 (1993), Wu & Tanksley, *Mol. Gen. Genet.* 241, 225, (1993)) have demonstrated similar results with plant genomes. SSR polymorphisms can be detected by PCR using minute amounts of genomic DNA and, unlike RAPDs, they provide codominant markers and can detect a high degree of genetic polymorphism (Weber, J. L. (1990) In Tilghman, S., Daves, K., (eds) 'Genome Analysis vol. 1: Genetic and physical mapping', Cold Spring Harbor Laboratory Press, pp 159–181.).

Although SSR-directed PCR primers are highly effective for detecting polymorphism, their use suffers from a variety of practical drawbacks. Typically, markers generated by these methods are obtained by first constructing a genomic library, screening the library with probes representing the core elements of a particular repeat sequence, purifying and sequencing the positive clones, and synthesizing the primers specific for the flanking sequences for each cloned SSR locus. Genomic DNA is then amplified to screen for polymorphisms, and mapping of the genome is then carried out. The entire process is time consuming, expensive and technically demanding, and as a result has been somewhat limited in its application.

At least one method has been developed as an attempt to circumvent these limitations and allow the use of polymorphic SSR markers more directly, with no a priori knowledge of particular SSR locus sequences. Zietkiewicz, et al., (Genomics, 20, 176, (1994)), for example, demonstrate that a single-primer PCR amplification can be used to detect length polymorphisms between adjacent $(CA)_n$ repeats in animal and plant genomes. The PCR primers used for this assay each contain a particular SSR sequence that is flanked immediately 5' or 3' by 2 to 4 nucleotides of known or arbitrary sequence; these anchor sequences anneal to the non-SSR genomic sequences that flank the SSR sequence in the genome and serve to "anchor" the primer to a single position at each matching SSR locus. Radiolabeled SSR-to-SSR amplification products, generated when adjacent SSR sequences are oppositely oriented and spaced closely enough in the genome, are analysed by gel electrophoresis followed by autoradiography. This approach eliminates the need for cloning and sequencing SSRs from the genome, and reveals an enriched polymorphic banding pattern relative to single-locus SSR. Zietkiewicz et al, attribute the enriched pattern to use of the arbitrary sequence anchor, which allows the SSR primer to anneal and prime from many SSR target loci simultaneously.

In a concept similar to Zetkiewicz, Wu et al., (Nucleic Acids Res. 22, 3257, (1994)) teach a method for the detection of polymorphisms where genomic DNA is amplified by asymmetric thermally cycled PCR using radiolabeled 5' anchored primers consisting of microsatellite repeats in the presence of RAPD primers of arbitrary sequence. The method of Wu et al. is useful for the generation of genetic markers that incorporate many features of microsatellite repeats. Wu et al. does not disclose the use of compound microsatellite repeate primers for amplification.

Simple sequence repeats may be classified in several ways. In categorizing and characterizing human $(CA)_n$ or $(GT)_n$ repeats, Weber, J. L. (Genome Analysis Vol. 1, 159, 1990, Cold Spring harbor Laboratory Press, NY) defines at least three types of $(CA)_n$ SSR: simple perfect SSR, simple imperfect SSR, and compound SSR. Each perfect SSR is considered to be a simple $(CA)_n$ tandem sequence, with no interruptions within the repeat. Imperfect SSR are defined as those repeating sequences with one or more interruptions of up to 3 nonrepeat bases within the run of the repeat. Compound SSR are defined as those sequences with a CA or GT repeat stretch adjacent to or within 3 nucleotides of a block of short tandem repeats of a different sequence. Weber notes that perfect sequence repeats in humans comprise about 65% of the total $(dC-dA)_n(dG-dT)_n$ sequences cloned from the genome, imperfect repeats about 25%, and compound repeats about 10%. Weber theorizes that because perfect repeats contain the longest uninterrupted repeat blocks, they appear to provide the most useful information. Weber also teaches that repeats composed of 12 or more uninterrupted units are consistently more polymorphic than are shorter repeat stretches. Because imperfect repeats generally contain shorter repeat stretches, they appear to be less useful as indicators of polymorphism. Compound repeats in general have not been well characterized, and their potential informativeness has not been clearly established.

Others have used the polymorphisms detectable within perfect, imperfect and compound SSR loci to build genetic linkage maps. Buchanan et al. (*Mammalian Genome*, 4, 258, (1993)) teach that there is little difference in the utility of the different SSR types in the ovine genome with respect to their absolute polymorphism levels; the perfect, imperfect and compound repeats although likely present in the genome at differing frequencies (perfect and imperfect simple SSR's are more frequent than compound) were found to have similar average Polymorphism Information Content (PIC) values as defined by Botstein et al. (*Am. J. Hum. Genet.*, 32, 314, (1980)). In a study of $(GT)_n$ SSR in the Atlantic salmon genome, Slettan et al. (*Animal Genetics*, 24, 195, (1993)) found both perfect and imperfect simple SSR but no compound repeats. In an examination of the equine genome, Ellegren et al. (*Amimal Genetics*, 23, 133, (1993)) identified the highest levels of polymorphism involving $(TG)_n$ and $(TC)_n$ repeats among horse genotypes using primers designed to amplify perfect or imperfect simple repeats; although two of eight cloned $(GT)_n$ repeats were identified to be compound in structure (one perfect, one imperfect), neither was characterized further. Condit & Hubbell (*Genome* 34, 66 (1991)), in characterizing large-insert clones carrying $(AC)_n$ and $(AG)_n$ repeats from tropical trees and maize, found that 10–20% of inserts carrying one type of repeat also carried the other, and that many $(AC)_n$ sites also had other two-base repeats adjacent or nearby. Finally, Browne et al. (*Nucl. Acids Res.*, 20, 141, (1991)), in an attempt to characterize $(CA)_n$ SSR sequences in the human genome by DNA sequencing with degenerate $(CA)_n$ primers, disclose that 88% of their $(CA)_n$ repeats carried AT base pairs at one or both ends of the CA repeat.

To date, the record in the literature would indicate that although it varies with each type of genome, the incidence of compound SSRs in a genome is lower than that of either perfect of imperfect simple SSR sequences. Nevertheless, the information content (PIC value) of compound SSR sequences has been shown to be generally high. In addition, the literature would indicate that the detection of genetic polymorphisms by way of specifically isolating compound SSR loci generally would have marginal success; the use of probes or primers designed to recognize and thus specifically isolate individual compound SSR loci would be less efficient for generating large numbers of new SSR markers as compared to the isolation of the more numerous simple SSR sequences. Applicants have, however, unexpectedly discovered that compound SSR's, particularly those containing $(AT)_n$ repeats are highly polymorphic in eukaryotic genomes, and that oligonucleotides designed to anneal specifically to a specific type of SSR, termed herein as a perfect in-phase compound SSR, are particularly useful in the generation and detection of polymorphisms between eukaryotic genomes. A "perfect" compound SSR is one in which two different repeating sequences, each of which could be composed of di-, tri-, tetra-, or penta-nucleotide units, are located very near each other, with no more than 3 intervening bases between the two repeat blocks. One category of perfect compound repeat is one in which the two constituent repeats are immediately adjacent to one another, with no intervening bases. Further, a perfect compound SSR can be classified to be "in-phase" if both of the component simple repeats share a common nucleotide whose spacing is conserved across the repeat junction and over the length of the two repeat blocks. For example, the in-phase perfect compound SSR, $(AT)_n(AG)_n$, maintains the adenosine base "in-phase" across both components of this perfect compound structure.

Applicants have discovered that in-phase perfect compound SSR sequences such as $(dC-dA)_n(dT-dA)_n$ are abundant in both animal and plant genomes. Although the frequency of occurrence of each type of perfect compound SSR sequence varies within, as well as between, species, those sequences that are in-phase are of sufficiently high frequency in all eukaryotic genomes examined, and appear to be both well dispersed and highly polymorphic. Based upon their observation that the junction spanned by such directly adjacent, in-phase perfect repeats is absolutely predictable, Applicants have developed methodology which utilizes synthetic oligonucleotides containing in-phase compound sequences as self-anchoring primers in new variations of polymerase chain reaction-based multiplexed genome assays, including inter-repeat amplification and amplified fragment length polymorphism assays. Applicants have found that the 5' end of the compound SSR primer serves as an extremely efficient anchor base for primer extension that occurs from the 3'-end repeat. This primer extension initiates from inside the compound SSR target sequence, such that any length variation between different alleles at a target SSR locus is detectable as a corresponding length bariation in the resulting amplification products. Because such use of perfect compound SSRs as amplification primers generates multiple products wherein a high proportion are polymorphic (as high as 80%), Applicants believe that the method of their invention greatly facilitates the simultaneous identification of multiple genomic polymorphisms, both codominant and dominant. Thus, the present method offers great advantage in identifying polymorphic markers linked to genetic traits of interest, and also offers an efficient and convenient generic technique for genome fingerprinting and whole-genome comparisons.

SUMMARY OF THE INVENTION

This invention provides an improved method of detecting polymorphisms between two individual nucleic acid samples comprising amplifying segments of nucleic acid from each sample using primer-directed amplification and comparing the amplified segments to detect differences, the improvement comprising wherein at least one of the primers used in said amplification consists of a perfect compound simple sequence repeat. In a preferred embodiment, the compound primer is in-phase.

In a most preferred embodiment the present invention provides a method for the detection of genetic polymorphisms using a combination of in-phase perfect compound SSR primers and synthetic adaptor-directed primers for PCR amplification from restriction enzyme digested genomic DNA templates to which fixed-sequence adaptors have been ligated.

The present methods are particularly useful in the areas of clinical genetic diagnostics, forensic medicine (where it is important to detect small polymorphic changes in nucleic acid composition), as well as in the areas of animal and plant breeding and gene mapping. As specific applications, these methods have great utility for genome fingerprinting, polymorphic marker identification (i.e., "marking" a phenotypic trait), and germplasm comparisons.

BRIEF DESCRIPTION OF THE FIGURES

FIGS. 1A–1C illustrates a schematic representation of SSR-to-adaptor amplification. Panel a depicts the restriction enzyme double digestion, adaptor ligation, and biotin-streptavidin selection process for generating the DNA template mixtures, as well as the selective nature of a specific SSR primer for exponential SSR-to-adaptor amplification from a complex template DNA mixture. Panel b depicts the selective nature of the adaptor-directed primer, in this case containing at its 3' end one nondegenerate selective nucleotide, for discriminating template fragments that otherwise would be amplified by a common SSR primer. Diagonally hatched boxes indicate the biotinylated adaptor corresponding to a restriction enzyme with a 6-bp recognition site, and dark boxes depict the nonbiotinylated adaptor corresponding to an enzyme with a 4-bp recognition site. The biotin moiety is indicated by a solid circle. The vertically striped box indicates either a simple SSR or a compound SSR of a particular type that matches the SSR primer used for the PCR amplification. Arrows depict PCR primers, with the arrowhead showing the direction of primer extension; solid/dark arrows indicate adaptor-directed PCR primers, and vertically striped-hatched arrows indicate primers corresponding to the SSR sequence depicted on the template fragments. Only the SSR-directed primer is tagged with either a fluorescent or radiolabel, as indicated by *.

Pancel C depicts a perfect, in-phase compound SSR as a double-stranded locus in the genome $((AT)_x(AG)_y$, here where x=11.5 and y=10), which can serve as a target site for two classes of primer, each representing one strand of the double-stranded target locus. Individual primers within each class can differ by the relative length of each constituent repeat. The two classes of primer initiate primer extension in opposite directions (small arrows). In every case, the primer anneals to a fixed site at the target, and primer extension initiates inside the SSR region. In each case, any length variation in the 3'-most repeat between genomes could be detected as a codominant polymorphism using SSR-to-adaptor amplification.

Figure 2A:
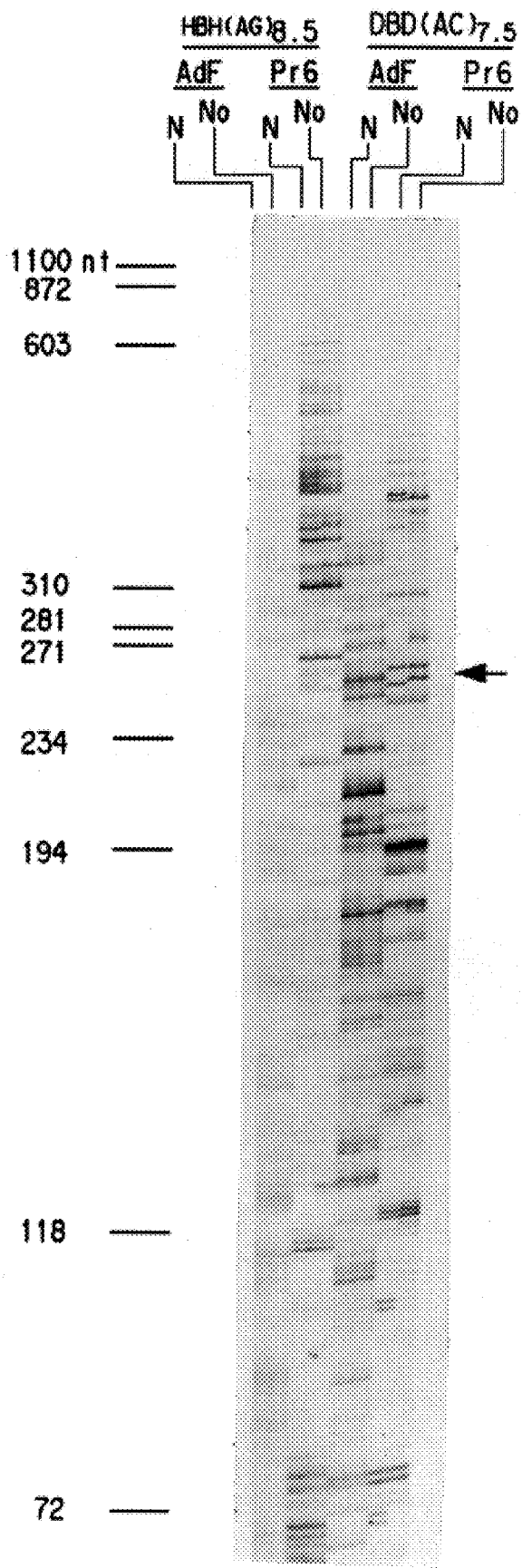
Figure 2B:
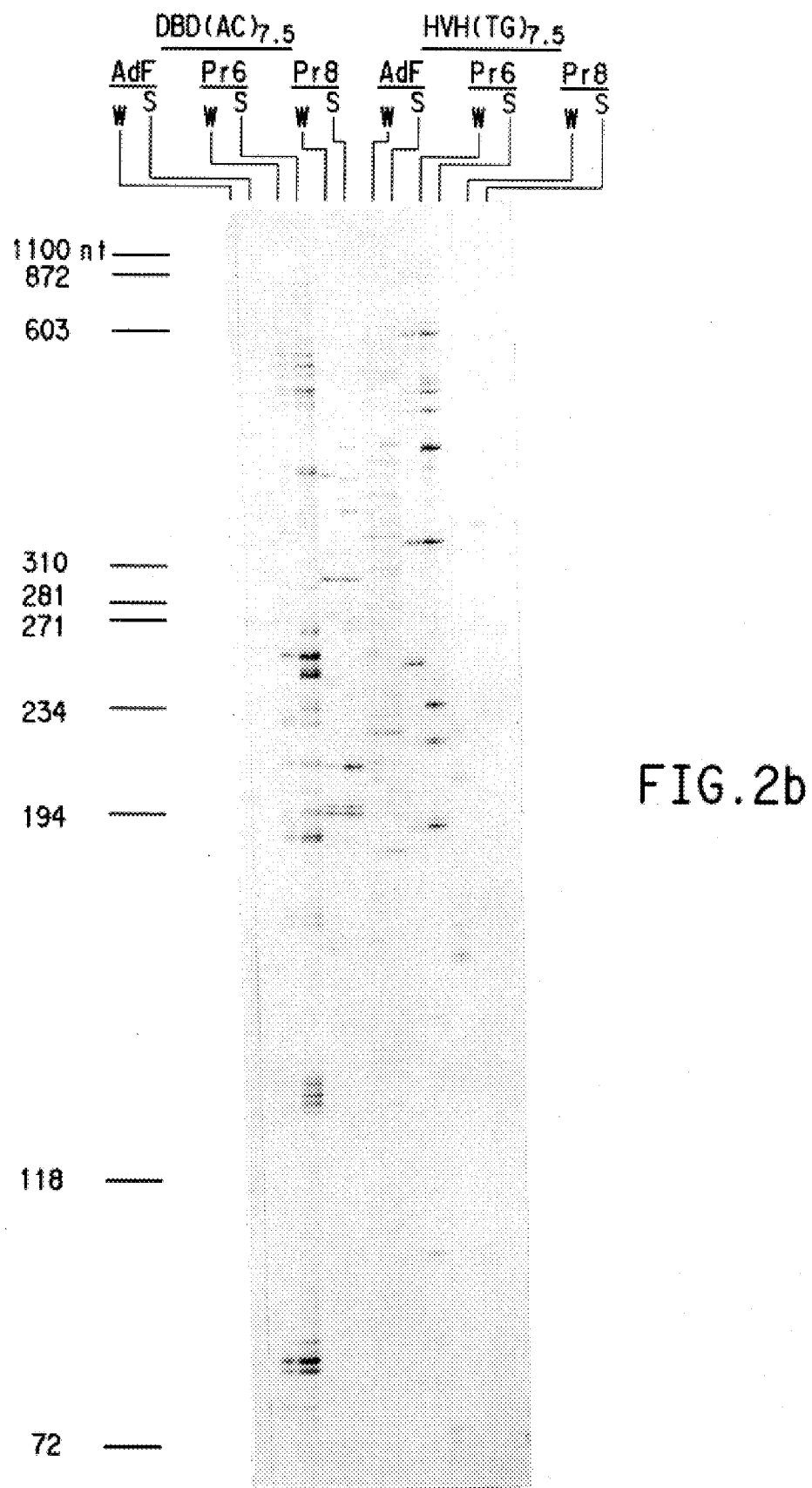

FIGS. 2A–2B illustrates an autoradiograph of a denaturing polyacrylamide gel that compares the co-amplified products from SSR-to-adaptor reactions on Taq I+Pst I digested, adaptor modified, biotin-selected template DNAs prepared from four different *Glycine max* or *Glycine soja* genotypes (N, max N85-2176; No, max NOIR-1; W, max wolverine; S, *soja* PI 81762). $^{33}$P-labeled simple SSR primers containing 3 bp degenerate anchors at their 5' ends [$HBH(AG)_{8.5}$, $DBD(AC)_{7.5}$, $HVH(TG)_{7.5}$] are paired with unlabeled Taq I adaptor-directed primers containing either zero (TaqAd.F) or one (Taq.pr6, Taq.pr8) selective nucleotide at their 3' ends. Cold start amplifications employed either a constant temperature (58° C.) or touchdown (59° C. final temperature) thermocycle profile (left and right panels, respectively). An arrow indicates a likely codominant polymorphism.

Figure 3A:
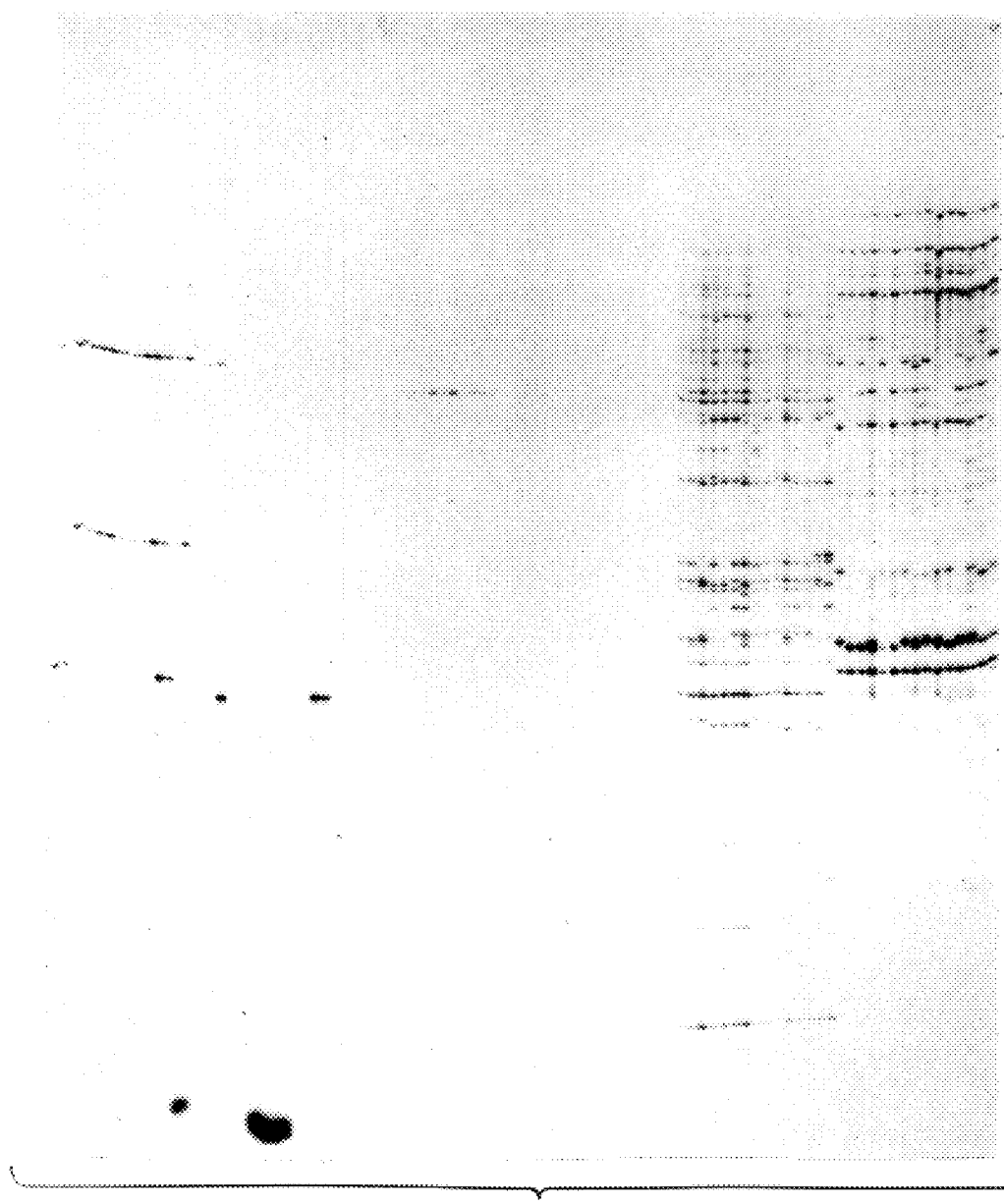
Figure 3B:
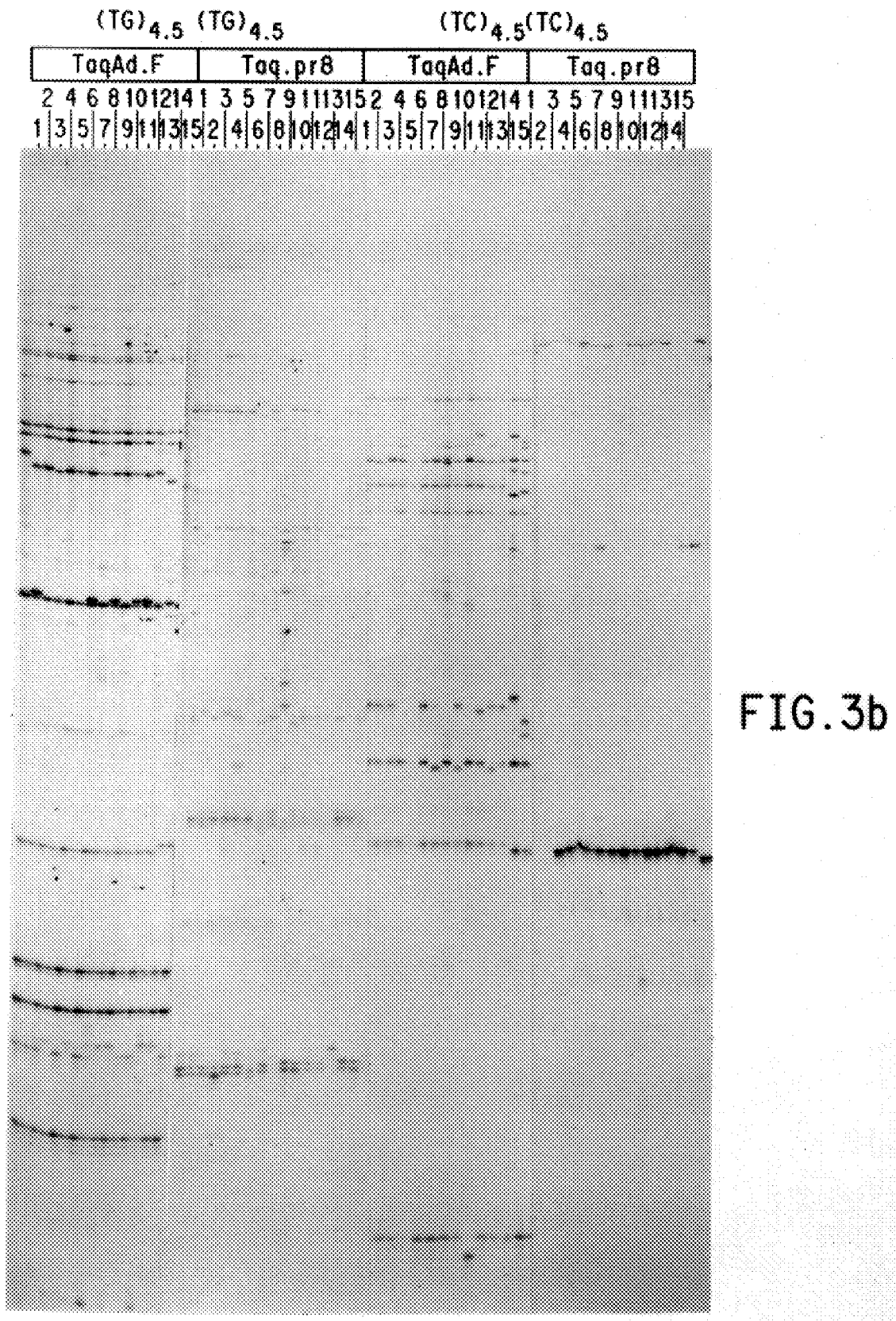

FIGS. 3a and 3b illustrate autoradiographs of denaturing polyacrylamide gels that compare the co-amplified products from SSR-to-adaptor reactions on Taq I+Pst I digested, adaptor-modified, biotin-selected templated DNAs prepared from 15 different soybean genotypes. $^{33}$P-labeled primers corresponding to perfect compound SSRs, (TC)4.5(TG)4.5, $(CT)_{7.5}(AT)_{3.5}$ and $(CA)_{7.5}(TA)_{2.5}$ [panel a] or $(TG)_{4.5}(AG)_{4.5}$ and $(TC)_{4.5}(AC)_{4.5}$ [panel b], each are paired with unlabeled Taq I-adaptor primers containing either zero (TaqAd.F) or one (Taq.pr8) 3'-selective nucleotide, under cold start amplification conditions utilizing a touchdown (56° C. final) thermocycle profile. In each set, lane 1, *Glycine max* wolverine; lane 2, G. max NOIR-1; lane 3, *G. max* N85-21761; lane 4, *G. max* Harrow; lane 5, *G. max* CNS; lane 6, *G. max* Manchu; lane 7, *G. max* Mandarin; lane 8, *G. max* Mukden; lane 9, *G. max* Richland; lane 10, *G. max* Roanoke; lane 11, *G. max* Tokyo; lane 12, *G. max* PI 54.610; lane 13, *G. max* Bonus; lane 14, *G. soja* PI 81762; lane 15, *G. soja* PI 440.913. The size distribution of products is similar to that in FIG. 2. Lane 9 of the $(TG)_{4.5}(AG)_{4.5}$+ Taq.Pr8 set is a misloading of an incorrect (non-soybean) sample.

Figure 4:
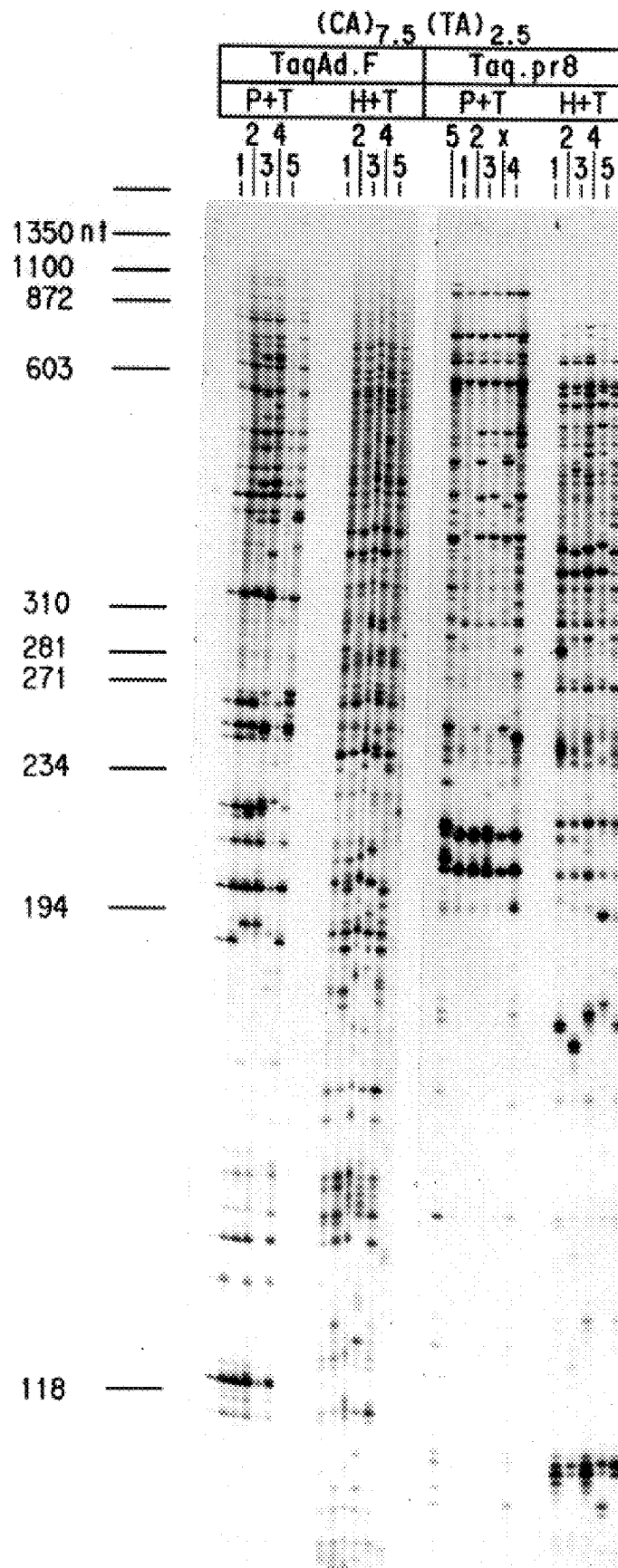

FIG. 4 illustrates an autoradiograph of a denaturing polyacrylamide gel that compares the co-amplified products from SSR-to-adaptor amplifications performed on five different soybean genotypes (lane 1, *G. max* wolverine; 2, *G. max* NOIR-1; 3, *G. max* N85-2176; 4, *G. max* Bonus; 5, *G. soja* PI 81762) prepared by digestion with Taq I combined with either Hind III or Pst I (H+T or P+T respectively). Cold start amplifications using a 56° C. touchdown thermocycle profile utilized the $^{33}$P-labeled SSR primer, $(CA)_{7.5}(TA)_{2.5}$, in combination with the indicated unlabeled Taq I adaptor-directed primer, Taq Ad.F or Taq.Pr8 (zero or one 3'-selective nucleotide, respectively). X indicates a misloaded (incorrect) lane.

Figure 5A:
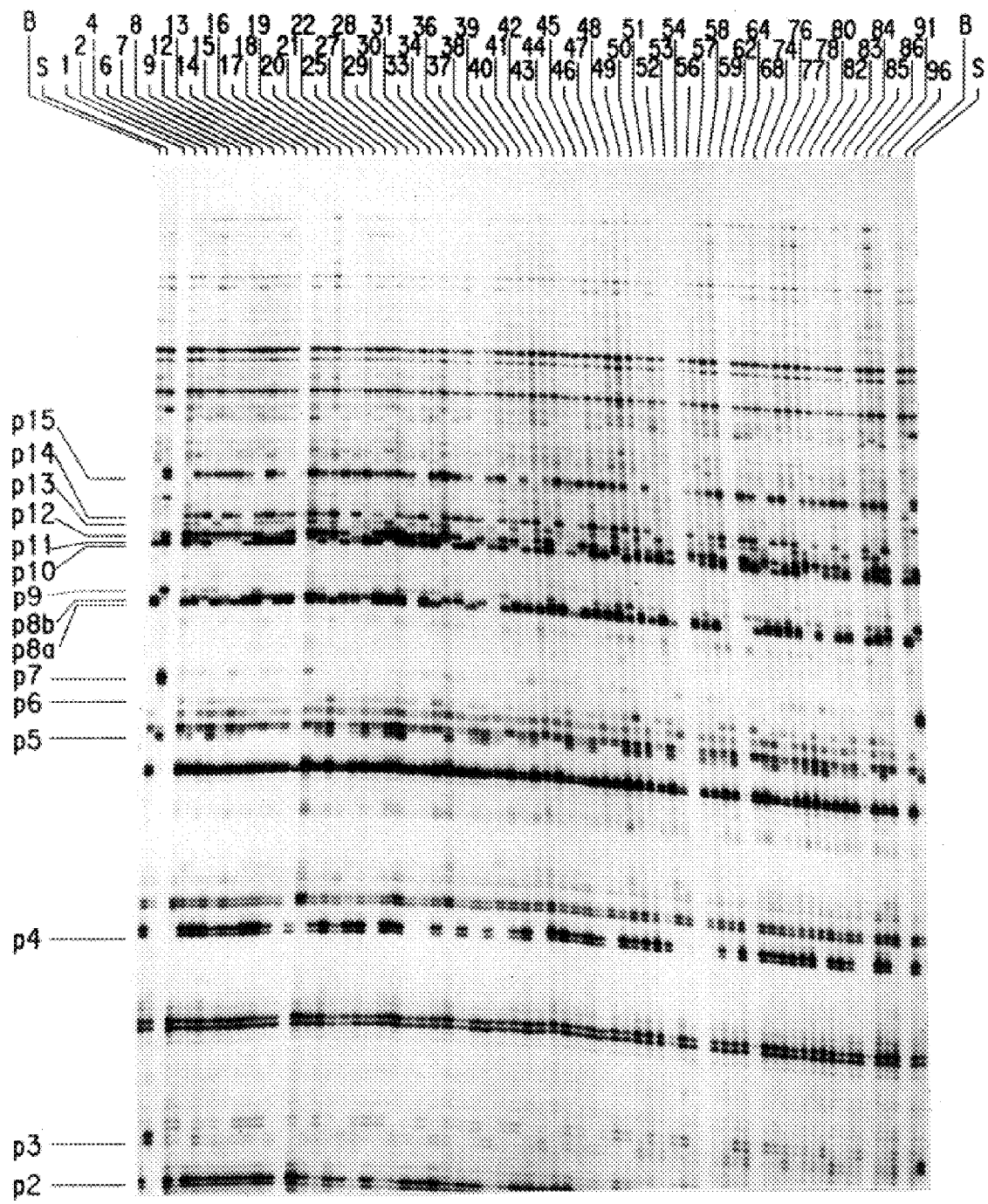
Figure 5B:
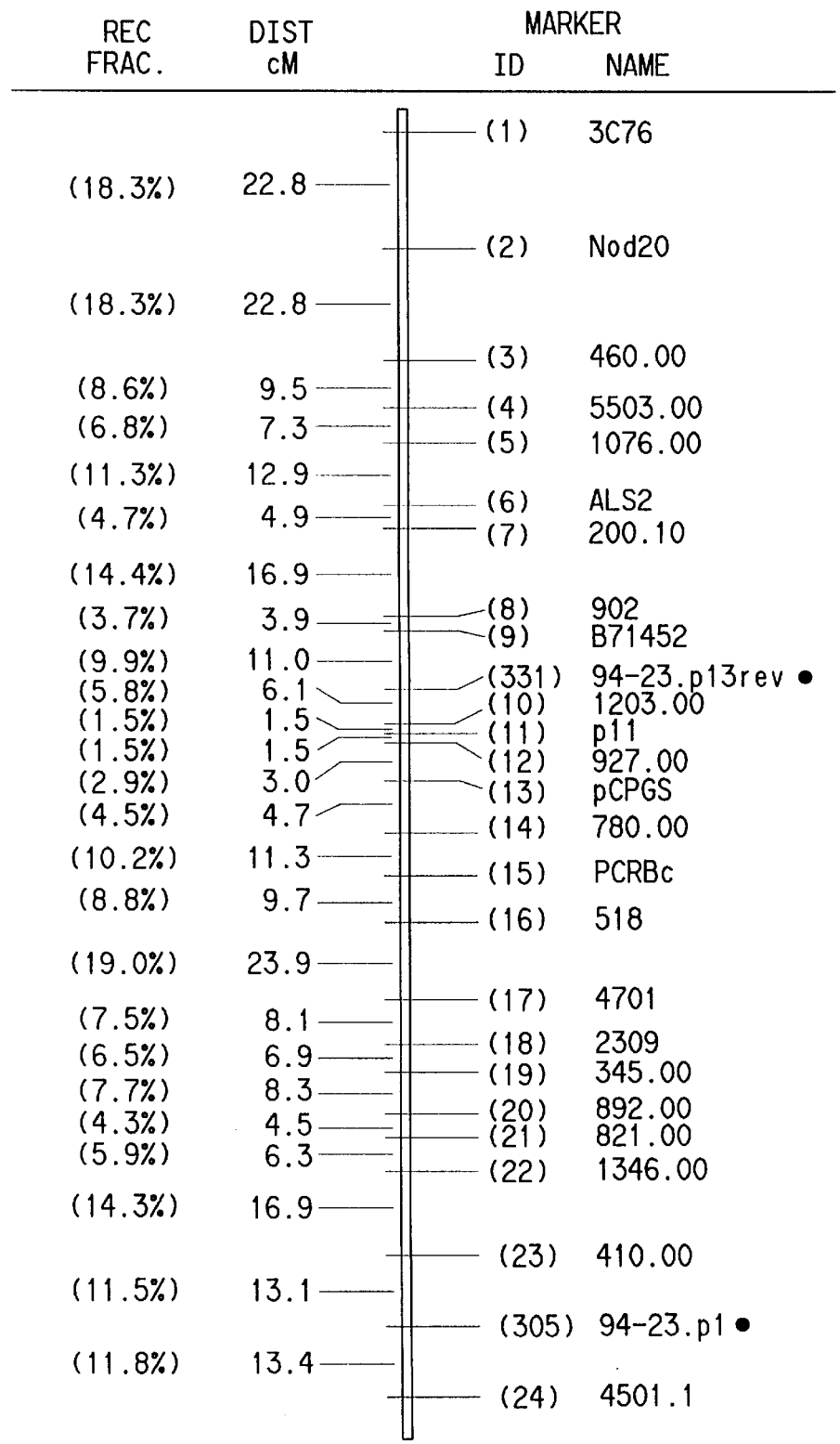
Figure 5E:
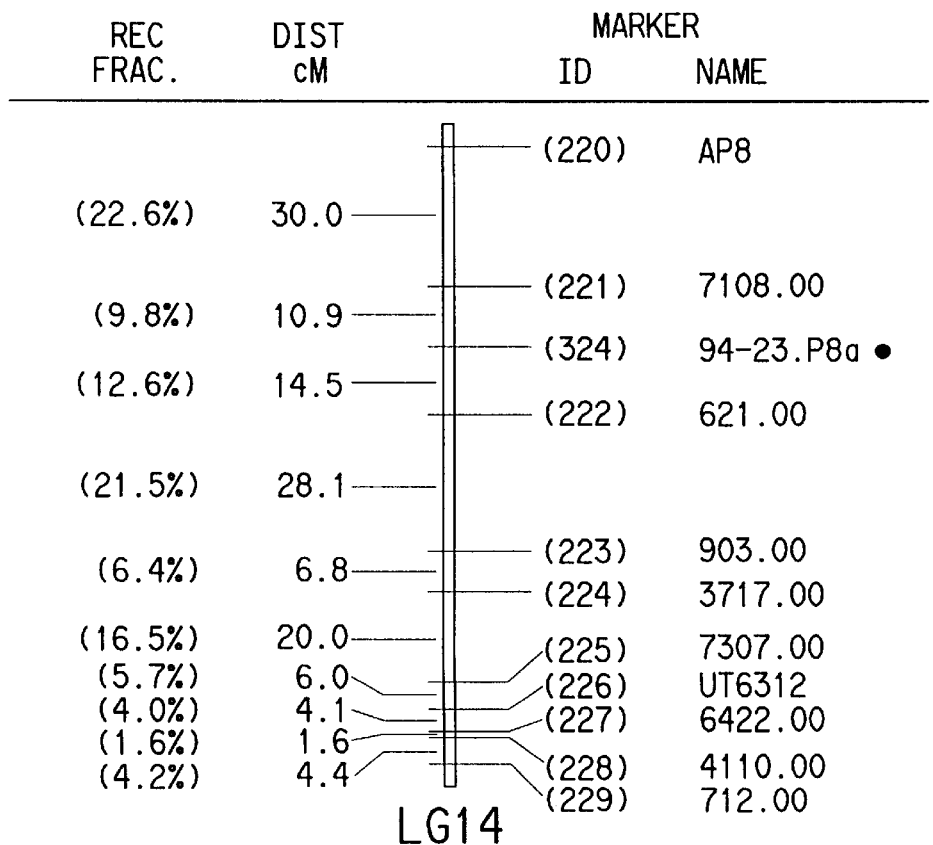
Figure 5F:
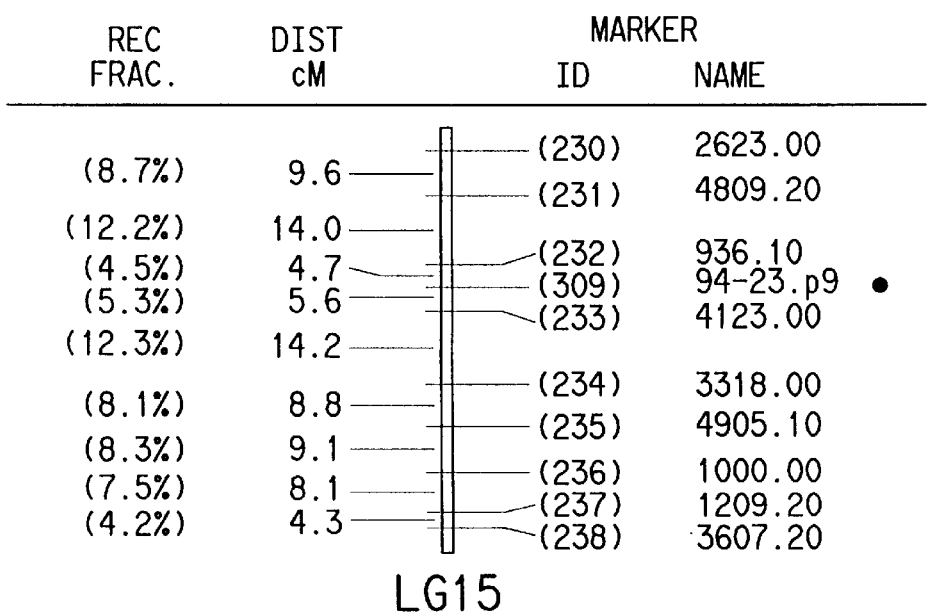

FIGS. 5A–5F illustrates an autoradiograph of a denaturing polyacrylamide gel demonstrating the segregation of polymorphic co-amplification products of 66 F2 progeny from a cross between *G. soja* PI 81762 and *G. max* Bonus. A $^{33}$P-labeled primer corresponding to the perfect compound SSR, $(CA)_{7.5}(TA)_{2.5}$, was paired with the 3'-selective nucleotide Taq.pr6 adaptor-directed primers. Blank lanes are the result of "missing data". The scored polymorphic bands that segregate in this population are indicated. B, bonus parent; S, *soja* PI81762 parent. FIG. 5b illustrates the map positions of 6 of the polymorphic segregating amplification products contained in panel a, as determined by MAPMAKER analysis of the products' respective segregation scores (contained in Table VI).

Figure 6A:
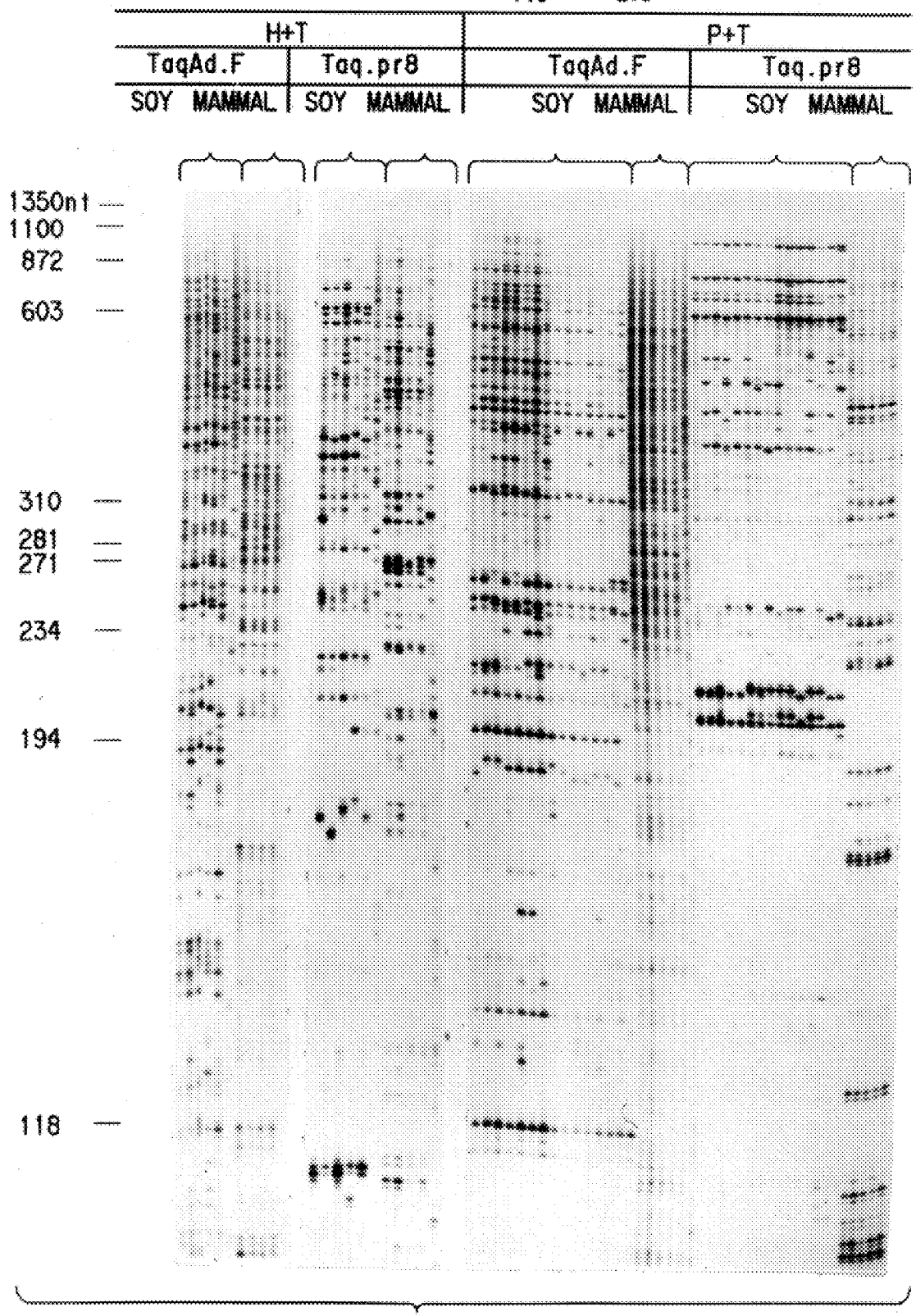
Figure 6B:
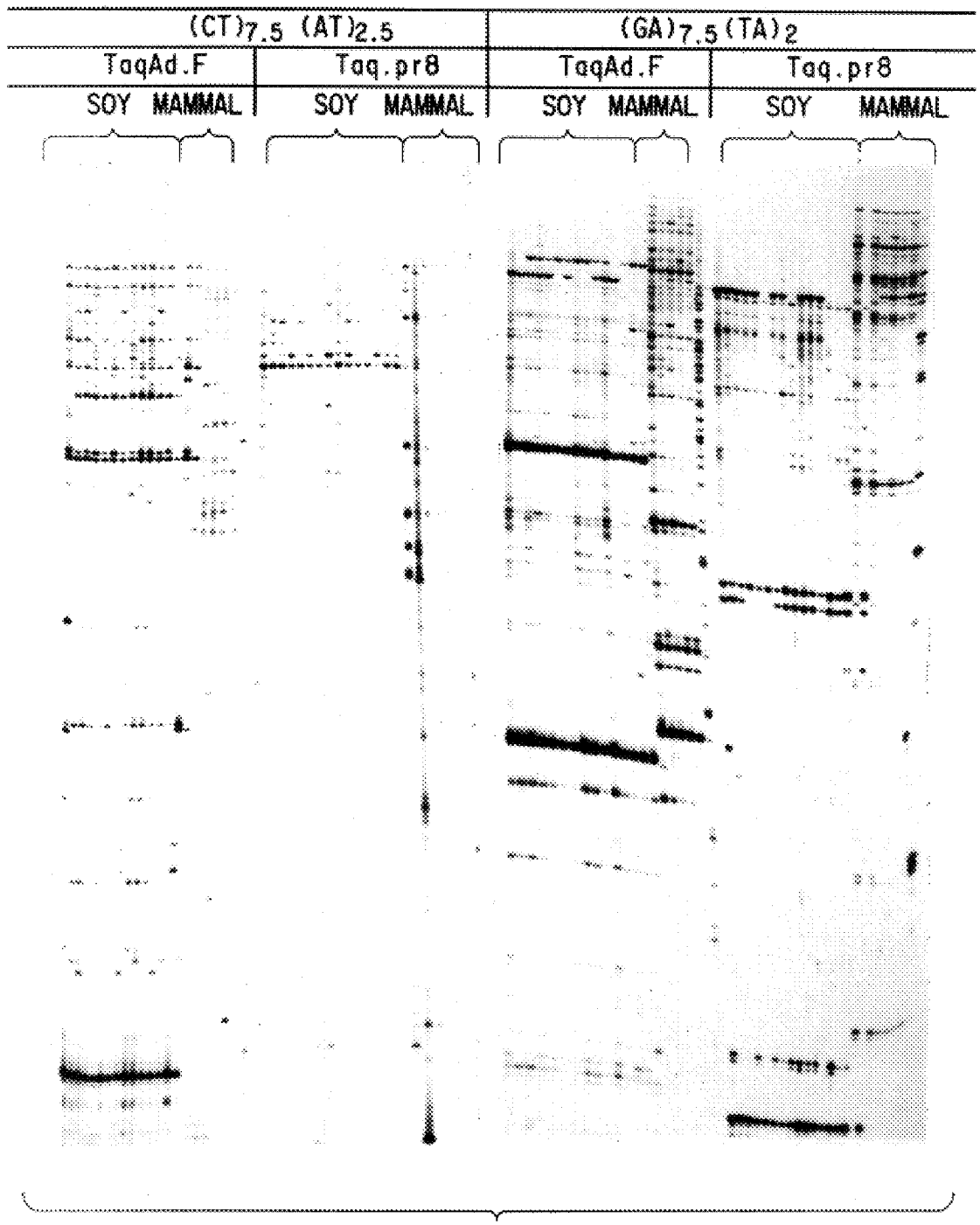
Figure 6C:
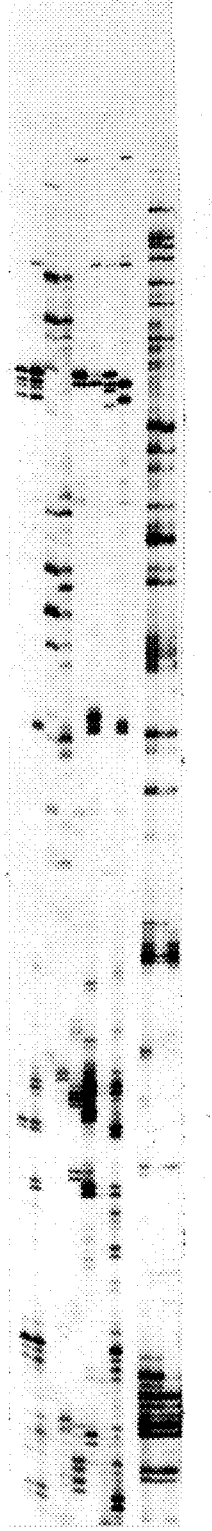

FIGS. 6A–6C illustrates an autoradiograph of a denaturing polyacrylamide gel comparing amplifications using the perfect compound SSR primer $(CA)_{7.5}(TA)_{2.5}$, paired with either the Taq.AdF or the more selective Taq.pr8 adaptor-directed primer, on template DNAs derived from either 5 (wolverine, NOIR-1, N85-2176, Bonus, PI 81762) or 15 soybean cultivars same ordering of genotypes as in FIGS. 3a and 4, respectively, and 6 mammalian individuals (one rat, four human, one mouse BALB/C). All biotin-selected templates were prepared using Taq I combined with either Hind III or Pst I. FIG. 6b illustrates a similar comparison of the co-amplification products using $(CT)_{7.5}(AT)_2$ and $(GA)_{7.5}(TA)_2$ perfect compound SSR primers, from Pst I+Taq I prepared template DNAs. The size distribution of products is similar to that in panel a. FIG. 6c illustrates the SSR-to-adaptor amplification products generated from Taq I+Hind III prepared templates of *Zea mays* (corn) and salmon DNA templates, in comparison to those from soybean Bonus and PI81762, using $(CA)_{7.5}(TA)_{2.5}$ paired with Taq.pr6 primer. Lane 1, *Z. mays* B73; lanes 2 and 3, individual salmon sources; lane 4, *Z. mays* CM27; lane 5, *Z. mays* T232; lane 6, *Z. mays* DE811ASR; lane 7, *Z. mays* LH132; lanes 8–10, two F2 individuals from a *G. max* Bonus×*G. soja* PI 81762 cross. The distribution of product sizes is similar to that shown in FIG. 6a.

Figure 7:
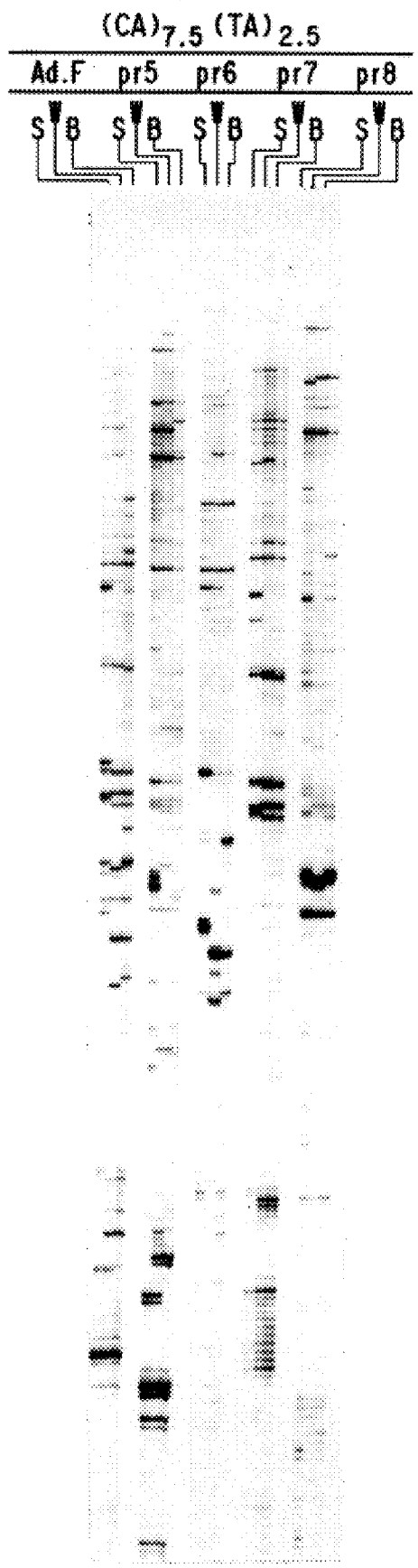

FIG. 7 illustrates an autoradiograph of a denaturing polyacrylamide gel comparing the co-amplification products from Taq I+Pst I prepared soybean templates (*S, Soja* PI81762; W, Wolverine; B, bonus) using $(CA)_{7.5}(TA)_{2.5}$ paired individually with Taq I adaptor-directed primers carrying either zero (Taq.AdF) or one specific 3'-selective nucleotide (Taq.pr5, .pr6, .pr7, .pr8).

Figure 8:
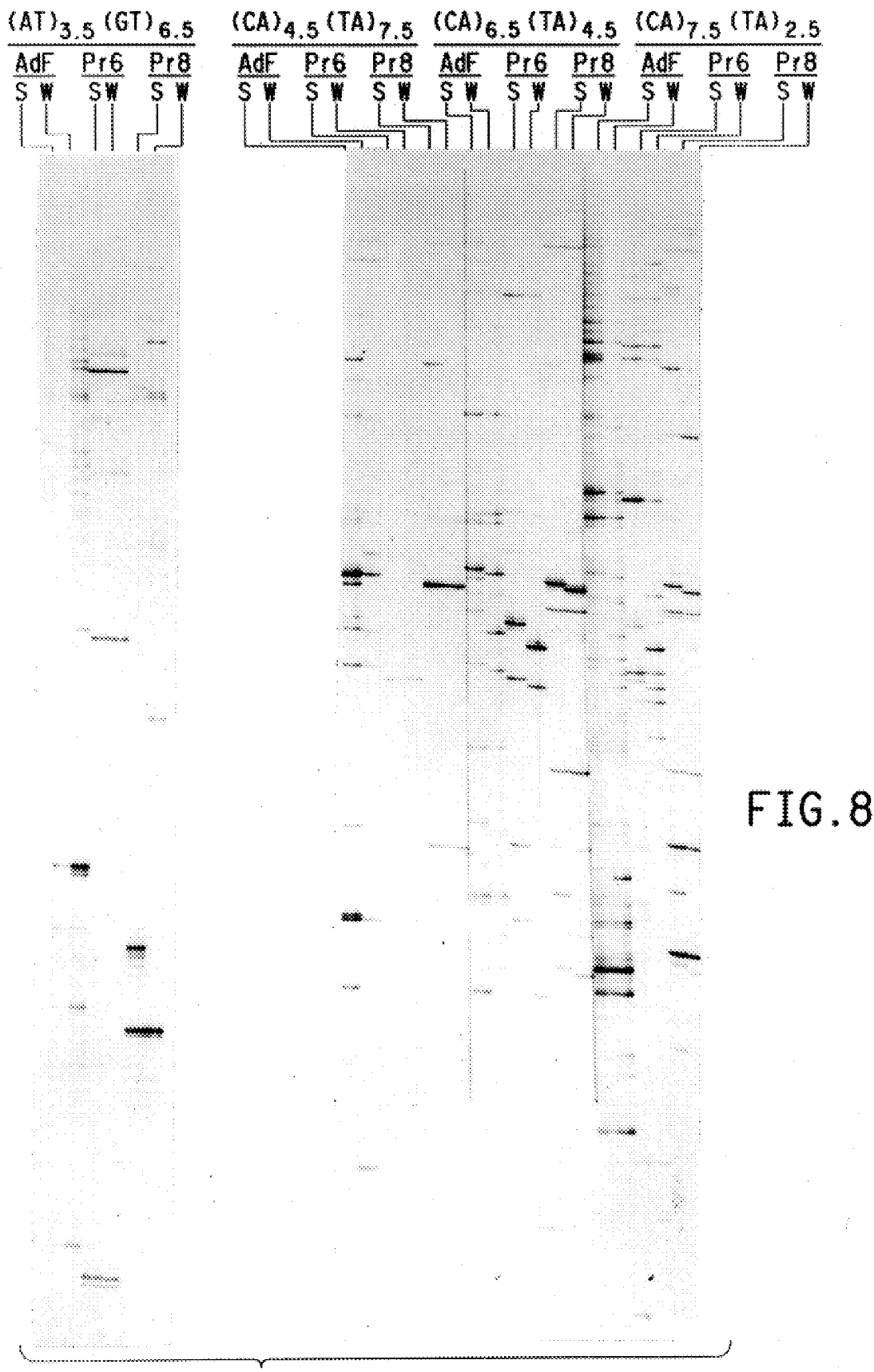

FIG. 8 illustrates an autoradiograph of a denaturing polyacrylamide gel comparing SSR-to-adaptor amplification from wolverine and PI 81762 soybean cultivars using SSR primers respresenting the complementary strands of a perfect compound SSR double stranded sequence $[(AT)_x(GT)_y: (CA)_x(TA)_y]$ paired separately with three different Taq I adaptor-directed primers, Taq.AdF, Taq.pr6 and Taq.pr8. Each strand of the double stranded compound SSR sequence is represented by three primers that differ by the relative lengths of each of the two constituent repeats within the primer. The $(AT)_{8.5}(GT)_{2.5}$ and $(AT)_{6.5}(GT)_{4.5}$ primers were completely inefficient (no amplification products generated (data not shown) and $(AT)_{3.5}(GT)_{6.5}$ was moderately successful (shown), in comparison to the three, more efficient $(CA)_x(TA)_y$ primer types.

Figure 9:
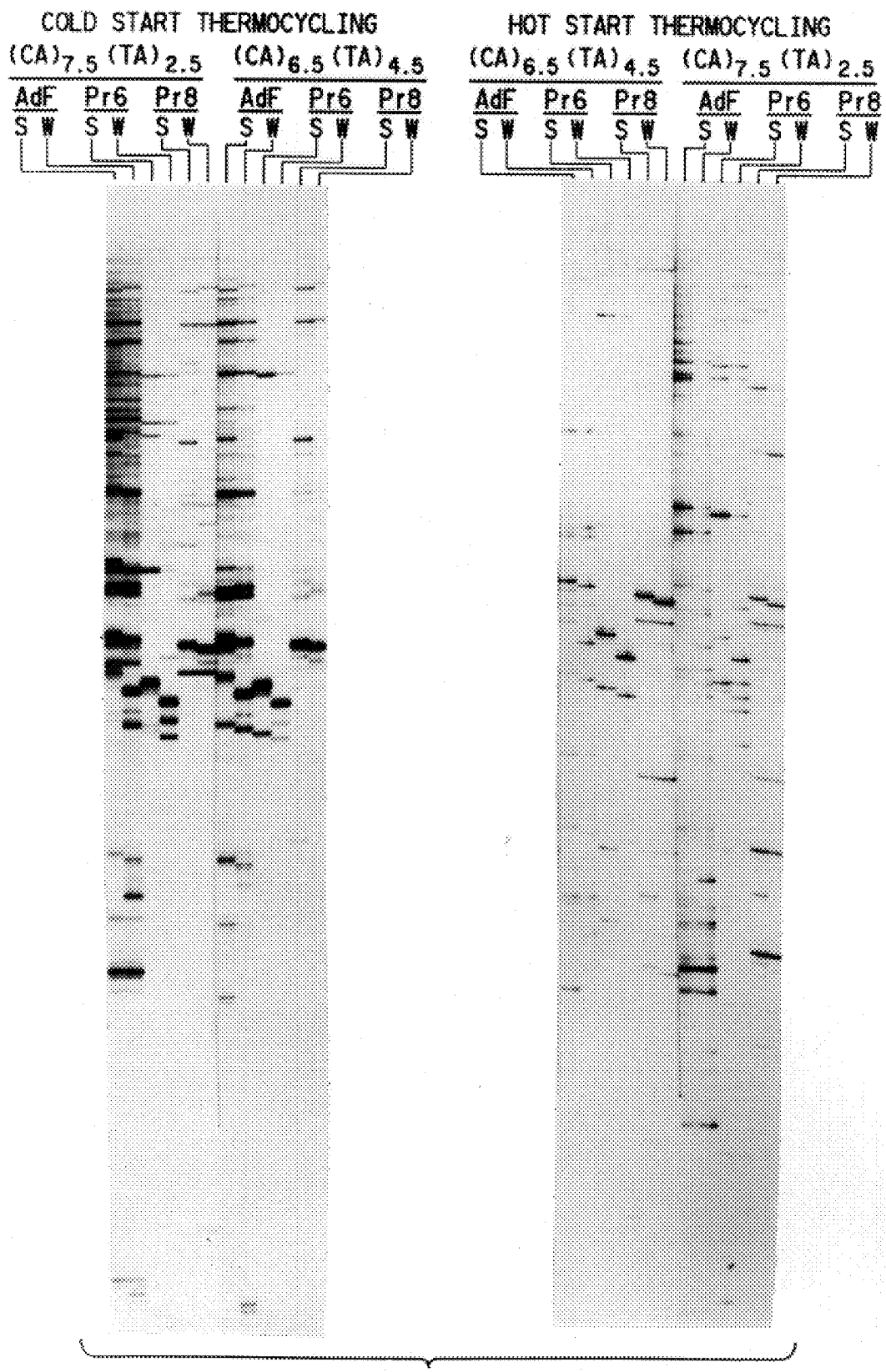

FIG. 9 illustrates autoradiographs of denaturing polyacrylamide gels that compare the co-amplification products from soybean cultivars, wolverine and PI 81762, using cold start (left) and hot start (right) methods for the initiation of thermocycling. For both methods, the perfect compound SSR primer, $(CA)_{7.5}(TA)_{2.5}$, is paired with each of the three Taq I adaptor directed primers indicated.

Figure 10A:
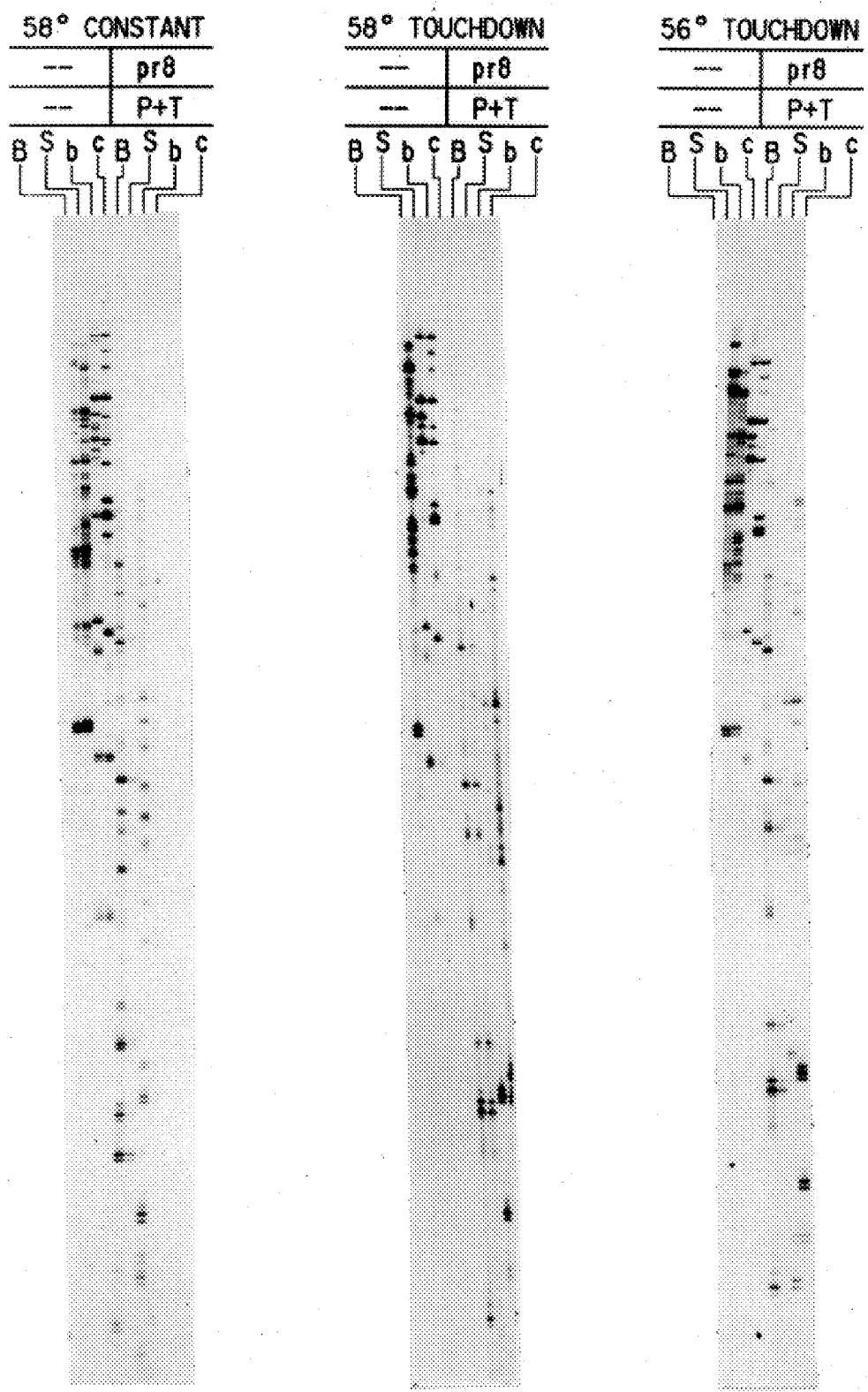
Figure 10B:
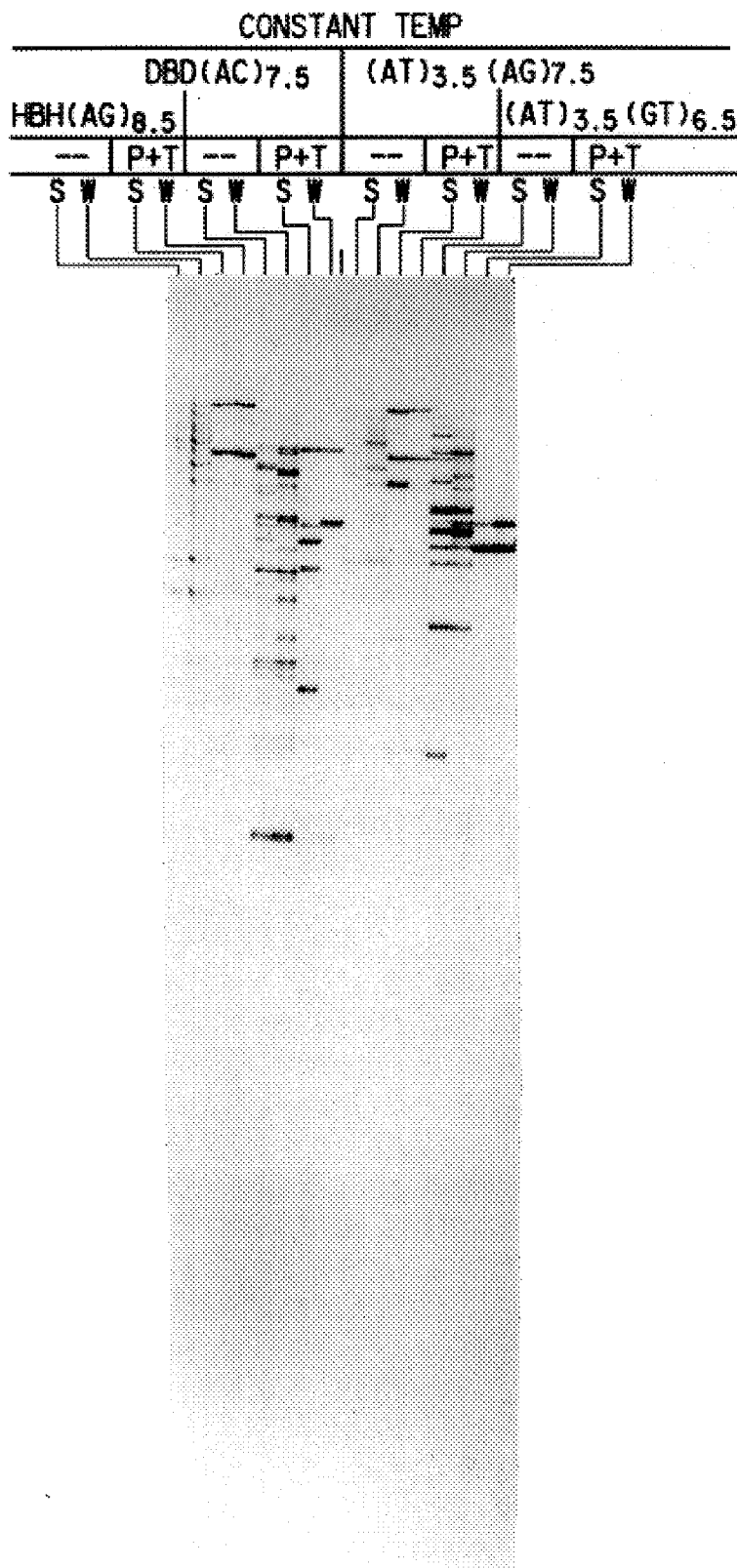
Figure 10C:
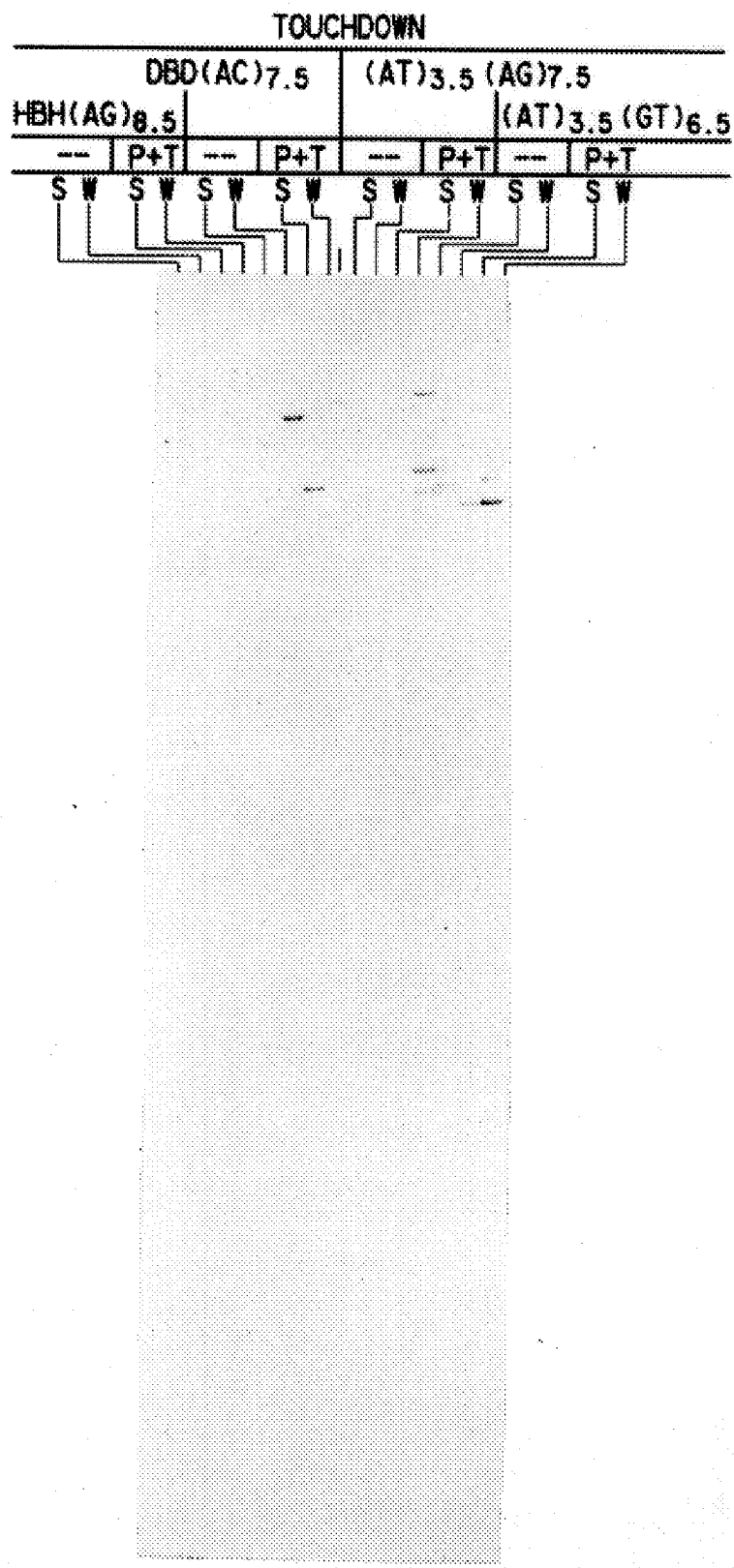

FIGS. 10A–10C illustrates an autoradiograph of a denaturing polyacrylamide gel comparing the co-amplification products from soybean (B, Bonus; S, soja; PI81762) and corn (b, B73; c, CM37) cultivars amplified using DBD(AC)$_{6.5}$ in combination with no 2nd adaptor primer or with Taq.pr8. These templates are in the form of either intact, undigested DNA or Taq I+Pst I digested DNA (P+T), as indicated.

FIG. 10b illustrates autoradiographs of denaturing polyacrylamide gels comparing the amplification products obtained using $^{33}$P-labeled 5'-anchored simple SSR primers [DBD(AC)$_{7.5}$ and HBH(AG)$_{8.5}$] or perfect compound SSR primers [(AT)$_{3.5}$(AG)$_{7.5}$ and (AT)$_{3.5}$(GT)$_{6.5}$] in single-primer amplifications (no adaptor primer used) from both undigested and Taq I+Pst I digested, biotin-selected template DNAs from soybean wolverine (W) and PI81762 (S) cultivars. Cold start amplifications used either constant temperature (58° C.) or 56° C. touchdown annealing profiles.

Figure 11:
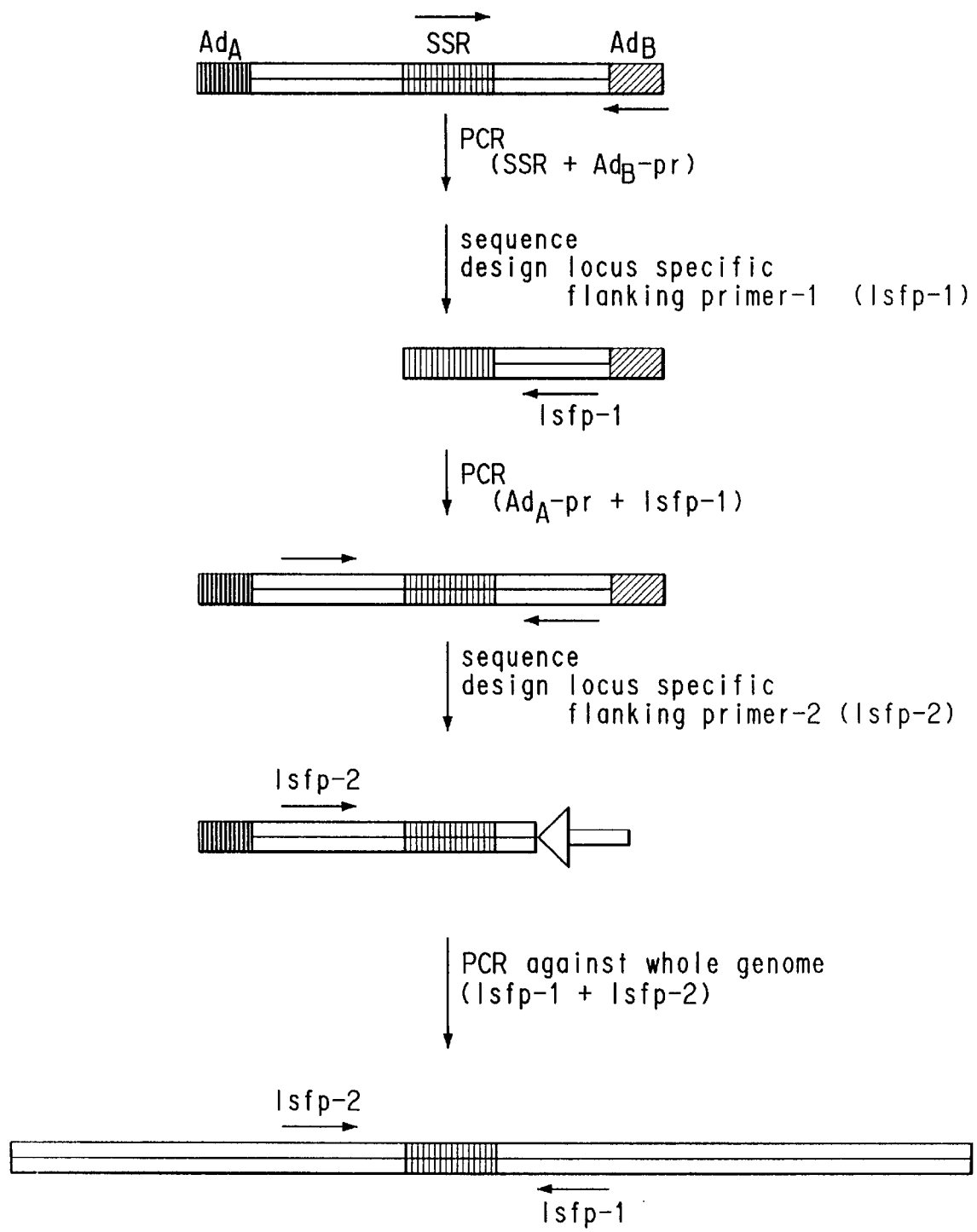

FIG. 11 is a schematic representation of the cloning and sequencing of a chosen SSR-to-adaptor amplification product, and its conversion into a defined, single-locus marker. A genomic restriction fragment carrying the targeted SSR repeat is bordered at both ends by restriction site-specific adaptors, Ad$_A$ and Ad$_B$. This fragment serves as the template for PCR amplification using an SSR-directed primer and a primer corresponding to one of the adaptors. This amplification product is purified and sequenced, and a locus-specific flanking primer (lsfp-1) is designed. This lsfp-1 primer then is paired with a primer corresponding to the other adaptor, for PCR amplification using the adaptor-modified restriction fragment mixture as template. The specific product obtained is then isolated and sequenced, and a second primer (lsfp-2) corresponding to the unique flanking sequence on the other side of the SSR is designed. The lsfp-1+lsfp-2 primer pair uniquely defines this SSR locus, and can be used to amplify directly from genomic DNA to visualize SSR length polymorphism at this locus. Applicants have provided 89 sequence listings in conformity with 37 C.F.R. 1.821–1.825 and Appendices A and B ("Requirements for Application Disclosures Containing Nucleotides and/or Amino Acid Sequences").

DETAILED DESCRIPTION OF THE INVENTION

As used herein the following terms may be used for interpretation of the claims and specification.

The term "Simple sequence repeat (SSR)" or "microsatellite repeat (MS)" or "short tandem repeat" or "dinucleotide repeat" or "trinucleotide repeat" or "tetranucleotide repeat" or "microsatellite" or "simple sequence length polymorphisms" (SSLP) all refer to stretches of DNA consisting of tandemly repeating di-, tri-, tetra-, or penta-nucleotide units. An SSR region can be as short as two repeating units, but more frequently is in excess of 8–10 repeating units. Simple sequence repeats are common in virtually all eukaryotic genomes studied and have been identified as useful tools for the study of genetic polymorphisms.

Classification of SSR loci or SSR sequences as used herein is based upon (but not identical to) the definitions suggested by Weber (Genomics 7, 524 (1990)) for the categorization of human (CA)$_n$ dinucleotide repeats.

The term "simple SSR" will refer to a region comprised of at least three or more of the same tandemly repeated di-, tri- or tetranucleotide sequence, which is not adjacent in the genome to any other different simple SSR. "Not adjacent" means not closer than four nucleotides away on either side.

The term "compound SSR" refers to a region consisting of two or more different simple SSR sequences which are adjacent. "Adjacent" means that differing simple SSR's are separated from one another by three or fewer consecutive nonrepeat nucleotides.

The term "perfect SSR" refers to a simple SSR wherein every simple repeating unit within the SSR is intact and uninterrupted by nonrepeat nucleotides.

The term "imperfect SSR" refers to a simple SSR wherein one or more of the constituent repeat units is interrupted at least once within the SSR by three or four consecutive nonrepeat nucleotides.

The term "perfect compound SSR" refers to a compound SSR wherein the two constituent repeating SSR regions are intact and uninterrupted by nonrepeat bases, (i.e., they are perfect SSR's), and the two perfect SSR regions are directly adjacent to one another, having no intervening nucleotides.

The term "in-phase" refers to a potential feature of a perfect compound SSR wherein both constituent SSR regions share a common nucleotide that retains constant spacing spanning the junction of the two SSR regions.

The term "out of phase" refers to a potential feature of a perfect compound SSR wherein a nucleotide is common to the two or more constituent repeating regions, but it does not retain constant spacing or periodicity across the junction of the compound structure.

The term "polymorphism" refers to a difference in DNA sequence between or among different genomes or individuals. Such differences can be detected when they occur within known or tagged genomic regions. A "dominant polymorphism" is a DNA difference that is detectable only as the presence or absence of a specific DNA sequence at a single locus. Methods to detect dominant polymorphisms are able to detect only one allele of the locus at a time, and genomes homozygous versus heterozygous for the detectable allele are indistinguished. A "codominant polymorphism" is a DNA difference at a locus between genomes whereby multiple alleles at the locus each can be distinguishable even when in heterozygous combinations. Typically identifiable as mobility variants on electrophoretic gels, codominant polymorphisms can produce additive, nonparental genotypes when present in heterozygous form. A dominant polymorphism is most useful as a marker when it is in coupling with the trait it marks, whereas a codominant polymorphism is equally useful when in coupling or in repulsion to a trait.

The term "touchdown amplification" or "touchdown PCR" will refer to a specific thermocycling profile for the polymerase chain reaction whereby the annealing temperature begins artificially high (or low) for the first few cycles, then is incrementally lowered (or raised) for a specified number of successive cycles until a final, desirable annealing temperature is reached. The remaining cyles of the multiple cycle profile are then performed at this final, touchdown annealing temperature. Thermocycling using this strategy serves to reduce or circumvent spurious, nonspecific priming during the initial stages of gene amplification, and imbalance between correct and spurious annealing is automatically minimized.

The terms "hot start" and "cold start" will refer to a general choice of methodologies for initiating thermocycling for a PCR amplification reaction. In a cold start amplification, all the reaction components are assembled simultaneously at room temperature, prior to the first denaturation step. This approach allows for the possibility of spurious priming and nonspecific amplification products resulting from primer annealing and primer extension at undesirably low temperatures. In contrast, a hot start approach employs the deliberate omission of at least one key component from the otherwise complete amplification reaction, thus preventing either primer annealing (if primer is omitted) or extension (if either polymerase or nucleotides are omitted). After carrying out an initial high-temperature denaturation, the excluded component is added, and thermocycling proceeds. A hot start amplification thus serves to reduce or eliminate the production of nonspecific products that result from spurious primer extension at nonstringent temperatures. "Nucleic acid" refers to a molecule which can be single stranded or double stranded comprised of monomers (nucleotides) containing a sugar, phosphate and either a purine or pyrimidine. In bacteria, lower eukaryotes, and in higher animals and plants, "deoxyribonucleic acid" (DNA) refers to the genetic material while "ribonucleic acid" (RNA) is involved in the translation of the information from DNA into proteins.

The terms "genomic DNA" or "target DNA" or "target nucleic acid" will be used interchangably and refer to nucleic acid fragments targeted for amplification or replication and subsequent analysis by the instant method for the presence of SSR regions. Sources of genomic DNA will typically be isolated from eukaryotic organisms. Genomic DNA is amplified via standard replication procedures using suitable primers to produce detectable primer extension products.

The term "restriction endonuclease" or "restriction enzyme" is an enzyme that recognizes a specific palindromic-base sequence (target site) in a double-stranded DNA molecule, and catalyzes the cleavage of both strands of the DNA molecule at a particular base in every target site.

The term "restriction fragments" refers to the DNA molecules produced by digestion with a restriction endonuclease. Any given genome may be digested by a particular restriction endonuclease into a discrete set of restriction fragments. The DNA fragments that result from restriction endonuclease cleavage may be separated by gel electrophoresis and detected, for example, by either fluorescence or autoradiography.

The term "restriction fragment length polymorphism (RFLP)" refers to differences in the genomic DNA of two closely related organisms which are detected based upon differences in the pattern of restriction fragments generated by a restriction endonuclease digestion of genomic DNA of the organisms. For example, a genome which contains a polymorphism in the target site for a restriction endonuclease will not be cleaved at that point by the restriction endonuclease. Or, a nucleotide sequence variation may introduce a novel target site where none exists in the other organism, causing the DNA to be cut by the restriction enzyme at that point. Additionally, insertions or deletions of nucleotides occurring between two target sites for a restriction endonuclease in the genome of one organism will modify the distance between those target sites. Thus, digestion of the two organism's DNA will produce restriction fragments having different lengths and will generate a different pattern upon gel electrophoresis.

The term "ligation" refers to the enzymatic reaction catalyzed by the enzyme T4 DNA ligase by which two double-stranded DNA molecules are covalently joined together in their sugar-phosphate backbones via phosphodiester bonds. Ligation can occur between two DNA molecules that each are bounded by blunt (nonstaggered) ends, but also can occur if the two DNA molecules contain single-stranded overhanging ends that are complementary in sequence. In general, both DNA strands of the two double helices are covalently joined together such that at each junction the free 5' end of one of the DNA molecules carries a 5'-phosphate group. It is also possible to prevent the ligation of one of the two strands, through chemical or enzymatic modification (for example, removal of the 5' phosphate) of one of the ends, in which case the covalent joining would occur in only one of the two DNA strands.

The term "adaptor" will specifically refer herein to short, largely double stranded DNA molecules comprised of a limited number of base pairs, e.g., 10 to 30 bp. Adaptors are comprised of two synthetic single-stranded oligonucleotides having nucleotide sequences that are not intentionally represented by repetitive sequences in the genome of interest, and also are in part complementary to each other. Under appropriate annealing conditions, the two complementary synthetic oligonucleotides will form a partially double-stranded structure in solution. At least one of the ends of the adaptor molecule is designed so that it is complementary to and can be specifically ligated to the digested end of a restriction fragment.

The term "polymerase chain reaction" or "PCR" refers to the enzymatic reaction in which copies of DNA fragments are synthesized from a substrate DNA in vitro (U.S. Pat. Nos. 4,683,202 and 4,683,195). The reaction involves the use of one or more oligonucleotide primers, each of which is complementary to nucleotide sequences flanking a target segment in the substrate DNA. A thermostable DNA polymerase catalyzes the incorporation of nucleotides into the newly synthesized DNA molecules which serve as templates for continuing rounds of amplification.

The term "DNA amplification" or "nucleic acid amplification" or "nucleic acid replication" or "primer extension" refers to any method known in the art that results in the linear or exponential replication of nucleic acid molecules that are copies of a substrate DNA molecule.

The term "primer" refers to a DNA segment that serves as the initiation point or site for the replication of DNA strands. Primers generally will be single-stranded and will be complementary to at least one strand of the target or substrate nucleic acid and will serve to direct nucleotide polymerization or primer extension using the targeted sequence as a template. Primers may be used in combination with another primer to "flank" the target sequence in PCR, thus forming a "primer set" or "primer pair". In general, primers are 14 to 40 nucleotides long and preferably are designed so as not to form secondary structure or hairpin configurations. Specific requirements for primer size, base sequence, complementarity and target interaction are discussed in the primer section of the detailed description of the invention. The term "primer", as such, is used generally herein by Applicants to encompass any synthetic or naturally occurring oligonucleotide that can hydrogen-bond specifically to a region of a substrate DNA molecule and functions to initiate the nucleic acid replication or primer extension process; such processes may include, for example, PCR, or other enzymatic reactions that employ single rather than multiple oligonucleotide initiators.

The term "anchor" or anchor region" or "anchor portion" refers to a 3–20 nucleotide region of a primer designed to hybridize with a DNA sequence which is immediately adjacent to a specified sequence SSR. The anchor region of a primer may occur at either the extreme 5' or 3' end, and serves to affix the primer onto the target DNA at an adjacent position relative to a specified SSR. This anchoring results in primer extension occurring from a fixed nucleotide at each target site. The anchor sequence can be a nondegenerate sequence of either deliberate or arbitrary design, or it can be a fully or partially degenerate sequence. The latter would be capable of annealing to the genomic DNA sequences flanking a wide range of SSR sites in a genome. Optionally, the anchor portion of the primer may be 5' end-labeled with a reporter molecule, typically a radioisotope, a fluorescent moiety or a reactive ligand.

The use of the term "arbitrary" when speaking of an individual nucleotide at each position in a DNA sequence refers to selection based on or determined by unbiased means or seemingly by chance rather than by necessity or by adherence to a predetermined sequence.

The term "non-degenerate" refers to the occurrence of a single, specified nucleotide type at a particular position or at multiple specified positions in the linear ordering of nucleotides in a DNA polymer, usually an oligonucleotide or a polynucleotide. Any nondegenerate nucleotide position can carry an intended base (either A, G, C or T) that is known for example to correspond to a given template site, or it can carry an arbitrarily chosen base, which will correspond to a target site that is not known a priori. A "non-degenerate oligonucleotide" means that every nucleotide position within the DNA molecule is non-degenerate. The term "degenerate" refers to the occurrence of more than one specified nucleotide type at a particular position in an oligonucleotide or polynucleotide. A specific oligonucleotide can be made up of some positions that are degenerate and some positions that are fully or partially degenerate. "Fully degenerate" indicates the presence of an equal mixture of the four possible nucleotide bases (A, G, C or T) at a particular nucleotide position; partially degenerate indicates the presence of only two or three of the four possible bases at a particular position. A "degenerate oligonucleotide" is one in which at least one position within it carries full or partial degeneracy; such an oligo- or polynucleotide is a mixture of specific, nondegenerate DNA molecules, each of which represents a single permutation of the nucleotide sequences possible by virtue of the degenerate base(s) specified in the linear nucleotide sequence. An oligonucleotide with two fully degenerate positions, for example, would be a mixture of $(4)^2=16$ different nondegenerate molecules; an oligonucleotide with four fully degenerate and two partially degenerate (three bases) positions would comprise a mixture of $(4)^3 \times (3)^2=576$ different non-degenerate molecules. Standard degeneracy codes used herein are:

| N or X | A, G, C or T |
| B | G, C or T [anything except A] |
| D | A, G or T [anything except C] |
| H | A, C or T [anything except G] |
| V | A, C or G [anything except T] |

The term "reporter" or "reporter molecule" refers to any moiety capable of being detected via enzymatic means, immunological means or energy emission; including, but not limited to, fluorescent molecules, radioactive tags, light emitting moieties or immunoreactive or affinity reactive ligands.

The term "binding pair" includes any of the class of specific inter-molecular or recognition immune-type binding pairs, such as antigen/antibody or hapten/anti-hapten systems; and also any of the class of nonimmune-type binding pairs, such as biotin/avidin; biotin/streptavidin; folic acid/folate binding protein; complementary nucleic acid segments; protein A or G/immunoglobulins; and binding pairs which form covalent bonds, such as sulfhydryl reactive groups including maleimides and haloacetyl derivatives, and amine reactive groups such as isothiocyanates, succinimidyl esters and sulfonyl halides.

The present invention describes the design and use of self-anchoring primers for the detection of SSR genetic markers. The general polymorphism detection method using these primers is termed selective amplification of microsatellite polymorphic loci (SAMPL). The method of primer design is based on the observation that many compound SSR sequences are composed of dinucleotide repeats wherein a single type of nucleotide is shared by both of the directly adjacent constituent repeats and is maintained "in-phase" across the repeat junction and throughout the length of the repeat. The present invention combines many of the advantages inherent to conventional, single-locus SSR markers (i.e., high levels of polymorphs and high codominance potential), with the added benefits and convenience offered by multiplexed genome assays. As with conventional single-locus SSR markers, the use of perfect compound SSR sequences as self-anchored PCR primers enables the identification of dominant and codominant polymorphisms between genomes. However, unlike conventional SSR analysis, this method requires no prior knowledge of the unique sequences flanking individual SSR loci. Thus, no labor-intensive SSR marker discovery or locus identification is necessary to use such compound SSR sequences as primers as we describe. Also, as with conventional SSR markers, the in-phase subset of compound SSR sequences appears to be highly abundant and well dispersed in both plant and animal genomes, as well as to be highly polymorphic between individual genomes. In contrast, the "out-of-phase" subset of perfect compound SSR sequences are represented in these same genomes at much lower relative frequencies. Therefore, the likelihood that the highly abundant, in-phase perfect compound SSR sequences can identify new polymorphisms closely linked to loci of interest is extremely high. Additionally, PCR primers representing these compound SSR sequences are self-anchoring, such that the 5'-most repeat serves as the anchor for primer extension by the 3'-most of the two repeats, thus obviating the need to incorporate into these primers any additional degenerate or fixed sequences as 5' or 3' flanking anchors. Therefore, conceivably every genomic locus harboring the same compound SSR sequence would be expected to serve as a target site for simultaneous amplification by the single compound SSR primer matching these target sites. Finally, and most preferred, the use of these primers can be incorporated into several different genome assays to increase their versatility and informativity. For example, the use of these perfect, in-phase compound SSR primers in modifications of the amplified fragment length polymorphism assay (AFLP; Zabeau, EP 534,858) leads to an increase in the proportion of amplification products that are polymorphic and codominant between even highly related genomes as compared to conventional AFLP methods. The versatility of these compound SSR primers, in combination with the ability to fine-tune both the numbers and types of amplification products achievable with the AFLP assay, offers a unique combination of benefits for the multiplexed analysis of complex plant and animal genomes.

Applicants' modified AFLP invention is illustrated in FIG. 1. Genomic DNA (I) carrying perfect in-phase compound SSR sequences at some frequency of occurrence is digested with a single restriction enzyme, or with a combination of two or more restriction enzymes. This Figure demonstrates the use of a double enzyme combination, one enzyme having a hexanucleotide recognition site (hatched boxes) and the other a tetranucleotide site (dark boxes). It is also within the scope of the invention to choose other combinations of multiple restriction enzymes, including but not limited to the following combinations of restriction enzymes with the specified types (lengths) of recognition site:

| Additional Enzyme combinations | |
|---|---|
| two enzymes | three enzymes |
| 4 + 4 | 4 + 4 + 4 |
| 5 + 5 | 5 + 4 + 4 |
| 6 + 6 | 6 + 4 + 4 |
| 4 + 5 | 5 + 4 + 5 |
| 5 + 6 | 6 + 4 + 5 |
| 4 + 8 | 6 + 4 + 6 |
| 5 + 8 | 5 + 5 + 5 |
|  | 5 + 5 + 6 |
|  | 6 + 6 + 6 |

In all cases, these multiple enzyme digestions produce a mixture of restriction fragments with all combinations of the corresponding blunt or single stranded overhanging ends. Additionally it is within the scope of the invention for a single restriction enzyme to be used to produce fragments all sharing the same blunt or single-stranded overhanging ends. In general, any enzyme with a 4-, 5-, 6- or 8-bp recognition site is suitable, providing the enzyme's activity is not affected or inhibited by DNA methylation or other, nonmendelian modes of DNA modification within the enzyme site.

Figure 1A:
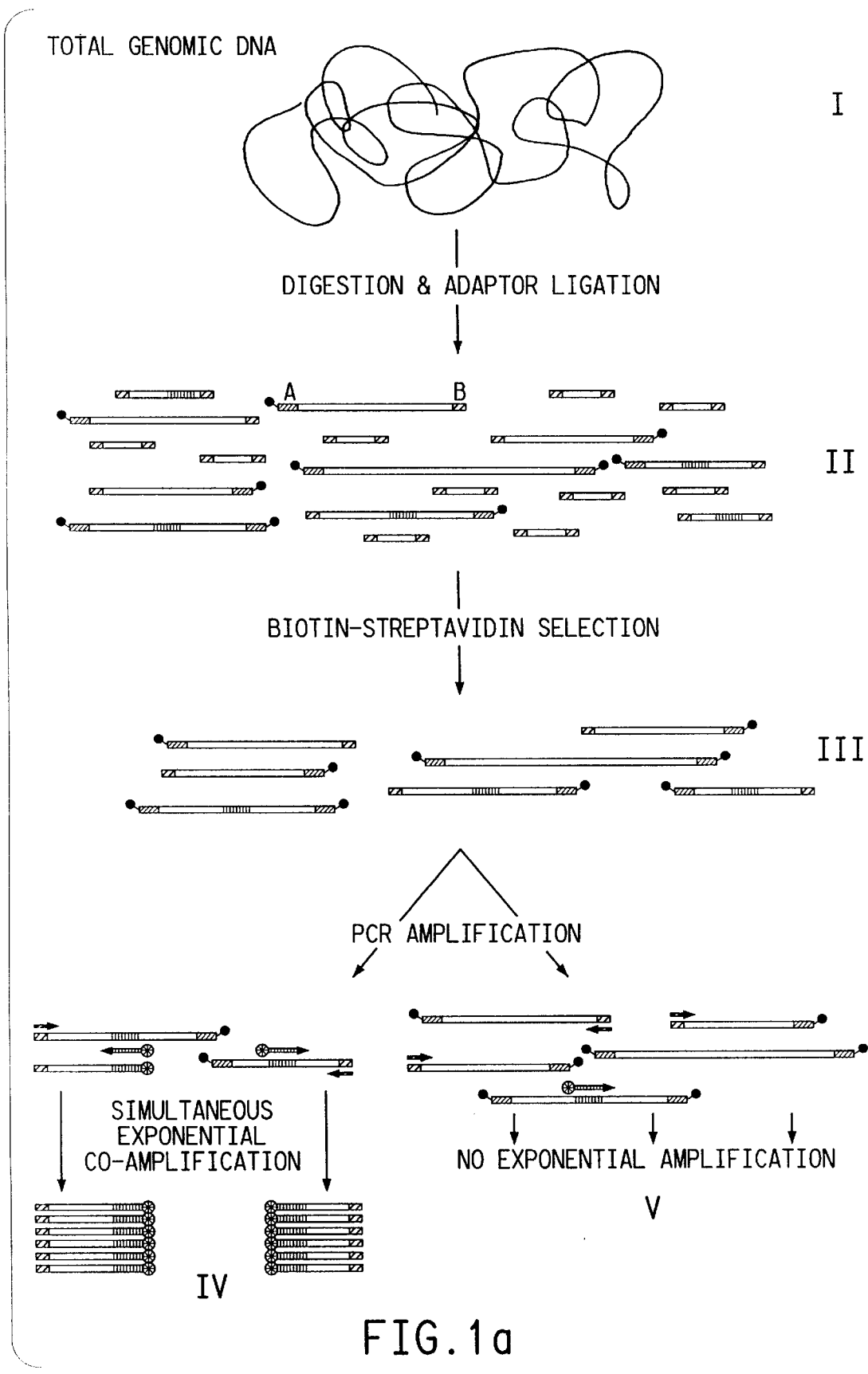

Next, double stranded adaptors A and B are constructed wherein Adaptor A anneals specifically to the single stranded overhang produced by the hexanucleotide-site enzyme, and Adaptor B to the overhang left by the tetranucleotide-site enzyme. Adaptors A and B are simultaneously ligated to the appropriate ends of all the restriction fragments (II) in the digested DNA mixture using standard methods (also described in Table III). In an alternate embodiment, either Adaptor A or Adaptor B may be conjugated with a member of a binding pair such as biotin (as part of a biotin-streptavidin pair), allowing capture and isolation of a smaller subset of the genomic restriction fragments (III). Either of the adaptors can be so modified; the proportion of genomic fragments then selected for is affected by the genomic frequency of the specific restriction site recognized by the modified adaptor. For any given restriction enzyme combination, this enrichment method categorically allows only a small fraction of the total number of restriction fragments from a genome the opportunity to serve as template for the subsequent PCR amplification; however, this reduced complexity is necessary for ensuring a manageable number of co-amplified products in the next step. The entire genome can be examined through the use of multiple combinations of restriction enzymes for the generation of different sets of enriched genomic fragments. FIG. 1a illustrates a biotinylated hexanucleotide site adaptor.

Alternatively, the complexity of the genomic fragment mixture can be selectively reduced by performing a pre-amplification step prior to the final amplification, using a pair of unlabeled adaptor-directed primers. This primer pair comprises two different primers, one corresponding to one adaptor sequence and the second primer to the other adaptor sequence. Each primer carries one selective nucleotide at its 3'-end. Since the 3'-most position of each of these +1 adaptor primers can be occupied by any one of the four DNA nucleotides, each adaptor can be represented by 4 different primers. Furthermore, 4×4=16 different combinations of these +1 primers can be used against any genomic fragment mixture to generate 16 different, nonoverlapping fragment subsets from each genome. Thus, the pre-amplification enriches for a subset of the total mixture of genomic fragments, and different enriched subsets can be generated from a single restriction fragment mixture by varying the specific primers used for the pre-amplification.

No matter how the fragment enrichment is performed, a pair of PCR primers next are synthesized according to standard protocols. One primer will be an adaptor-directed primer, designed to anneal to adaptor B specifically when the biotin-mediated fragment enrichment method is employed. For enrichment via pre-amplification, this primer can correspond to either of the two adaptors. In either case, this adaptor primer carries 1–4 randomly selected nucleotides at their 3'-ends.

The other primer will be a SSR-directed primer, designed to anneal specifically to a particular SSR sequence represented on a subset of the genomic fragments. In a preferred embodiment, the SSR-directed primer is 5'-end labeled, typically with a radionucleotide such as $^{32}P$ or $^{33}P$ or with a fluorescent moiety (*). It is further especially preferred if the SSR-directed primer is of the "perfect compound" type wherein the primer straddles the compound SSR, preferably with one nucleotide remaining "in-phase" across the length of the primer. Exponential amplification of a subset of the adaptor modified restriction fragments in the presence of the adaptor-directed primer and the 5'-labeled SSR primer generates labeled primer extension products (IV) from every input genomic fragment that carries the SSR sequence and is bordered at the opposing end by the designated adaptor sequence.

This method generates multiple co-amplification products, a high proportion of which are expected to be polymorphic between genomes. Those genomic fragments lacking either the designated SSR sequence or the appropriate adaptor end, or both, will not be exponentially amplified, and therefore will not be detected (V).

General Methods

Primer Design:

All oligonucleotides primers are synthesized using solid-phase phosphoramidite chemistry such as that described by Operon Technologies, Alameda, Calif. All primers are non-phosphorylated at their 5' ends and can be used in unpurified form providing efficient syntheses. However, oligonucleotides purified by column chromatography are preferred for optimal primer specificity. All oligonucleotide primer sequences are chosen such that the $T_m$ in 50 mM salt (KCl or NaCl) is between 38° and 45° C. (as determined using the algorithm employed by Oligo v4.03 for the Macintosh, National Biosciences, Inc.).

Several types of primers are used within the context of Applicants' invention. The first is an adaptor-directed primer (as disclosed in Zabeau EP 534,858) which can vary from 15 to 25 nucleotides in length, and from 40% and 60% G+C. Starting at its 5' end, the primer spans the length of, and is complementary to, one strand of a double-stranded adaptor that is ligated to the restriction endonuclease-digested target DNA to be tested. The primer then covers all or part of the restriction site, and its 3' end can carry arbitrary, nondegenerate bases that anneal to and prime from nucleotides within the target DNA fragment adjacent to the adaptor. The sequence of such an adaptor-directed primer can vary, depending upon the specific adaptor used for the construction of the template and upon the number of arbitrary, selective nucleotides positioned at its 3'-end. Examples of DNA sequences and characteristics of oligonucleotides comprising both adaptor and adaptor-directed primers, each specific to the site generated by a particular restriction enzyme, are given in but not limited to Table I.

TABLE I

ADAPTOR AND PRIMER OLIGONUCLEOTIDES

| Double Strand Adaptor | Oligonucleotide Name | Sequence(5'→3')/SEQ ID No. | Length | Selective 3' nts | Tm (50 mM Salt) | %GC |
|---|---|---|---|---|---|---|
| Adaptor oligonucleotide components | | | | | | |
| biotin-Pst I-Ad | B-Pst.Ad.F | B-CTCGTAGACTGCGTACATGCA /17 | 21 | 0 | 49.2° C. | 52.40 |
| | Pst.Ad.R | 3'-CATCTGACGCATGT-5' /18 | 14 | 0 | 25.7° C. | 50.00 |
| biotin-Hnd III-Ad | B-Hnd.Ad.F | B-CTCGTAGACTGCGTACC /19 | 17 | 0 | 44.3° C. | 58.80 |
| | Hnd.Ad.R | 3'-CTGACGCATGGTCGA-5' /20 | 15 | 0 | 39.5° C. | 60.00 |
| Taq I-Ad | TAq.Ad.F | GACGATGAGTCCTGAC /21 | 16 | 0 | 40.8° C. | 56.20 |
| | TAq.Ad.R | 3'-TACTCAGGACTGGC-5' /22 | 14 | 0 | 35.1° C. | 57.10 |
| Sau-Ad | Sau.Ad.F | GGAATTCTGGACTCAGT /23 | 17 | 0 | 39.5° C. | 47.00 |
| | Sau.Ad.R | 3'-CCTTAAGACCTGAGTCACTAG-5' /24 | 21 | 0 | 47.3° C. | 47.60 |
| Mse-Ad | Mse.Ad.F | TGGCCTTTACAGCGTC /25 | 16 | 0 | 40.8° C. | 56.30 |
| | Mse.Ad.R | 3'-GAAATGTCGCACAT-5' /26 | 14 | 0 | 29.3° C. | 42.90 |
| Adaptor-directed primers | | | | | | |
| | Hnd.Ad.F | B-CTCGTAGACTGCGTACC /27 | 17 | 0 | 44.3° C. | 58.80 |
| | Hnd.pr.1 | CTGCGTACCAGCTTaca /28 | 17 | 3 -aca | 41.9° C. | 52.90 |
| | Hnd.pr.2 | CTGCGTACCAGCTTacc /29 | 17 | 3 -acc | 44.3° C. | 58.80 |
| | Hnd.pr.3 | CTGCGTACCAGCTTaac /30 | 17 | 3 -aac | 41.9° C. | 52.90 |
| | Hnd.pr.4 | CTGCGTACCAGCTTgtc /31 | 17 | 3 -gtc | 44.3° C. | 58.80 |
| | Hnd.pr.5 | CTGCGTACCAGCTTac /32 | 16 | 2 -ac | 40.8° C. | 56.20 |
| | Hnd.pr.6 | CTGCGTACCAGCTTaa /33 | 16 | 2 -aa | 38.2° C. | 47.05 |
| | Pst.Ad.F | B-CTCGTAGACTGCGTACATGCA /34 | 21 | 0 | 49.2° C. | 52.40 |
| | Pst.pr.1 | GACTGCGTACATGCAGac /35 | 18 | 2 -ac | 45.2° C. | 55.60 |
| | Pst.pr.2 | GACTGCGTACATGCAGaa /36 | 18 | 2 -aa | 42.9° C. | 50.00 |
| | Pst.pr.3 | GACTGCGTACATGCAGca /37 | 18 | 2 -ca | 45.2° C. | 55.60 |
| | Pst.pr.4 | GACTGCGTACATGCAGtt /38 | 18 | 2 -tt | 42.9° C. | 50.00 |
| | Pst.pr6 | GACTGCGTACATGCAGa /39 | 17 | 1 -a | 41.9° C. | 52.94 |
| | Pst.pr8 | GACTGCGTACATGCAGc /40 | 17 | 1 -c | 44.3° C. | 58.82 |
| | Taq.Ad.F | GACGATGAGTCCTGAC /41 | 16 | 0 | 40.8° C. | 56.20 |
| | Taq.pr.0 | ATGAGTCCTGACCGA /42 | 15 | 0 | 36.8° C. | 53.30 |
| | Taq.pr.1 | TGAGTCCTGACCGAacc /43 | 17 | 3 -acc | 44.3° C. | 58.80 |
| | Taq.pr.2 | TGAGTCCTGACCGAaca /44 | 17 | 3 -aca | 41.9° C. | 52.90 |
| | Taq.pr.3 | TGAGTCCTGACCGAcac /45 | 17 | 3 -cac | 44.3° C. | 58.80 |
| | Taq.pr.4 | TGAGTCCTGACCGAcaa /46 | 17 | 3 -caa | 41.9° C. | 52.90 |
| | Taq.pr.5 | ATGAGTCCTGACCGAg /47 | 16 | 1 -g | 39.5° C. | 60.00 |

TABLE I-continued

ADAPTOR AND PRIMER OLIGONUCLEOTIDES

| Double Strand Adaptor | Oligonucleotide Name | Sequence(5'→3')/SEQ ID No. | Length | Selective 3' nts | Tm (50 mM Salt) | %GC |
|---|---|---|---|---|---|---|
| | Taq.pr.6 | ATGAGTCCTGACCGAa /48 | 16 | 1 -a | 36.8° C. | 53.30 |
| | Taq.pr.7 | ATGAGTCCTGACCGAt /49 | 16 | 1 -t | 36.8° C. | 53.30 |
| | Taq.pr.8 | ATGAGTCCTGACCGAc /50 | 16 | 1 -c | 39.5° C. | 60.00 |
| | Taq.pr.9 | TGAGTCCTGACCGAac /51 | 16 | 2 -ac | 40.8° C. | 56.20 |
| | Taq.pr.10 | TGAGTCCTGACCGAaa /52 | 16 | 2 -aa | 38.2° C. | 50.00 |
| | Taq.pr.11 | TGAGTCCTGACCGAca /53 | 16 | 2 -ca | 40.8° C. | 56.20 |
| | Sau.Ad.F | GGAATTCTGGACTCAGT /54 | 17 | 0 | 39.5° C. | 47.10 |
| | Sau.pr.0 | GGAATTCTGGACTCAGTGATC /55 | 21 | 0 | 47.3° C. | 47.70 |
| | Sau.pr.1T | TTCTGGACTCAGTGATCt /56 | 18 | 1 -t | 40.6° C. | 44.40 |
| | Sau.pr.2TT | TCTGGACTCAGTGATCtt /57 | 18 | 2 -tt | 40.6° C. | 44.40 |
| | Sau.pr.3TTC | CTGGACTCAGTGATCttc /58 | 18 | 3 -ttc | 42.9° C. | 50.00 |
| | Mse.Ad.F | TGGCCTTTACAGCGTC /59 | 16 | 0 | 40.8° C. | 56.30 |
| | Mse.pr.1T | GCCTTTACAGCGTCTAAt /60 | 18 | 1 -t | 40.6° C. | 44.40 |
| | Mse.pr.2TC | CCTTTACAGCGTCTAAtc /61 | 18 | 2 -tc | 40.6° C. | 44.40 |
| | Mse.pr.3TCA | CCTTTACAGCGTCTAAtca /62 | 19 | 3 -tca | 41.6° C. | 42.10 |

A second type of primer used within the present invention corresponds in its 3' portion to a simple sequence repeat, or microsatellite, where the structure of the microsatellite is simple (simple SSR) as defined above. The simple microsatellite region can be tandem repeats of mono-, di-, tri-, tetra- or pentanucleotides. The 5' position of the primer contains 3 to 5 fully or partially degenerate nucleotides, which serve to anchor the primer adjacent to a microsatellite in the targeted genome. This primer can vary in length from 10 to 60 nucleotides, with a [G+C] content typically from 16% to 80%. Length polymorphism within a microsatellite locus between genomes is expected to be detectable using these primers, since in nearly all cases, primer extension is expected to initiate from a fixed site relative to the SSR target region. Primers similar to these are described by Zietkiewicz, E., et al., *Genomics*, 20, 176, (1994).

Another type of SSR-directed primer, uniquely utilized within the present invention, is the perfect compound SSR primer which is comprised of two different perfect SSR's that are immediately adjacent to one another with no intervening nucleotides either between the repeats or within each of the repeats. Perfect compound SSR primers are perfectly self-anchoring; that is, the simple SSR at the 5'-end of the primer serves as an efficient anchor for the adjacent 3' SSR from which primer extension proceeds (see FIG. 1c). It is intended, therefore, that primer extension initiates from a single, fixed site within a compound SSR target region. Any length variation between genomes in the portion of the target SSR across which primer extension occurs should be visible as length variation in the resulting amplification products from those genomes. The relative lengths of each constituent SSR within the compound primer can vary. However, Applicants have found that the best primer anchoring and greatest specificity for the target template is produced when the length of the 5' anchor is equal to or greater than that of the 3' priming portion.

For dinucleotide repeats, Applicants theorize that, excluding CG and GC combinations (long stretches of which are thought to be rare in eukaryotic genomes), 90 different permutations of two adjacent dinucleotide sequences are possible. As estimated by the following equation, $$[(4)(3)-2] \times [[(4)(3)-2-1] = 90,$$

the first (5'-most) constituent repeat may carry of any of the four nucleotides (A, G, C or T) in its first position, followed by any of the three remaining nucleotides at its second position, then from this product should be subtracted the two GC and CG combinations. For the second (3'-most) dinucleotide, the same calculation holds, but with the additional subtraction of the one combination occupying the first constituent dinucleotide repeat position. All of these 90 permutations are listed in Table II. Only 80 are true compound repeat sequences, however; 10 of the permutations are actually imperfect simple repeats (e.g., $(CT)_n(TC)_n$, $(AG)_n(GA)_n$, etc.). Similar calculations can be performed to estimate the number and types of different tri-, tetra- and pentanucleotide combinations possible by random nucleotide arrangements.

TABLE II

Permutations of Adjacent Dinucleotides: Occurrence in DNA Sequence Database

| COMPOUND, IN-PHASE Double Stranded Locus | Permutations 5' → 3' | Total, all data-bases | Pri-mate + human EST | Ro-dent | Other Mam-mal | Other Verte-brate | Inverte-brate | Bac-teria | Virus | Phage | Fungi | Plant | Cloned Soy-bean |
|---|---|---|---|---|---|---|---|---|---|---|---|---|---|
| 5'-(AC)x(AT)y-3'<br>3'-x(TG)y(TA)-5' | (AC)(AT),(CA)(TA)<br>(AT)(GT),(TA)(TG) | 79 | 28 | 27 | 5 | 2 | 8 | 0 | 0 | 0 | 5 | 4 | 22 |
| 5'-(AT)x(AC)y-3'<br>3'-x(TA)y(TG)-5' | (TA)(CA),(AT)(AC)<br>(TG)(TA),(GT)(AT) | 65 | 47 | 6 | 7 | 3 | 1 | 0 | 0 | 0 | 0 | 1 | 4 |
| 5'-(AG)x(AT)y-3'<br>3'-x(TC)y(TA)-5' | (AG)(AT),(GA)(TA)<br>(AT)(CT),(TA)(TC) | 0 | 0 | 0 | 0 | 0 | 0 | 0 | 0 | 0 | 0 | 0 | 1 |
| 5'-(AT)x(AG)y-3'<br>3'-x(TA)y(TC)-5' | (TA)(GA),(AT)(AG)<br>(TC)(TA),(CT)(AT) | 15 | 5 | 0 | 3 | 1 | 1 | 0 | 0 | 0 | 0 | 5 | 11 |
| 5'-(AC)x(AG)y-3'<br>3'-x(TG)y(TC)-5' | (AC)(AG),(CA)(GA)<br>(CT)(GT),(TC)(TC) | 83 | 40 | 41 | 2 | 0 | 0 | 0 | 0 | 0 | 0 | 0 | 3 |
| 5'-(AG)x(AC)y-3'<br>3'-x(TC)y(CG)-5' | (AG)(AC),(GA)(CA)<br>(GT)(CT),(TG)(TC) | 3 | 2 | 1 | 0 | 0 | 0 | 0 | 0 | 0 | 0 | 0 | 2 |
| 5'-(TG)x(AG)y-3'<br>3'-x(AC)y(TC)-5' | (TG)(AG),(GT)(GA)<br>(CT)(CA),(CA)(CT) | 221 | 98 | 43 | 71 | 2 | 4 | 0 | 2 | 0 | 0 | 1 | 5 |
| 5'-(AG)x(TG)y-3'<br>3'-x(TC)y(AC)-5' | (AG)(TG),(GA)(GT)<br>(CA)(CT),(AC)(TC) | 65 | 56 | 5 | 1 | 0 | 3 | 0 | 0 | 0 | 0 | 0 | 1 |
| | total occurrences | 531 | 276 | 123 | 89 | 8 | 17 | 0 | 2 | 0 | 5 | 11 | 49 |
| | # bp searched | 2.0E+08 | 3.3E+07 | 2.5E+07 | 6.7E+06 | 8.0E+06 | 2.2E+07 | 3.0E+07 | 2.2E+07 | 1.5E+06 | 3.1E+06 | >> | |
| | # sequences searched | 2.0E+05 | 3.5E+04 | 2.2E+04 | 6.2E+03 | 7.4E+03 | 1.3E+04 | 1.7E+30 | 1.8E+04 | 9.9E+02 | 1.8E+04 | >> | |

| COMPOUND, OUT-OF-PHASE Double Stranded Locus | Permutations 5' → 3' | Total, all databases |
|---|---|---|
| 5'-(AC)x(TA)y-3'<br>3'-x(TG)y(AT)-5' | (AC)(TA)<br>(TA)(GT) | 1 |
| 5'-(AC)x(GA)y-3'<br>3'-x(TG)y(CT)-5' | (AC)(GA)<br>(TC)(GT) | 7 |
| 5'-(AT)x(CA)y-3'<br>3'-x(TA)y(GT)-5' | (AT)(CA)<br>(TG)(AT) | 2 |
| 5'-(AT)x(GA)y-3'<br>3'-x(TA)y(CT)-5' | (AT)(GA)<br>(TC)(AT) | 2 |
| 5'-(AG)x(CA)y-3'<br>3'-x(TC)y(GT)-5' | (AG)(CA)<br>(TG)(CT) | 0 |
| 5'-(AG)x(TA)y-3'<br>3'-x(TC)y(AT)-5' | (AG)(TA)<br>(TA)(CT) | 0 |
| 5'-(CA)x(TC)y-3'<br>3'-x(GT)y(AG)-5' | (CA)(TC)<br>(GA)(TG) | 0 |
| 5'-(CT)x(AC)y-3'<br>3'-x(GA)y(TG)-5' | (CG)(AC)<br>(GT)(AG) | 7 |
| 5'-(AG)x(GT)y-3'<br>3'-x(TC)y(CA)-5' | (AG)(GT)<br>(AC)(CT) | 2 |
| 5'-(TG)x(GA)y-3'<br>3'-x(AC)y(CT)-5' | (TG)(GA)<br>(TC)(CA) | 3 |
| 5'-(GT)x(TA)y-3'<br>3'-x(CA)y(AT)-5' | (GT)(TA)<br>(TA)(AC) | 0 |
| 5'-(AT)x(TG)y-3'<br>3'-x(TA)y(AC)-5' | (AT)(TG)<br>(CA)(AT) | 1 |
| 5'-(CT)x(TA)y-3'<br>3'-x(GA)y(AT)-5' | (CT)(TA)<br>(TA)(AG) | 0 |
| 5'-(AT)x(TC)y-3'<br>3'-x(TA)y(AG)-5' | (AT)(TC)<br>(GA)(AT) | 0 |
| 5'-(GT)x(TC)y-3'<br>3'-x(CA)y(AG)-5' | (GT)(TC)<br>(GA)(AC) | 1 |
| 5'-(CT)x(TG)y-3'<br>3'-x(GA)y(AC)-5' | (CT)(TG)<br>(CA)(AG) | 0 |
| | total occurrences | 26 |

| double stranded locus | permutations 5' → 3' | |
|---|---|---|
| COMPOUND, NONPALINDROMIC, NO SHARED NTS BETWEEN REPEATS | | |
| 5'-(GA)x(CT)y-3'<br>3'-x(CT)y(AG)-5' | (GA)(CT)<br>(AG)(TC) | 0 |
| 5'-(CT)x(GA)y-3'<br>3'-x(GA)y(CT)-5' | (CT)(GA)<br>(TC)(AG) | 0 |
| 5'-(CA)x(GT)y-3'<br>3'-x(GT)y(CA)-5' | (CA)(GT)<br>(AC)(TG) | 0 |

TABLE II-continued

Permutations of Adjacent Dinucleotides: Occurrence in DNA Sequence Database

| | | |
|---|---|---|
| 5'-(GT)x(CA)y-3' | (GT)(CA) | 2 |
| 3'-x(CA)y(GT)-5' | (TG)(AC) | |
| | total occurrences | 2 |
| | COMPOUND, PALINDROMIC, NO SHARED NTS BETWEEN REPEATS | |
| 5'-(GA)x(TC)y-3' | (GA)(TC) | 0 |
| 5'-(AG)x(CT)y-3' | (AG)(CT) | 0 |
| 5'-(TC)x(GA)y-3' | (TC)(GA) | 0 |
| 5'-(CT)x(AG)y-3' | (CT)(AG) | 0 |
| 5'-(CA)x(TG)y-3' | (CA)(TG) | 0 |
| 5'-(AC)x(GT)y-3' | (AC)(GT) | 1 |
| 5'-(TG)x(CA)y-3' | (TG)(CA) | 0 |
| 5'-(GT)x(AC)y-3' | (GT)(AC) | 1 |
| | total occurrences | 2 |
| | NOT COMPOUND; IMPERFECT SIMPLE REPEATS | |
| 5'-(CA)x(AC)y-3' | (CA)(AC) | 13 |
| 3'-x(GT)y(TG)-5' | (GT)(TG) | |
| 5'-(AC)x(CA)y-3' | (AC)(CA) | 18 |
| 3'-x(TG)y(GT)-5' | (TG)(TG) | |
| 5'-(GA)x(AG)y-3' | (GA)(AG) | 4 |
| 3'-x(CT)y(TC)-5' | (CT)(TC) | |
| 5'-(AG)x(GA)y-3' | (AG)(GA) | 9 |
| 3'-x(TC)y(CT)-5' | (TC)(CT) | |
| 5'-(AT)x(TA)y-3' | (AT)(TA) | 20 |
| 3'-x(TA)y(AT)-5' | (TA)(AT) | |
| | total occurrences | 64 |

Note: x, y ≧ 6 for all dinucleotide combination searches

The complete GenBank DNA sequence databases (version 84.0) were searched using the FindPatterns search algorithm within the University of Wisconsin Genetics Computer Group sequence analysis package (version 7.3). The individual strands of the double stranded sequences shown in the first column were used individually as queries either against the entire GenBank database (all species combined) or against the separate subdatabases representing the indicated phylogenetic groupings. For each query, such as $(AC)_x(AT)_y$, x and y were each designated to be ≧6; that is, any hit in the database was required to carry at least 6 units of each of the two constituent dinucleotide repeats. The final column designates the number of matches to the respective query within an in-lab collection of cloned soybean SSR sequences (unpublished data), isolated as small inserts containing either $(AC)_x$ or $(AG)_y$ sequences.

Although all 80 compound dinucleotide sequences have the potential to exist in a genome and to serve as targets for corresponding primers, only a small subset of these adjacent dinucleotide repeat combinations has been observed to occur at a reasonable frequency among compound SSRs represented within the DNA sequence databases and among SSRs cloned and sequenced from plant and animal genomes (see Table II). The great majority of these 80 total combinations occur at surprisingly low relative frequencies in eukaryotic genomes.

Nearly all of the compound repeats in this high frequency subset have perfect nucleotide periodicity whereby the two adjacent constituent dinucleotide repeats share a common nucleotide that retains a constant periodic spacing across the junction and the entire compound structure. These compound SSR sequences are designated by Applicants as "in-phase", and include repeats such as $(AT)_x(AG)_y$, $(AC)_x(TC)_y$, and $(AT)_x(GT)_y$ where x and y independently are ≧2 and can be multiples of 0.5. Thirty-two of the 80 possible dinucleotide combinations fall into this in-phase category, and these are listed in Table II. All the remaining compound repeats are termed, "out-of-phase". The 32 individual in-phase compound sequences (excluding CG and GC), however, represent only 16 unique nonredundant single-stranded sequences. The 2-fold redundancy derives from the possibility of positioning the repeating in-phase nucleotide as either the first or the second base in the core repeats (i.e., $(AC)_x(AT)_y$ and $(CA)_x(TA)_y$, although nonidentical as individual primers, represent the same compound sequence). In addition, these 16 canonical, nonredundant sequences represent the complementary strands of only 8 individual double-stranded compound repeat loci (see Table II). In other words, a compound dinucleotide repeat as a locus in double stranded DNA could be recognized by any of four different single stranded oligonucleotide primers, out of the total set of 32 possible permutations. For example, a locus $(AT)_6(AG)_6$, is a target site for the four hypothetical primers, $(AT)_x(AG)_y$ $(TA)_x(GA)_y$ $(CT)_x(AT)_y$, and $(TC)_x(TA)_y$ (with x, y≦6).

By chance alone, and assuming no nucleotide bias in a source genome, each of the 80 different perfect compound dinucleotide permutations would be expected to occur in the genome at equal frequencies. As mentioned above, however, it was already discovered by Applicants that the in-phase subset are more abundant compared to the out-of-phase set. Further, the two possible permutations of the constituent repeats for some of the in-phase compound sequence combinations appear to be represented at widely differing frequencies in a given genome. For example, the compound repeat, $(AT)≦_6$ $(AG)≦_6$ appears to be at least 5 times more abundant in plant genomes than its permutant counterpart, $(AG)≦_6$ $(AT)≦_6$; and, $(AC)≦_6$ $(AG)≦_6$ is much more abundant in primate genomes than $(AG)≦_6$ $(AC)≦_6$. Both from a systematic analysis of cloned sequence databases and from an empirical examination of both plant and animal genomes, these few, most frequently occurring compound dinucleotide repeats are known by Applicants and therefore are fully predictable. This knowledge serves to reduce to only a few the number of different compound SSR primers that will be successful for producing an adequate number of SSR-to-adaptor co-amplification products using the present invention.

Thus, of the 80 total compound dinucleotide sequence permutations that are possible by random arrangement of nucleotides, only a few (nearly all of which are in-phase) are present in plant and animal genomes at a measurable frequency, and only these few, therefore, are required to detect a large proportion of the compound SSR loci present in any given genome. Experimental data demonstrate, however, that specific primers representing these 16 compound sequences are not equally effective at recognizing and priming from the respective target locus. Such differences in primer efficiency were determined empirically to result from each constituent repeat's base composition (AT-richness), in combination with the relative position (5' anchoring versus 3'-priming) of each constituent repeat within the primer.

Table II also lists the dinucleotide permutations for which the spacing of a shared nucleotide is not preserved (termed, "out-of-phase") or for which no nucleotide is shared between the two constituent repeats. The latter category contains dinucleotide combinations that are both palindromic and nonpalindromic. Although not nearly as frequent in eukaryotic genomes as the in-phase sequences, some of the out-of-phase compound SSR sequences nonetheless appear to be present in most genomes. Therefore, primers that correspond to such out-of-phase repeats also are expected to serve as initiation sites for primer-extension from their respective target loci in the genome. Preferred anchored primers of the instant invention where primer nucleotide periodicity is not specifically designated may be defined by formula I for dinucleotide repeats:

Formula I $$5'\text{-}(XY) \leq_{15} (NM) \leq_{15}\text{-}3'$$

where X=A, C, T, or G; Y=A, C, T, or G; X__Y N=A, C, T, or G; M=A, C, T, or G; N__M and where XY≠NM Herein, these are abbreviated as (XY)#(NM)# and by formula II for trinucleotide repeats:

Formula II $$5'\text{-}(XYZ) \leq_{10} (LMP) \leq_{10}\text{-}3'$$

where X=A,C,T, or G; Y=A,C,T, or G; Z=A,C,T, or G and X, Y, Z are not the same single base;

where M=A,C,T, or G; N=A,C,T, or G; P=A,C,T, or G and M, N, P are not the same single base;

and where XYZ≠NMP

Generally the primers of formulae I and II will consist of oligonucleotides of 10–60 nucleotides in length that contain two different, constituent simple sequence repeats that are directly adjacent to one another, with no intervening non-repeat nucleotides. From the 5' end, this oligonucleotide contains a simple sequence repeat of up to 15 repeat units in length, followed immediately 3' by a second simple sequence repeat that is also up to 15 repeat units in length.

Preferred anchored primers of the instant invention where primer nucleotides are specifically designated to be in-phase may be defined by the formula III for dinucleotide repeats:

Formula III:

This formula describes a subset of sequences covered broadly by Formula I.

$$5'\text{-}(XY) \leq_{15} (XZ) \leq_{15}\text{-}3' \text{ or } 5'\text{-}(YX) \leq_{15} (ZX) \leq_{15}\text{-}3'$$

where X=A,C,T, or G; Y=A,C,T, or G; Z=A, C,T, or G but where Y≠X; Z≠X; and Y≠Z

Herein, these are abbreviated as (XY)#(XZ)# or (YX)#(ZX)#.

Typically oligonucleotides of formula III are 10–60 nucleotides in length and contain two different, constituent simple sequence repeats that are directly adjacent to one another, with no intervening nonrepeat nucleotides. From the 5' end, this oligonucleotide contains a simple sequence repeat of up to 15 repeat units in length, followed immediately 3' by a second simple sequence repeat that is also up to 15 repeats. Each repeat shares a common nucleotide, which is retained at a consistent periodicity across both constituent repeats, occupying either the first or the second position within each repeat.

In an especially preferred embodiment of Applicants' invention, PCR amplification to detect polymorphisms is carried out using restriction fragmented DNA modified with appropriate adaptors, wherein the primer pair used is comprised of one primer which is of the first type described above (Zabeau EP 534,858; an AFLP primer) and the second primer is one of Applicants' unique perfect compound SSR primers described above.

One of skill in the art will also appreciate that Applicants' unique compound SSR primers can also be used in conjunction with a variety of other primer types which include for example, non-adaptor primers, primers of fixed sequence, arbitrary primers or any primer that might hybridize with currently known or unknown dispersed repeated sequences in the genome. An example particularly suited to the present invention would be where the other primer is of completely arbitrary sequence such as a RAPD primer (Williams et al., Nucleic Acids Res. 18, 6531, (1990)).

RAPD primers have been used to generate polymorphic markers from the amplification of genomic DNA. Preferably the nucleotide sequence of the RAPD primers would be about 9 to 10 bases in length, between 50 and 80% G+C in composition and contain no palindromic sequences. Amplifications using RAPD primers alone are typically done using short primers and low annealing temperatures which maximizes the probability that several randomly distributed loci on the genome will produce amplification products. Because the incidence of any particular RAPD binding site within the genome is relatively low, this methodology would serve to restrict the amount of the genome that is subject to amplification with any particular primer combination. It is contemplated that the selectivity of the RAPD methodology would serve an enrichment function, similar to the selection function provided by use of a biotinylated adaptor in the conventional AFLP method to enrich for only a subset of randomly distributed genomic regions, from which a manageable number of co-amplification could then occur.

Preparation of Genomic DNA Restriction Digested Fragments:

Target DNA useful for amplification in the present invention was comprised of restriction fragments generated from Taq I+Pst 1 or Taq I+HindIII digestion of eukaryotic genomic DNA, further modified by the ligation of specific adaptor sequences. Genomic DNA was isolated from soybean and corn using either the CTAB/chloroform extraction and CsCl/centrifugation method of Murray and Thompson (Murry et al., *Nuc. Acid Res.*, 8, 4321, 1980) or a urea extraction miniprep procedure (Chen et al., *The Maize Handbook*, M. Freeling and V. Walbot, eds., (1993) pp 526–527, New York). Mammalian and salmon genomic DNAs were purchased from commercial sources (Sigma (St. Louis, Mo.); Clontech (Palo Alto, Calif.)). Genomic DNA was prepared for amplification reactions by complete restriction endonuclease digestion followed by ligation of site-specific double-stranded adaptors. Methods for this type of adaptor design and construction are well known in the art, and examples are given by Zabeau, EP 534,858.

It is preferred if a combination of two different restriction enzymes having 4-bp and 6-bp recognition sites, respectively, are used for the preparation of target DNA. Examples of suitable restriction enzymes are Taq I and Pst I however, any restriction enzymes having 4-, 5-, 6- or even 8-bp recognition sites also are appropriate providing their activities are not inhibited by target site DNA methylation or other non-mendelian mechanisms of selective nucleotide modification. Any combination of such restriction enzymes are potentially suitable. Other restriction enzymes suitable for the present invention may include but are not limited to the hexanucleotide site enzymes, EcoRI, DraI or BamHI, the tetranucleotide stie enzymes, Sau 3AI, MboI, MseI, Tsp509I or AluI, the pentanuleotide site enzymes HinfI or AvaII, and the octanucleotide site enzymes, PmeI, PacI, or SwaI.

Genomic DNA is digested with a first enzyme such as Taq I, followed by further digestion with a second enzyme such as Pst I, according to standard protocols, such as that given by Zabeau (EP 534,858). The digestions generated from each input genomic DNA are a mixture of symmetric fragments, bordered at both ends by either Taq I or Pst I sites, and asymmetric fragments, each flanked by a Taq I site and a Pst I site.

Adaptors:

Double stranded adaptors are generated by annealing the two partially complementary single stranded component oligonucleotides of each pair (examples are listed in Table I). Since restriction endonucleases cleave genomic DNA molecules at specific sites, amplification of restriction fragments can be achieved by first ligating synthetic oligonucleotide adaptors to the ends of restriction fragments, thus providing all restriction fragments with two common flanking tags which will serve as anchor bases for the primers used in PCR amplification. Typically, restriction enzymes either produce flush ends on a DNA fragment, such that the terminal nucleotides of both strands are base paired, or generate staggered ends in which one of the two strands protrudes to give a short (1–4 nt) single strand extension. In the case of restriction fragments with flush ends, adaptors are used with one flush end. In the case of restriction fragments with staggered ends, adaptors are used that have a single stranded extension complementary to the single stranded extension on the restriction fragment. Consequently, each type of restriction site end is specifically recognized by a particular adaptor by virtue of the complementarity of the matched ends. In addition, the DNA sequence of the entire length of each adaptor type differs from that of other adaptor types (see Table I). Typically, the adaptors used are comprised of synthetic single-stranded oligonucleotides which are in part complementary to each other, and which are usually approximately 10 to 30 nucleotides long, preferably 12 to 22 nucleotides long, and which form double stranded structures when mixed together in solution. Using the enzyme T4 DNA ligase, the adaptors are joined covalently and specifically to the complementary ends of individual DNA molecules in the mixture of restriction fragments generated from a particular genomic DNA source. Using a large molar excess of adaptors over restriction fragments ensures that all restriction fragments will receive adaptors at both ends. These adaptors are not usually phosphorylated. These ligated adaptors then serve as templates for the adaptor-directed PCR primers.

In one embodiment of the invention, all restriction fragments from the genome carry the same adaptor at both ends, and a single PCR primer corresponding to that adaptor sequence can be used to amplify simultaneously from the fragments. The simultaneous amplification of several different restriction fragments is often referred to as multiplex PCR amplification. Since in such a case all restriction fragments are bordered at both ends by the same adaptor, it is obvious that primer extension and PCR amplification of a mixture of tagged restriction fragments will amplify all restriction fragments in a synchronous fashion. In another embodiment using two or more different restriction enzymes to cleave the DNA, two or more different adaptors are ligated to the ends of the restriction fragments. In this case, two different PCR primers, each matching the sequence of a particular adaptor, can be used for exponential amplification from a subset of the restriction fragments. In one preferred embodiment using two or more restriction enzymes, both adaptors are unmodified, and the fragment mixture is enriched using a pre-amplification step. In another preferred embodiment using two or more restriction enzymes, the adaptor corresponding to one of the restriction enzyme site ends is covalently linked to a biotin molecule. Using standard methods for isolating biotinylated molecules, this design allows for the selection, from a complex mixture of restriction fragments, of only those bordered on one or both ends by a biotinylated adaptor. Both of the two possible selection steps reduces the complexity of the starting mixture of restriction fragments and constitutes an enrichment step prior to the PCR amplification, thereby reducing in certain instances the background of fragments with same-site ends. In yet another embodiment one of the amplification primers may be radiolabeled for identification of the products via autoradiography, or may be modified with fluorescent tags for fluorescence detection of products. Methods of labeling nucleic acids and suitable labels are well known in the art (see Sambrook supra). For example a radioisotope suitable in the present invention is $^{33}$Phosphate, incorporated at the 5' end of one strand of the adaptor by a phosphate group transfer from of $[\gamma\text{-}^{33}\text{P}]$ATP under kinasing conditions.

Double stranded adaptors (with or without biotin labels) are generated by annealing the two partially complementary single stranded component oligonucleotides of each pair (listed in Table I). For example,the double stranded Taq I adaptor (Taq-Ad) is produced by combining the single-stranded Taq.AdF and Taq.AdR oligonucleotides under favorable annealing conditions. To generate the biotinylated double stranded Pst I adaptor (biotin-Pst-Ad), the single stranded oligonucleotides biotin-Pst.AdF and Pst.AdR similarly are combined. If restriction enzymes other than those listed in Table I are used, then the adaptors must be designed to carry the appropriate protruding single-stranded-ends for a given restriction ½-site. In a preferred embodiment, each adaptor contains a single base alteration within the restriction half-site it carries, so that the reconstructed site generated by each ligation event cannot be re-digested. Therefore, the artisan will appreciate that it is possible that restriction digestion and ligation can be performed simultaneously under the appropriate buffer and temperature conditions.

Dna Amplification

Although the basic protocols for the amplification of nucleic acids are well known in this art, significant modifications of those protocols were necessary in order to achieve optimal amplification of DNA fragments and detection of polymorphic products. Several factors were found to significantly influence these amplifications, including variation in the thermocycling parameter of the PCR protocols, variation in the labeling of the primers, and the length and nucleotide composition of the primers.

Thermocycling Variation in PCR:

The efficiency of amplification by both 5'-anchored simple and compound SSR primers was tested on soybean, corn, and mammalian templates, using thermocycling profiles having either constant temperature or touchdown annealing conditions. Both the adaptors and the SSR-directed primers in these amplifications were designed to have $T_m$'s within a relatively narrow range (38–45° C. in 50 mM Na or K salt), so that any primer pair chosen for an amplification would have approximately the same optimal annealing temperature.

Three different constant annealing temperatures, 52° C., 58° C. and 60° C. were tested using a standard 3-step per cycle protocol. Although the results from each test varied from the others (the higher the temperature, the fewer the products generated), it is clear that the efficiency of primer discrimination at most target loci was found to be unacceptably inefficient at any of these constant annealing temperatures. Every "product" from these amplifications was represented by a small family of bands, and the products within each family differed by multiples of two; the length of each dinucleotide repeat. However, this "stuttering" effect and potential nonspecific product formation was minimized when a touchdown thermocycling protocol (Don, et al., *Nuc Acids Res*, 19, 4008 (1991)) was used. In touchdown amplification, the annealing temperature begins deliberately high, then is incrementally lowered in successive cycles, down to a desired, "touchdown" annealing temperature. Touchdown temperatures of 59° C., 58° C. and 56° C. were tested for some primer combinations. For most SSR-directed primers, the 56° C. final touchdown conditions produced the greatest number of specific, non-stuttering bands. For the purpose of the present invention, therefore, it is most preferred if nucleic acid amplification be conducted according to a touchdown protocol where 56° C. is the optimal final annealing temperature. However, depending on the actual composition of the primers, a particular amplification may involve final annealing temperatures of 55° C.–60° C.

Another variable in the thermocycling protocol that was explored is the method by which the amplification reactions are initiated. Typical PCR amplification protocols initiate with a cold start; all reagents necessary for DNA amplification are present in the reaction mixture prior to the first denaturation step. In contrast, a hot start protocol calls for the exclusion of one key reaction component, typically either the primer, nucleotides or polymerase, from the mixture during reaction setup and the first denaturation. This component then is added following denaturation, and primer extension can proceed.

The cold start protocol allows for the possibility that primers will anneal under nonstringent conditions both to template sites that are not necessarily a perfect match, and to multiple, staggered sites within a target locus. Often this method leads to a stuttering effect of the amplification products on the gel. In contrast a hot start protocol prevents spurious primer annealing to incorrect template sites at ambient temperatures prior to the first denaturation, and generates products that resolve more sharply and discretely on the gel. When otherwise identical amplification reactions were performed using the cold start and hot start protocols, it was found that for nearly every 5'-anchored simple SSR-directed primer, a cold start produced unacceptably indistinct products on the gel. Much sharper products were generated using hot start. In contrast, product resolution was found to be more consistent between cold and hot start methods when using compound SSR primers. In spite of the potential drawbacks in product resolution, cold start amplification was easier to perform, particularly when processing large numbers of samples, and was routinely found to be sufficient to generate amplification products that could be distinguished as polymorphic between genomes. Therefore, a slight gain in product resolution is sacrificed in a cold-start protocol in exchange for greater speed and ease of reaction setup. If 5'-anchored simple SSR primers are used, a hot-start is preferred, but a cold-start is adequate and sufficient for amplification reactions involving most compound SSR-directed primers.

Choice of Primer Labeling:

The complementary strands of a duplex DNA molecule usually resolve independently to slightly different positions on a denaturing polyacrylamide gel. If both strands of a DNA duplex are radiolabeled, then the autoradiograph will show a separate band representing each strand of each amplification product. Resolution of only a single band for each amplification reaction product on the denaturing polyacrylamide gel requires that only one strand of each product be labeled. To achieve this, only one of the two primers in any given pair used for an amplification reaction should be labeled. Either $^{32}$P or $^{33}$P can be used as radiolabels, although $^{33}$P images are generally sharper on an autoradiograph. Alternatively, a variety of different fluorophores can be incorporated into the primer; the resulting products can then be detected using a fluorescence detection system.

The effects of radiolabeling the SSR primer, in comparison to the alternate labeling of the adaptor-directed primer, were explored. In all protocol variations, radiolabeling the adaptor-directed primer resulted in significant background. Generally, the lanes on the gel contained a few discrete bands, but the major result in every case was a smear of products distributed along the entire length of the lane. In contrast, when only the SSR-directed primer was labeled in the amplification reactions, the products were much more discrete on the autoradiograph and not associated with any significant lane background. This difference likely results from the high abundance of adaptor target sites on a large proportion of the template fragments (from which even linear amplifications with labeled primers collectively will lead to significant backgrounds). In contrast, the labelled SSR primers have far fewer target sites in the template mixture, and most become part of a productive, exponential amplification. Hence 5'-labeling of only the SSR primer is preferred, and would apply to labeling with either radioactive or fluorescent tags.

Variations in SSR and Adaptor Primer Design:

Variability in the SSR-to-adaptor amplification reaction, and therefore in the products obtained, results not only from the reaction and thermocycle setup conditions described above but also from subtleties in the design of the primers used in these amplifications. Once a particular compound SSR has been chosen as the target locus sequence for this assay, then either partially or entirely different sets of amplification products can still be controlled by altering any one of the following primer design criteria:

a) the number and base composition of the 3'-extension nucleotide(s) on the adaptor-directed primer;

b) the relative lengths of the two constituent simple repeats that comprise the compound SSR primer;

c) the particular strand of the double-stranded compound SSR locus chosen to correspond to the single-stranded primer (i.e., the directionality of the primer);

d) choice of restriction enzymes and SSR targets for a particular genome.

a) Length of the Adaptor-Directed Primer:

An adaptor-directed amplification primer which corresponds to the sequence of one of the synthetic adaptors ligated to the restricted ends of the genomic DNA can carry a variable number of arbitrary sequence nucleotides (zero to ten) at its 3'-end. These variable 3'-nucleotides on the primer anneal specifically to sequences that are directly adjacent to the adaptor and restriction site and whose sequences are not known, a priori, on any particular genomic restriction fragment. The recognition of each such primer to only a subset of all possible fragments in the template mixture provides exquisite specificity in the amplification reaction (Zabeau, EP 534,858). Such primers, otherwise identical in sequence except for differences in the few 3'-most nucleotide(s), can amplify completely nonoverlapping sets of amplification products and behave much like allele-specific amplification primers (Newton et al., (1989) *Nuc. Acids Res* 17: 2503; Kwok et al., (1990) *Nuc. Acids Res.* 18: 999; Wu et al., (1989) *Proc. Natl. Acad. Sci. USA* 86: 2757). The key difference, however, is that use of these adaptor-directed primers requires no prior sequence knowledge of the genomic locus to be amplified, and each primer will selectively co-recognize multiple target sites in a template DNA mixture.

In general, the longer the variable 3'-extension, the more selective or restrictive the primer. This 3'-extension contains arbitrary, nondegenerate or partially degenerate bases, which restrict annealing of the primer to only a subset of the total number of potential target sites, thus leading to a reduction in the real number of co-amplified products. The addition of each nondegenerate nucleotide onto the 3'-extension leads hypothetically to 4-fold greater template discrimination. In addition, different single nucleotides at the 3'-most base position(s) confer unique template specificities to otherwise identical primers. Thus, varying both the number and composition of the 3'-selective nucleotides on the adaptor-directed primer is sufficient to generate individual, either partially or completely, nonoverlapping sets of amplification products from the same template when paired with a given SSR-directed primer. The choice of which 3'-extension to use for a particular amplification is largely a matter of chance, but still will depend largely upon relative nucleotide frequencies in a target genome and upon the abundance in the genome of the specific SSR that serves as the other priming site.

b) Relative Lengths of the Two Constituent Simple Repeats Comprising the Compound SSR Primer:

Every simple and compound SSR locus in the genome is a double stranded structure whose individual strands carry different permutations of nucleotides. Unless the core dinucleotides of a compound repeat are palindromic (e.g., $(CA)_x(TG)_y$ or $(AG)_x(CT)_y$), a single-stranded primer that may specifically anneal to one strand at a particular SSR locus will not anneal to the opposite strand. None of the in-phase compound SSRs is palindromic and only 8 of the 90 possible dinucleotide permutations represents such a palindrome. Therefore, all in-phase and most out-of-phase SSR-directed primers will primer-extend from each genomic target locus in a polar, unidirectional manner, and any compound SSR locus can be recognized and amplified from by any of four primer classes. For example, the compound in-phase SSR locus, can be recognized by four different canonical primer classes:

$$5'-(AC)_x(AT)_y-3',$$

$$5'-(CA)_x(TA)_y-3',$$

$$5'-(AT)_x(GT)_y-3',$$

and $$5'-(TA)_x(TG)_y-3',$$

where the 5'-most repeat in each serves primarily to anchor the primer to the template, and the 3'-most repeat serves a primer-extension function (see FIG. 1c).

Each of these four canonical primer classes can include a wide range of individual primers, all differing by the length of the two constituent repeats within the primer. Changes in the lengths of these constituent repeats have profound effects on primer efficacy and the fidelity of reproducible amplifications. In general, the longer the 5'-anchoring repeat (i.e., the value of x, above) relative to that of the 3'-priming repeat (the value of y), the better the primer's specificity and priming efficiency in the amplification. In addition, only a primer with a short 3' repeat will allow amplification from compound SSR loci containing very short downstream repeats. compound SSR loci containing very short downstream repeats.

c) Polarity of the Single Stranded Compound SSR-Directed Primer:

The choice of which strand of a double-stranded compound SSR locus to use as a primer can be extremely critical for determining the success of the SSR-to-adaptor amplification reaction. It should be noted that the only type of (AT)-containing primer that will lead to efficiently generated amplification products under standard conditions is one in which the $(AT)_n$ sequence is very short (1.5–3 repeat units) and is situated as the 3'-primer extension end. An $(AT)_n$ repeat of any length at the 5' end is completely inefficient as an anchor, and results in little or no amplification from a complex genomic template mixture.

d) Restriction Site Frequencies, Nucleotide Bias, SSR Frequencies, and Primer Design Considerations:

Ligation products carrying biotinylated adaptors may be selected out of each digestion/ligation mixture using a streptavidin or avidin coated support such as paramagnetic beads, as provided by Dynal Inc.,(Lake Success, N.Y.). This selected DNA does not have to be purified further from the beads for the subsequent amplifications. In one embodiment where two restriction enzymes are used and only the adaptor corresponding to the restriction enzyme with the hexanucleotide site is biotinylated, the selected DNA is a mixture of fragments bordered only by one or the other restriction site or flanked at each end by different sites. For example, if Taq I and Pst I are used, then only the Pst I adaptor is biotinylated. Following biotin selection, the Taq I-Pst I and Pst I-Pst I fragments are predicted to be present in the enriched fragment mixture at an approximate ratio of 30:1, respectively. All Taq I-Taq I fragments are effectively discarded. Methods for such a calculation will be apparent to one skilled in the art, for example: if the frequency of each nucleotide is known for the specific genome, then the symmetric and asymmetric restriction fragments will be present in the digestion mixture at predictable proportions.

```
5'-CACACACACACACACACACACACATATATATATATATATATA-3'   SEQ ID NO.:1

3'-GTGTGTGTGTGTGTGTGTGTGTGTATATATATATATATATAT-3',  SEQ ID NO.:2
```

In general, a calculation can be made that derives from the following assumptions:

First, recognition sites for each restriction enzyme are present in the genome at differing absolute frequencies, which are a function of the number of nucleotides in the site and of the genome's nucleotide composition. Second, these absolute frequencies can be converted to relative frequencies, p and q, since the sum of the relative frequencies (p+q) is always equal to 1. For example (considering equal nucleotide frequencies and random nucleotide distribution in a genome):

| site | absolute frequency | relative frequency |
| --- | --- | --- |
| Taq I | $(0.25)^4 = 3.9 \times 10^{-3}$ | p = 0.9412 |
| Pst I | $(0.25)^6 = 2.44 \times 10^{-4}$ | q = 0.0589 |

Finally, the relative frequencies of restriction fragments bordered by these sites are simply the products of the relative site frequencies for each fragment type. Therefore:

| fragment | relative frequency |
| --- | --- |
| Taq I-Taq I | $p^2 = 0.8862$ |
| Pst I-Pst I | $q^2 = 0.0035$ |
| Taq I-Pst I and Pst I-Taq I | $2pq = 0.1109$ |

Therefore in this embodiment, utilizing restriction enzymes with 4- and 6-bp recognition sites and assuming no nucleotide bias, the biotin-selected DNA fragments represent only 11.1% of the genome. Different restriction enzymes with different site frequencies will lead to a greater or lesser proportion of the genome represented in the mixture of selected fragments. Using several restriction enzyme combinations will ensure better coverage of the genome than just a single enzyme combination.

The selected DNA fragments may be used as a pooled template mixture for polymerase chain reaction amplifications using one each of a primer corresponding to one of the adaptors (the one that was not biotinselected) and a primer directed to a particular 5'-anchored simple or compound SSR sequence. One skilled in the art will appreciate that a detectable product will result from any single genomic template fragment only when exponential amplification occurs between the adaptor-directed primer and an oppositely oriented SSR-directed primer (see FIG. 1a). Multiple amplification products are expected from each template DNA mixture since the SSR and adaptor sequences are not single-copy sites. The multiplex ratio (the number of co-amplified products) of each amplification reaction is affected by the absolute genomic copy number of a specific SSR sequence, and can be adjusted experimentally for a given SSR by altering either the level of degeneracy of a simple SSR primer's 5'-anchor or the number and quality of the nondegenerate selective nucleotides at the 3' end of the adaptor-directed primer. For example, assuming equal frequencies for all four nucleotides in the genome, the addition of each successive nondegenerate nucleotide onto the 3'-end of the adaptor-directed primer leads to a 4-fold reduction in the number of co-amplified products from a given template mixture (see FIG. 1b). Therefore, an adaptor primer carrying zero selective nucleotides at its 3' end (eg., Taq.AdF; see Table I) will co-amplifiy 4 times as many templates as will a primer with a single, nondegenerate 3'-nucleotide (e.g., Taq.pr6, whose 3'-extension is -A). Similarly, this primer will co-amplify 4 times as many template fragments as a primer carrying 2 selective nucleotides, and so on. In general, the degree of selectivity of the adaptor-directed primer can be estimated using the formula, $\frac{1}{4}^{2n}$, where n=the number of selective bases. It should be cautioned that although convenient, this simplified calculation does not take into account the base composition of the genome, nor of the recognition sites of the restriction endonucleases used to produce the genomic fragments.

1. Although most DNA fragments in the bead-selected or pre-amplified mixture should be bordered at one end by the adaptor corresponding to the adaptor-directed primer to be used in the PCR, only a subset of these fragments are expected to carry an internal simple sequence repeat region complementary to a particular SSR primer. Thus, amplification products will be generated and detected only from the subset of target molecules that not only are flanked by the primer-specific adaptor but also contain an internal repeat sequence matching the SSR primer. It should be noted that absolute frequencies for the different repeats can vary widely within a species and are not accurately known for most plant genomes. Preliminary studies indicate that in soybean, $(AT)_n$ is at least twice as abundant as $(CT)_n$, which in turn appears to be somewhat more frequent than $(CA)_n$ (Morgante & Olivieri, Plant J 3. 175 (1992); Akkaya et al., (1992) Genetics, 132:1131). In general, it is estimated that one SSR longer than 20 bp exists in plant genomes once every 23–29 kb, compared to a figure of 6 kb in mammals (Wang et al., Theor. Applied Genetics: 88, 1 (1994); Morgante & Olivieri, Plant J (1993); Beckmann & Weber Genomics 12.627 (1992)). Frequencies of compound SSR sequences, however, have not been documented in the literature.

A completely degenerate 5'-anchor on a simple SSR primer should prime from every locus in the genome that carries that particular SSR sequence. Any degree of nondegeneracy introduced into the anchor will reduce the potential number of genomic target sites, and therefore the number of amplified fragments. In a genome with no nucleotide bias, the complexity of the co-amplified products is reduced by a factor of 4 for every anchor position that is assigned a nondegenerate nucleotide. Each self-anchoring compound SSR primer is expected to anneal and prime from every matching compound SSR locus in the biotin-selected fragment mixture (providing each target SSR locus has a sufficient length to allow complete hybridization by the primer).

Detection of Polymorphisms Between Phenotypically Related Individuals:

Individual gel banding pattern differences of the co-amplified fragments between different templates (i.e., different genomes) indicate polymorphisms between the source genomes. The amplification products generated with any of the compound SSR-directed primers are a mixture of polymorphic and nonpolymorphic fragments. Compared to a conventional AFLP reaction (EP 0534858), from which most of the polymorphisms detected are dominant, Applicants' compound SSR-to-adaptor multiplexed amplification method generates a greater proportion of codominant polymorphisms. Although many of the amplification products generated by this scheme are nonpolymorphic between closely related strains, the proportion of polymorphic products increases between more distantly related lines. In general, genomic polymorphisms can be detected using the SSR-to-adaptor multiplexed amplification among individuals from within a species as well as between species; the greater the evolutionary distance between the genomes being compared, the more polymorphisms expected. Both dominant and codominant polymorphisms can be detected. In either case, a polymorphism revealed by this method may result from any one or a combination of possible causes:

1) One or both restriction sites bordering a given genomic region are missing in one genome (analogous to an RFLP, but here detected by a different method). This may be visible either as a dominant or a codominant difference between genomes;

2) Insertion or deletion differences exist between genomes, within the genomic fragment bordered by common restriction sites (this should be visible as a codominant polymorphism providing the amplification distance is not too great for either allelic fragment);

3) Length differences in the simple sequence repeat between genomes can lead to codominant polymorphic amplification products, generally differing in length by multiples of the repeat unit;

4) Single base differences are present between genomes in the region immediately adjacent to the restriction site, such that the 3'-selective portion of the adaptor-directed primer can discriminate between dissimilar templates, in a manner analogous to an allele-specific amplification.

Because of all these potential sources of polymorphism, the information content on a per locus basis for this type of multiplexed amplification assay is very high. A simple estimate can be made for the minimum number of nucleotide positions at a locus that are informative (i e., at which a polymorphism may be detected). For templates digested with both a 4- and 6-bp cutter:

4 (within the 4 bp restriction site)
+6 (within the 6 bp restriction site)
+0 to 10 (sequence immediately adjacent to the adaptor-specific restriction site)
+0 to 30 (number of nucleotides within the SSR assayable for length variability between genomes)
=10 to 50 nucleotides per amplified locus may be informative for producing a polymorphism between individual genomes. The first three factors in this sum result from single nucleotide variation (e.g., substitutions) between genomes, whereas the fourth factor in the sum results from repeat length variation. Although small insertions and deletions distributed in the entire genome can contribution to the detection of length variability in this as well as other genome assays, the greatly increased probability for repeat length variation at each SSR target locus results in an "above background" level of length polymorphism detectable in the products.

In comparison, the information content for RFLP is 8–12, for RAPDs is 16–18, and for a standard AFLP assay is generally 10–15 nucleotides. Furthermore, compared to conventional AFLP and RAPD technologies, a larger proportion of the polymorphism assayable by this SSR-to-adaptor amplification method is detectable as codominant differences between genomes.

SSR-based polymorphisms detected using this SSR-to-adaptor, or SAMPL, amplification method can be converted into more conventional and convenient single-locus SSR markers. This conversion can be performed, for example, if the multiplexed approach is used to quickly screen through hundreds or thousands of possible polymorphisms between genomes, and if it then is desirable to subsequently assay a chosen subset of these polymorphisms either at a larger, more high througput scale or in order to examine polymorphism at these particular loci more quickly and nonisotopically. This conversion process requires that the desired band be excised from the SAMPL gel and then sequenced. From the nucleotide sequence deduced for the unique sequence flanking the SSR, a "locus-specific" primer can be designed, which flanks and is oppositely oriented towards the SSR. This unique primer can then be paired with a general adaptor-directed primer and used to amplify from the original fragment mixture. The resulting adaptor-to-unique primer PCR product then can be sequenced to discover the other unique flanking sequence of the SSR, and the second locus-specific primer can be designed. Finally, the two oppositely oriented locus-specific flanking primers are used as a pair to amplify the region spanning the desired SSR locus in a target genome.

EXAMPLES

Materials and Methods

Restriction enzymes, ligases and polymerases used in the following examples were obtained from BRL Life Technologies (Gaithersburg, Md.) or New England Biolabs (Beverly, Mass.).

The source of the soybean cultivars, Bonus and *soja* PI 81762, was Theodore Hymowitz, University of Illinois. All other soybean lines, including the *G. max* cultivars wolverine, NOIR-1, N85-2176, Harrow, CNS, Manchu, Mandarin, Mukden, Richland, Roanoke, Tokyo and PI 54-60, and the *G. soja* accession PI 440-913, were obtained from the USDA Soybean Germplasm Collection, University of Illinois (Dept. Agronomy, Turner Hall, Urbana, Ill.). The source of the *Z. mays* inbred cultivars, B73 and Mo17, and the elite lines, LH82, LH119 and LH204, was Holden's Foundation Seeds, Williamsburg, Iowa. The source of the *Z. mays* inbred line, CM37, was Benjamin Burr, Brookhaven National Laboratory, Upton, N.Y. The AEC272 and ASKC28 *Z. mays* lines were obtained from Dr. Denton Alexander, University of Illinois. Genomic DNA from five different human sources, as well as from salmon and mouse BABL/c, was purchased from commercial sources (Sigma, St. Louis, Mo. or Clontech, Palo Alto, Calif.).

Reagents, buffers and protocols used for restriction digests, ligations, 5'-end phosphorylation-labeling of primers and PCR amplifications are given below in Table III.

TABLE III

REACTION PROTOCOLS
TEMPLATE PREPARATION AND AMPLIFICATION REACTION SETUP

| Reagent | Stock | Final Conc | Amount Stock Used | Comments |
|---|---|---|---|---|
| Restriction Digestion | | | | |
| Genomic DNA | High-quality | .0833 ug/ul | 2.5 ug | should be of the highest quality |
| 10× Buffer | 10× | 1× | 5 ul | compatible with most restriction |
| | 100 mM Tris-acetate | 10 mM | | endonucleases and with the subsequent ligation reaction |

TABLE III-continued

REACTION PROTOCOLS
TEMPLATE PREPARATION AND AMPLIFICATION REACTION SETUP

| Reagent | Stock | Final Conc | Amount Stock Used | Comments |
|---|---|---|---|---|
|  | 100 mM Mg-acetate | 10 mM |  |  |
|  | 500 mM K-acetate | 50 mM |  |  |
|  | 50 mM DTT | 5 mM |  |  |
|  | pH 7.5 |  |  |  |
| Restriction enzymes |  |  |  | neither should be methyl-sensitive |
| Taq I (4 bp recognition site) | 10 units/ul | 5 units/ug DNA | 1.25 ul | 4 bp recognition site |
| Pst I (6 bp recognition site) | 10 units/ul | 5 units/ug DNA | 1.25 ul | 6 bp recognition site |
| H2O |  |  | bring to 50 ul |  |
| Adaptor ligation |  |  |  |  |
| Taq I-Ad | 50 pmol/ul | .833 pmol/ul | 1.0 ul | double strand adaptor for 4 bp enzyme |
| Biotin-Pst I-Ad | 5 pmol/ul | .0833 pmol/ul | 1.0 ul | 5'-biotinylated adaptor for 6 bp enzyme |
| 10× Buffer |  | 1× | 1.0 ul | same buffer as for restriction digests |
| ATP | 10 mM | 0.2 mM | 1.2 ul |  |
| T4 DNA Ligase | 1 unit/ul | 1 unit/reaction | 1.0 ul |  |
| H2O |  |  | 4.8 ul | bring to 10 ul total |
| Primer radiolabeling |  |  |  |  |
| SSR primer | 50 ng/ul | 5 ng/ul | 3.0 ul | for 17–18 mers, equal to ~25 pmoles |
| 10× Kinase Buffer | 10× | 1× | 3.0 ul | Contains no ATP |
|  | 600 mM Tris-Cl | 60 mM |  | Verify buffer compatibility with the enzyme manufacturer's recommendations |
|  | 100 mM | MgCl2 | 10 mM |  |
|  | 150 mM DTT | 15 mM |  |  |
|  | pH 7.8 |  |  |  |
| [gamma-33P]ATP | 10 uCi/ul | 1.67 uCi/ul | 5.0 ul | At 3000 Ci/mmol, equal to ~17 pmol. |
| (3000 Ci/mmol) |  |  |  | 32P also can be used, but with poorer gel resolution. |
| T4 polynucleotide kinase | 10 units/ul | 0.17 units/ul | 0.5 ul |  |
| H2O |  |  | bring to 30 ul |  |
| PCR amplification |  |  |  |  |
| biotin-streptavidin selected template DNA |  |  | 2 ul | 2.5 ug input genomic DNA in a final 200 ul selected volume is sufficient for 100 PCR amplifications |
| Taq I adaptor directed-primer SSR-primer | 50 ng/ul | 1.5 ng/ul | 0.6 u (30 ng) | eg., Taq.pr1, Taq.pr2, Taq.pr3, etc. |
| 33P-labeled SSR primer | 5 ng/ul | 0.25 ng/ul | 1.0 ul (5 ng) |  |
| unlabeled SSR primer | 50 ng/ul | 1.25 ng/ul | 0.5 ul (25 ng) | 30 ng total (labeled + unlabeled) |
| 10× PEC Buffer |  | 1× | 2.0 ul | recommended by Perkin-Elmer Cetus for AmpliTaq polymerase (other buffer, containing ammonium sulfate, also are suitable) |
|  | 100 mM Tris-Cl | 10 mM |  |  |
|  | 15 mM MgCl2 | 1.5 mM |  |  |
|  | 500 mM KCl | 50 mM |  |  |
|  | pH 8.5 |  |  |  |
| dNTP mixture | 5 mM each dNTP | 0.2 mM each | 0.8 ul | all four dNTPs in equimolar amounts |
| AmpliTaq polymerase | 5 U/ul | 0.025 U/ul | 0.1 ul | Stoffel fragment of Taq polymerase is not suitable, however, other high-temperature polymerases that carry both a 5' → 3' polymerase and exonuclease activity are suitable |
| H2O |  |  | bring to 20 ul |  |

Preparation of Genomic Template DNA Mixtures:

Genomic DNA was isolated from soybean (*Glycine max*) cultivars using a CTAB/chloroform extraction and CsCl/centrifugation method (Murry et al., *Nuc Acids Res*, 8, 4321, 1980), and from corn (*Zea mays*) cultivars using a urea extraction miniprep method (Chen et al., in *The Maize Handbook*., M. Freeling and V. Walbot, eds., (1993) pp 526–527 New York).

Purified genomic DNA was prepared for amplification reactions in a manner similar to that described by Zabeau (EP 534,858), by complete restriction endonuclease digestion followed by or coupled with ligation of site-specific double-stranded adaptors. The restriction enzyme combinations used for the following examples were either Taq I+Pst I or Taq I+Hind III (a combination of enzymes with tetra- and hexa-nucleotide recognition sites, respectively). Between 1 and 2.5 ug of high molecular weight genomic DNA was digested with 5 units/ug of Taq I in a 50 ul volume at 65° C. for approximately 3 hours in a buffer containing 10 mM Tris acetate, 10 mM magnesium acetate, 50 mM potassium acetate, 5 mM dithiothreitol, pH 7.5, then digested further in the same buffer with 5 units/ug of Pst I or Hind III at 37° C. for 3 h (Table III). The digestion products generated from each input genomic DNA were a mixture of symmetric fragments, bordered at both ends by either Taq I or Pst I (or Hind III) sites, and asymmetric fragments flanked by both a Taq I site and a hexanucleotide site.

Double stranded adaptors were generated by slowly annealing equimolar amounts of the two partially complementary single stranded component oligonucleotides of each pair (see Table III). The double stranded Taq I adaptor (Taq-Ad) at 50 pmole/uL was produced by combining 5000 pmole each of Taq.AdF and Taq.AdR single-stranded oligonucleotides with H₂O to a final volume of 100 uL. For the 5 pmole/ul Pst I and Hind III adaptors (biotin-Pst-Ad or biotin-Hind-Ad), 500 pmole each of the corresponding single stranded oligonucleotides for each were combined in a final volume of 100 uL. To generate the double-stranded molecules, all mixtures were incubated at sequentially decreasing temperatures: 65° C. for 15 min, 37° C. for 15 min, room temperature for 15 min, then finally at 4° C.

This section describes the method that utilizes biotin-streptavidin selection for enriching the genomic fragment mixture prior to the SSR-to-adaptor amplification. To each completed double digestion was added 10 uL of a mixture containing 1 unit T4 DNA ligase, 0.2 mM ATP, and the two double-stranded adaptors, Taq-Ad (50 pmole) and biotin-Pst-Ad or biotin-Hind-Ad (5 pmole), each carrying a different synthetic DNA sequence along its length and each complementary at one end to the single-stranded tetranucleotide or hexanucleotide overhangs on the genomic fragments (Table III). These adaptor ligation reactions were incubated at 37° C. for 3 h. Each adaptor contained a single base alteration within the half-restriction site it carries, so that the reconstructed site generated by each ligation cannot be re-digested. Therefore, restriction enzyme digestions and ligations can be performed simultaneously providing the activities of all enzymes used share a common optimum reaction temperature.

A subset of ligation products, all carrying a biotinylated Pst I adaptor at least one end, was selected out of each digestion/ligation mixture using streptavidin coated paramagnetic beads (Dynal, Lake Success, N.Y.). For each selection, 10 uL beads, washed once in 200 uL STEX (100 mM NaCl, 10 mM Tris-HCl, 1 mM EDTA, 0.1% Triton X-100, pH 8.0) then resuspended in 150 uL STEX, was added to each ligation reaction, and the mixtures incubated for one hour at room temperature on a gently rocking platform. The DNA-adhered beads then were selected out of each mixture using a magnetic rack support; the supernatent was aspirated away, and the beads were resuspended in 200 uL STEX. Four additional cycles of bead selection, washing and aspiration were performed. The final resuspension was transferred to a fresh tube, and the DNA-adhered beads selected in this final cycle were resuspended in 10 mM Tris-HCl, 0.1 mM EDTA, pH 8.0 (100 uL for 1 ug input DNA or 200 uL for 2–2.5 ug input DNA). This selected DNA, which did not have to be purified further from the beads, was a mixture of Taq I-Pst I (or Taq I-Hind III) and Pst I-Pst I (or Hind III-HindIII) fragments, present at an approximate ratio of 30:1, respectively. The selected DNA fragments were used as pooled template for polymerase chain reaction amplifications using one each of a Taq I adaptor-directed primer and a simple sequence repeat (SSR)-directed primer.

For the alternative method of enriching the restriction fragment mixture prior to the final PCR amplification, both restriction site specific adaptors may be either biotin-modified or unmodified. Following adaptor ligation to the restriction fragments, the entire mixture is subjected to up to 16 individual amplification reactions, each of which employs a pair of individual adaptor-directed primers. One primer of each pair corresponds to one of the adaptor sequences, and the second primer to the second adaptor sequence. In each case, the amplification primer carries a single, randomly chosen nucleotide at its 3'-most end. Each primer pair will specifically amplify an approximately 1/16th subset of the original genomic fragment mixture. Any or all of the pre-amplified product mixtures derived from a common restriction fragment population then can serve as an enriched template for the subsequent amplification between an SSR-directed primer and primer representing either of the two flanking adaptors. In this case, this adaptor primer typically carries 2, 3, or more arbitrary 3'-nucleotides, with the nucleotide closest to the restriction site perfectly matching the one nucleotide used on the pre-amplification adaptor primer.

Example 1

Amplification Using 5'-Anchored Simple SSR Primers in a Multiplexed SSR-to-Adaptor Amplification to Detect Polymorphisms Among Soybean Cultivars Example 1 describes the use of primers corresponding to simple SSR sequences flanked at the 5'-end by degenerate nucleotides, for the amplification of adaptor tagged restriction fragments and the subsequent detection of genetic polymorphisms among soybean cultivars. Adaptor-directed primers used in these amplifications are shown in Table I. The SSR primers, herein termed 5'-anchored simple SSR primers, are listed in Table IV.

TABLE IV

5'-ANCHORED SIMPLE SSR PRIMERS

| Primer Name | Sequence(5'→3')/ | SEQ ID NO. | Length | Tm (50mM Salt) | %GC |
|---|---|---|---|---|---|
| HBH(AG)8.5 | HBHAGAGAGAGAGAGGA/ | SEQ ID NO.:3 | 20 | 45.7° C. | 45.00 |
| BHB(GA)8.5 | BHBGAGAGAGAGAGAGAG/ | SEQ ID NO.:4 | 20 | 47.7° C. | 52.50 |
| DVD(TC)8.5 | DVDTCTCTCTCTCTCTCT/ | SEQ ID NO.:5 | 20 | 45.7° C. | 47.50 |
| VDV(CT)8.5 | VDVCTCTCTCTCTCTCTC/ | SEQ ID NO.:6 | 20 | 47.7° C. | 52.50 |
| DBD(AC)7.5 | DBDACACACACACACACA/ | SEQ ID NO.:7 | 18 | 41.8° C. | 47.20 |
| BDB(CA)7.5 | BDBCACACACACACACAC/ | SEQ ID NO.:8 | 18 | 44.1° C. | 52.80 |
| HVH(TG)7.5 | HVHTGTGTGTGTGTGTGT/ | SEQ ID NO.:9 | 18 | 41.8° C. | 47.20 |

TABLE IV-continued

5'-ANCHORED SIMPLE SSR PRIMERS

| Primer Name | Sequence(5'→3')/ | SEQ ID NO. | Length | Tm (50mM Salt) | %GC |
|---|---|---|---|---|---|
| VHV(GT)7.5 | VHVGTGTGTGTGTGTG/ | SEQ ID NO.:10 | 18 | 44.1° C. | 52.80 |
| CCGG(T)10 | CCGGTTTTTTTTTT/ | SEQ ID NO.:11 | 14 | 23.4° C. | 28.60 |
| GCGC(A)10 | GCGCAAAAAAAAAA/ | SE1 ID NO.:12 | 14 | 23.4° C. | 28.60 |
| BDBD(AC)6.5 | BDBDACACACACACACA/ | SEQ ID NO.:13 | 17 | 39.5° C. | 47.00 |
| BHBH(AG)6.5 | BHBHAGAGAGAGAGAGA/ | SEQ ID NO.:14 | 17 | 39.5° C. | 47.00 |
| VHVH(TG)6.5 | VHVHTGTGTGTGTGTGT/ | SEQ ID NO.:15 | 17 | 39.5° C. | 47.00 |
| CGG(CA)C6.5 | CGGCACACACACACACA/ | SEQ ID NO.:16 | 17 | 44.3° C. | 58.80 |

Adaptor modified, biotin-selected genomic DNA from the *Glycine max* strains, NOIR-1, N85-2176 and wolverine, and the *Glycine soja* cultivar, PI 81762, were prepared as described in the MATERIALS AND METHODS. SSR primers were 5'-end labeled with $^{33}$P by combining fifty microcuries of [γ-$^{33}$P]ATP (New England Nuclear) with 150 ng of primer and 5 units of T4 polynucleotide kinase in a 30 uL reaction (Table III). After incubation at 37° C. for 1 h, a 1 uL aliquot of this labeled primer mixture (containing 5 ng primer) was used directly in each amplification reaction.

All amplification reactions were performed simultaneously by cold start initiation and were set up together at room temperature, using a series of reaction cocktails. The master mixture, containing the four components common to all reactions, consisted of (per reaction) 2.0 uL of 10× PEC buffer, 0.8 uL all four dNTPs (5 mM each), 13.0 uL H$_2$O, and 0.1 uL (0.5 units) Amplitaq DNA polymerase (Perkin Elmer Roche) (see Table III and MATERIALS AND METHODS). An aliquot of this master mixture was then added to the appropriate primers to make individual full-primer cocktails; for each final amplification reaction, 15.9 uL of master mix was combined with 0.6 uL unlabeled Taq I adaptor-directed primer (stock is 50 ng/uL), 0.5 uL unlabeled SSR primer, and 1.0 uL (at 5 ng/uL) $^{33}$P-labeled SSR primer. The appropriate biotin-streptavidin selected template DNA (2 uL each) was distributed into 0.2 mL microamplification tubes (Robbins Scientific, Mountain View, Calif.) and placed in individual wells of a Perkin-Elmer 9600 multiwell plate. Eighteen uL of the appropriate full-primer cocktail then was added, to give all reactions a final volume of 20 uL. This final combination of reaction components was quickly completed and the amplification reactions initiated on a Perkin Elmer 9600 thermocycler with as little delay as possible using either a constant 58° C. annealing or a 58° C. touchdown thermocycling protocol:

| Touchdown annealing | |
|---|---|
| denature: | 94° C., 3 min |
| 1 cycle: | 94° C., 30 sec |
| | 65° C., 30 sec |
| | 72° C., 1 min |
| 11 cycles: | 94° C., 30 sec |
| | 64.4° C., 30 sec for 1st cycle, then decrease by 0.6° C. per cycle for the next 10 cycles to a final 58.4° C. |
| | 72° C., 1 min |

| -continued | |
|---|---|
| 23 cycles: | 94° C., 30 sec |
| | 58° C., 30 sec |
| | 72° C., 1 min |
| Constant temperature annealing | |
| denature: | 94° C., 3 min |
| 35 cycles: | 94° C., 30 sec |
| | 58° C., 30 sec |
| | 72° C., 1 min |

The completed amplification reactions were diluted with an equal volume of formamide stop solution (98% deionized formamide, 2 mM EDTA, 0.05% bromophenol blue, 0.05% xylene cyanol), heated to 94° C. for 3 min, then quickly chilled on ice. 2.5 uL of each was immediately loaded onto a 4.5% or a 6% denaturing 30×40×0.4 cm polyacrylamide gel (7M urea, 4.5% acrylamide: N-,N-methylene bis-acrylamide [19:1], 100 mM Tris-HCl, 80 mM boric acid, 1 mM EDTA, pH 8.3) that was first prerun in the same tris-borate-EDTA buffer at 55W for 30 minutes. The loaded samples were electrophoresed at 55 W (corresponds to ~1400–1500 V, 35–40 mA) for two hours, then the gel was transferred to chromatography paper, vacuum dried for 2 h at 80° C., and exposed to Hyperfilm-MP (Amersham) or Biomax (Kodak) X-ray film with an intensifying screen at −70° C. for 2 to 7 days.

FIG. 2 shows a comparison of the amplification products using the 5'-anchored simple SSR-directed primers, DBD (AC)$_{7.5}$, HBH(AG)$_{8.5}$, and HVH(TG)$_{7.5}$. In all cases, the SSR primer was $^{33}$P-labeled and used in combination with each of two different Taq I adaptor-directed primers, Taq.Ad.F and Taq.pr6, which carry zero and one 3' selective nucleotide, respectively (see Table I). Panel a shows the amplification products generated using constant temperature thermocycling and panel b shows the products from a touchdown protocol. Several different 5'-anchored simple SSR-directed primers have been tested, all of which are listed in Table IV. In general, it was found that all such simple SSR-to-adaptor amplifications required a 0–2 nucleotide extension on the 3' end of the adaptor-directed primer to give a suitable number of co-amplified products.

Regardless of the annealing temperature, the constant temperature annealing protocol produced bands on the gels that were extremely smeared and indistinct for nearly every primer combination tested. Raising the annealing temperature from 56° to 58°–59° C. resulted in somewhat less smeariness (FIG. 2a); the products of individual loci generally are discernable. However, the products are not discretely sized, and instead showed a high degree of "stutter" on the gel. The highest constant annealing temperature tested, 60° C., produced relatively few bands for some primer combinations, and no bands for others (data not shown). These results indicate that the efficiency of primer discrimination at most target loci is relatively inefficient when the annealing temperature is held constant throughout the thermocycling. Either the primer does anneal, but at multiple positions within a target locus (producing a stuttering effect), or it does not anneal stably to generate a product. Although an optimal constant annealing temperature for any primer pair ultimately should be determined empirically, it is likely that heterogeneously sized amplification products still will result using this thermocycling method.

In contrast, thermocycling using touchdown conditions (Don., et al., *Nuc. Acid Res.*, 19, 4008, (1991) are designed to lead to highly efficient target locus discrimination and to minimize or eliminate spurious priming by either of the primers in the amplification. In touchdown amplification, the annealing temperature begins deliberately high, then is incrementally lowered in successive cycles, down to a desired, "touchdown" annealing temperature. Touchdown temperatures of both 59° C. and 56° C. were tested. For most SSR-directed primers, this range of final touchdown temperatures was optimal for producing a large number of relatively discrete bands on the gels (see FIG. 2b for an example of the products resulting from 58° C. touchdown reactions; other data not shown), and these bands were reproducible from experiment to experiment.

Individual banding pattern differences in the co-amplified fragments between different templates (i.e., different genomes) indicate polymorphisms between the source genomes. The majority of the amplification products generated by this scheme appear to be nonpolymorphic between the two closely related *G. max* strains, NOIR-1 and N85-2176; however, a greater number of polymorphic products are seen between the more distantly related *G. max*, wolverine and *G. soja* PI 81762 cultivars. In addition, some polymorphisms appear to be dominant (a band amplified from one genome, but no apparent corresponding band from the other), and a few are potentially codominant (bands of similar but nonidentical size amplified from each genome).

This analysis illustrates two important features of the ability to fine tune and customize this assay. First, the two different 5'-anchored simple SSR directed primers, HBH (AG)$_{8.5}$ and DBD(AC)$_{7.5}$, when used against a common set of genomic templates, produced completely different amplification patterns. That these patterns reflect distinctly different subsets of amplification products is consistent with the idea (see FIG. 1) that different subsets of restriction fragments from the genome are likely to carry different SSR target sites. Each band of the gel is the result of a productive amplification between a particular SSR sequence oppositely oriented relative to a Taq I site. Given the estimation for relatively large spacing between SSR sequences of all types in the soybean genome (Wang et al., *Theor. Applied Genetics*, 88, 1 (1994); Morgante & Olivieri, *Plant J* 3, 175 (1993)), it is unlikely that the SSR-to-Taq I site products derived from the HBH(AG)$_{8.5}$ and DBD(AC)7.5 primers in this example cover any genomic loci in common.

A second feature illustrated by this example is that for any chosen SSR primer, the fewer the number of 3'-selective nucleotides on the adaptor-directed primer, the greater the number of co-amplified bands. In general, it is expected that the mixture of products generated using the n=0 version of the adaptor primer is more complex than that for an n=1 primer, and this product mixture is more complex than that for an n=2 primer, and so on. In this example, the Taq I adaptor-directed primer, Taq.AdF carrying zero 3'-selective nucleotides, consistently produced a greater number of labeled reaction products when paired with a given SSR primer, compared to primers carrying one selective nucleotide (Taq.pr6 [n=1=A] or Taq.pr8 [n=1=c]). While in theory, an increase in length of the 3'-extension from n=0 to n=1 should decrease the number of amplified fragments four-fold, it is difficult in practice to quantitate the real difference, primarily because of the great degree of general smeariness and poor resolution of the products derived from 5'-anchored simple SSR primers. Clearly, however, the greatest number of bands, along with the highest levels of background, is visible in the lanes representing reactions amplified with Taq.AdF.

Third, thermocycling conditions employing touchdown conditions generally serve to reduce the smearing within the lanes, and generally makes for sharper product bands, in comparison to use of a constant annealing temperature. However, these sharper bands still are accompanied by a great degree of stutter, which hinders precise comparison of polymorphisms between lanes (genomes).

In general, genomic polymorphisms can be detected among individuals from within a species as well as between species; the greater the evolutionary distance between the genomes being compared, the more polymorphisms are expected. Both dominant and codominant polymorphisms are revealed. However, no matter what the specific reaction thermocycling condition, the use of 5'-anchored simple SSR primers in an SSR-to-adaptor amplification is not ideal for identifying new polymorphisms. Even when the annealing conditions are carefully optimized, as in touchdown thermocycling or in a hot start initiation (not shown), the individual co-amplification products resolve on the gels as rather smeary and indistinct. The high degree of stutter apparent on the autoradiographic images counteracts the clarity of the bands attainable using conventional AFLP (Zabeau EP 534,858), and prevents accurate identification of all but the most prominent polymorphisms.

Example 2

Amplification Using Perfect Compound SSR Primers in a Multiplexed SSR-to-Adaptor Amplification to Detect Polymorphisms Among Soybean Cultivars Example 2 illustrates the use of perfect compound SSR-directed primers in an SSR-to-adaptor amplification method similar to that discussed in Example 1 as a means to improve the resolution and increase the level of polymorphism among the multiplexed amplification products. All of the individual compound SSR primers used for these amplifications are listed in Table V.

TABLE V

COMPOUND SSR PRIMERS

| Primer Name | Sequence(5'→3')/SEQ ID No. | Length | Tm (50mM Salt) | %GC |
|---|---|---|---|---|
| Compound SSR-Directed Primera | | | | |
| (AT)3.5(AG)7.5 | TATATATAGAGAGAGAGAGAGA /63 | 22 | 42.3° C. | 31.80 |
| (TA)7.5(GA)4.5 | ATATATATATATATAGAGAGAGAG /64 | 24 | 40.3° C. | 20.83 |
| (CT)5(AT)7 | CTCTCTCTCTATATATATATATAT /65 | 24 | 40.3° C. | 20.80 |
| (CT)7.5(AT)3.5 | TCTCTCTCTCTCTCTATATATA /66 | 22 | 42.3° C. | 31.80 |
| (CT)7.5(AT)2 | CTCTCTCTCTCTCTCTATA /67 | 19 | 41.6° C. | 42.00 |
| (AT)3.5(GT)6.5 | TATATATGTGTGTGTGTGTG /68 | 20 | 40.5° C. | 35.00 |
| (AT)6.5(GT)4.5 | TATATATATATATGTGTGTGTG /69 | 22 | 38.5° C. | 22.70 |
| (AT)8.5(GT)3.5 | TATATATATATATATATGTGTGTG /70 | 24 | 38.6° C. | 16.70 |
| (CA)4.5(TA)7.5 | ACACACACATATATATATATATAT /71 | 24 | 38.4° C. | 16.70 |
| (CA)6.5(TA)4.5 | ACACACACACACATATATATAT /72 | 22 | 40.4° C. | 27.27 |
| (CA)7.5(TA)2.5 | ACACACACACACACATATAT /73 | 20 | 40.5° C. | 35.00 |
| (GT)7.5(AT)2 | TGTGTGTGTGTGTGTATAT /74 | 19 | 39.5° C. | 36.80 |
| (GA)7.5(TA)2 | GAGAGAGAGAGAGAGATAT /75 | 19 | 41.6° C. | 42.10 |
| (TC)3.5(AC)5.5 | CTCTCTCACACACACACA /76 | 18 | 42.9° C. | 50.00 |
| (TC)4.5(AC)4.5 | CTCTCTCTCACACACACA /77 | 18 | 42.9° C. | 50.00 |
| (TG)4.5(AG)4.5 | GTGTGTGTGAGAGAGAGA /78 | 18 | 42.9° C. | 50.00 |
| (CA)4.5(GA)4.5 | ACACACACAGAGAGAGAG /79 | 18 | 42.9° C. | 50.00 |
| (TC)4.5(TG)4.5 | CTCTCTCTCTGTGTGTGT /80 | 18 | 42.9° C. | 50.00 |
| (GA)3.5(GT)5.5 | AGAGAGAGTGTGTGTGTG /81 | 18 | 42.9° C. | 50.00 |

Most of these compound SSR sequences are represented either on sequenced soybean genomic clones that were shown by hybridization to contain one of the dinucleotide repeats that comprise the compound SSR (M. Morgante and C. Andre, unpublished), or on cloned plant and animal sequences that have been entered into public DNA sequence databases (e.g., GenBank; see Table II).

DNA templates were generated essentially as described in Example 1, from the *G. max* cultivars wolverine, NOIR-1, N85-2176, Harrow, CNS, Manchu, Mandarin, Mukden, Richland, Roanoke, Tokyo, PI54-60, and Bonus, as well as from *G. soja* accessions PI81762 and PI440.913. Following double digestion with either Taq I+Pst I or Taq I+Hind III, ligation of double stranded Taq I-Ad and biotin-Pst I-Ad (or biotin-Hnd III-Ad) adaptors, and selection of fragments carrying at least one biotinylated Pst I or Hind III end, the amplification reactions were performed using a series of reaction cocktails and a cold start setup, all as described in Example 1. In all cases, only the compound SSR primer was 5'-end labeled using [$\gamma$-$^{33}$P]ATP. The amplifications were performed on a Perkin Elmer 9600 thermocycler using a 56° C. final annealing temperature touchdown profile:

denature: 94° C., 3 min
1 cycle: 94° C., 30 sec
   65° C., 30 sec
   72° C., 1 min
11 cycles: 94° C., 30 sec
   64.3° C., 30 sec for 1st cycle, then decrease by 0.7° C. per cycle for the next 10 cycles to a final 56° C.
   72° C., 1 min
23 cycles: 94° C., 30 sec
   56° C., 30 sec
   72° C., 1 min Following electrophoresis on 6% denaturing polyacrylamide gels in tris-borate-EDTA buffer essentially as described in Example 1, the co-amplified products were visualized by autoradiography after intensifying screen enhanced exposure at −70° C. to Kodak Biomax X-ray film.

All of the compound SSR-directed primers listed in Table V have been used in this protocol to detect polymorphisms among different soybean cultivars. All primers used represent perfect compound SSR sequences in which one of the component nucleotides is "in-phase" across the two adjacent dinucleotide repeats. Surprisingly, not all of the primers listed in Table V were equally effective at generating products, and not all generated products with the same degree of polymorphism, even when they were predicted to do so based upon cloned sequence compilations (Table II). The compound primer that produces the greatest number of co-amplified fragments from the soybean genome is $(CA)_x$ $(TA)_y$ (where x and y are multiples of 0.5, but each $\geq 1$). FIG. 3a shows the amplification products from a $(CA)_{7.5}$ $(TA)_{2.5}$ version of this primer, used in combination with Taq.AdF (containing zero 3'-selective nucleotides) and Taq.pr8 (one 3'-nucleotide, -C). Also shown in FIG. 3a are the products from the compound sequence primers $(TC)_{4.5}$ $(TG)_{4.5}$ and $(CT)_{7.5}(AT)_{3.5}$, which amplify only relatively few fragments even when the Taq I primer is completely nonselective. This result was surprising, since $(CT)_x(AT)_y$ sequences appear to be the second-most abundant class of compound repeat on isolated soybean clones (see Table II). As primers, $(CA)_{7.5}(TA)_{2.5}$ and $(CT)_{7.5}(AT)_{3.5}$ differ primarily in the length of their 3'-$(AT)_y$ repeat. The differing efficiencies of these two primers in otherwise identical amplification reactions may largely be a function of the length of the "leading" 3'-$(AT)_y$ sequence. In constrast, the extremely low number of amplified products resulting from $(TC)_{4.5}(TG)_{4.5}$ is probably the result of low copy number of this compound repeat in the soybean genome (see Table II). Shown in FIG. 3b are the products generated using $(TG)_{4.5}$ $(AG)_{4.5}$, and $(TC)_{4.5}(AC)_{4.5}$, each in combination with the same two Taq I adaptor-specific primers. An intermediate number of products are amplified by each of these two compound SSR sequences.

The amplification products generated with any of the perfect compound SSR-directed primers are a mixture of polymorphic and nonpolymorphic fragments. For example, some of the products from the $(CA)_{7.5}(TA)_{2.5}$ primer are completely nonpolymorphic among all 15 different *G. max* and *G. soja* genotypes tested; however, many of the products reflect either dominant or codominant polymorphisms among these genomes. The products amplified using $(CA)_{7.5}(TA)_{2.5}$ in combination with either Taq.AdF(n=0) or Taq.pr8(n=1=c) from FIG. 3a were cataloged:

|  |  | SSR-to-adaptor amplification $(CA)_{7.5}(TA)_{2.5}$ | |
|---|---|---|---|
| Band scored as: | AFLP[a] | +TaqAdF[b] | +TaqPr8 |
| monomorphic | 64 | 12 | 14 |
| dominant[c] | 34 | 44 | 40 |
| codominant[d] | 1 | 8 | 8 |
| codominant + dominant[e] | 3 | 8 | 16 |
| TOTAL | 102 | 72 | 78 |
| % polymorphic products | 37% | 83% | 82% |
| Expected heterozygosity[f] | 0.32 | 0.44 | 0.43 |

[a]The Amplified Fragment Length Polymorphism assay on the same set of 15 soybean cultivars as used for the SSR-to-adaptor amplifications, using two paired adaptor-directed primers corresponding to the Taq I adaptor and Pst I adaptor, respectively (not shown)
[b]The TaqAdF lanes carry a high level of background, and only the most unambiguous polymorphisms were scored
[c]A band was scored as polymorphic in the indicated category if at least one of the 15 genotypes showed a difference from the others
[d]These scorings are very conservative, minimum estimates of the true incidence of codominant, allelic products; only the most obvious codominant relationships among the 15 template genotypes were scored. A more accurate measurement of the codominance frequency in these reactions requires analysis of the segregation of potentially allelic bands in a population derived from pairs of these genotypes
[e]A band could be scored as both codominant and dominant if it appears to be completely absent from at least one genotype and if it also was represented by at least two size variants in bands that were amplified in other genotypes
[f]Expected heterozygosity (H = 1 − $\Sigma p_i^2$,) for each band (locus) was calculated as the sum of the allele frequencies ($p_i$) for that locus; an average of H for every polymorphic locus could then be calculated This set of amplification products does not represent the entirety of the $(CA)_{\geq 7.5}(TA)_{\geq 2.5}$ loci in the soybean genome. Within the biotin-selected subset of Taq I+Pst I double digested template fragments, amplification was limited to only those $(CA)_{\geq 7.5}(TA)_{\geq 2.5}$ genomic loci for which this SSR is within an amplifiable distance of and is oriented oppositely to a Taq I site, and for which no other Taq I site lies on the other side of the SSR, between the SSR and the "selectable" Pst I site (see FIG. 1). The remaining $(CA)_{\geq 7.5}$ $(TA)_{\geq 2.5}$ loci in the genome can be amplified from template DNAs constructed using different sets of restriction endonucleases. FIG. 4 illustrates that when just one of the two restriction enzymes is changed (Pst I is replaced by Hind III as selectable enzyme site), the pattern of amplified fragments is markedly different from that produced with Pst I+Taq I. Therefore, generating templates restricted with differing combinations of restriction endonucleases, as well as assaying each template preparation with a large set of different compound SSR and adaptor primer combinations, should allow the detection of a greater proportion of the total number of polymorphic SSR loci in any given genome.

In comparison to the low resolution of amplification products generated by SSR-to-adaptor amplification using 5'-anchored simple SSR primers (see Example 1), the alternative use of compound SSR primers allows for a much greater level of product resolution. Each band/product is accompanied by far less stutter, and the overall background in the lanes is noticeably reduced, even when a cold start amplification is used (compare FIG. 2 to FIGS. 3a, 3b). This lower amount of background permits good discrimination of individual products, allowing the assignment of allelic relationships among bands to be made with a greater level of confidence. In some instances, a polymorphism might arise from single nucleotide variation within the region covered by the restriction site or the adaptor-directed primer. Nevertheless, a number of the polymorphisms (most of those categorized as codominant or both codominant and dominant among the 15 cultivars tested) appear to arise from variation in the length of the compound SSR through which primer extension occurs; these are recognizable as codominant polymorphisms whose sizes differ by multiples of the unit length of the repeat. The ability to include repeat length variation as one type of polymorphism that is identifiable by this assay allows for a higher level of polymorphism to be visualized from each amplification reaction. It is possible that this assay will allow for the calculation of genetic distances, both within and between species, with great efficiency. Evidence for this comes from similarity estimates (not shown) made from the data shown in FIGS. 3a and 3b; distances calculated for pairings of *G. max*-*G. max* genotypes from this data are less than the calculated distances for *G. max*-*G. soja* pairings.

Example 3

Amplification Using Perfect Compound SSR Primers in a Multiplexed SSR-to-Adaptor Reaction for Genetic Mapping Example 3 illustrates the use of the SSR-to-adaptor amplification method to generate genetic markers. To determine whether the polymorphic bands detected between *G. max*, Bonus and *G. soja*, PI 81762 are genetically heritable, and to determine whether these polymorphisms could have utility for genetic mapping, polymorphic products between these strains were scored and mapped to the soybean genome.

Genomic template DNAs were made, as described in the MATERIALS AND METHODS, from 66 individuals at the $F_2$ generation from a cross involving the bonus and soja parents (from T. Hymowitz, U. of Illinois). For this example, Taq I and Hind III restriction endonucleases were used for the template DNA double digestions. The digestions, adaptor ligations, and subsequent streptavidin-biotin selections were performed as described in MATERIALS AND METHODS.

TABLE VI

| Marker Name | Band Name | Parents PI81762 | Bonus | 1 | 2 | 4 | 6 | 7 | 8 | 9 | 12 | 13 | 14 | 15 | 16 | 17 | 18 | 19 | 20 |
|---|---|---|---|---|---|---|---|---|---|---|---|---|---|---|---|---|---|---|---|
| 301 | 94-23.p4 | a | B | B | a | a | a | a | a | a | a | a | a | B | a | a | a | B | a |
| 305 | 94-23.p1 | a | B | a | a | a | a | a | a | B | a | a | a | a | a | a | a | a | B |
| 307 | 94-23.p5 | A | b | b | b | A | b | b | b | b | A | A | A | b | b | b | b | A | A |
| 309 | 94-23.p9 | A | b | b | b | b | b | A | A | b | b | A | b | A | A | A | b | A | A |
| 320 | 94-23.p6 | A | b | b | b | b | b | b | b | b | b | b | b | A | b | b | b | A | b |
| 322 | 94-23.p3 | A | B | H | A | B | H | H | H | B | H | H | A | B | m | H | B | A | H |
| 323 | 94-23.p7 | A | b | b | b | b | b | A | b | b | A | b | b | b | A | A | A | b | m |
| 324 | 94-23.P8a | a | B | B | a | a | B | a | B | a | a | a | a | a | a | B | a | a | a |
| 325 | 94-23.p8b | a | B | a | a | B | a | a | a | a | a | B | a | a | B | a | a | a | a |
| 326 | 94-23.p10 | a | B | a | a | a | B | B | B | a | a | a | a | a | B | B | a | B | a |
| 329 | 94-23.p12 | A | b | b | b | b | b | b | b | b | b | b | b | b | m | b | b | b | b |
| 331 | 94-23.p13 | A | b | b | b | A | b | A | b | A | b | b | b | b | b | b | b | b | A |
| 333 | 94-23.p14 | A | b | b | b | b | b | A | b | b | A | b | b | b | b | b | b | b | A |

| Marker Name | Band Name | PI81762 | Bonus | 21 | 22 | 25 | 27 | 28 | 29 | 30 | 31 | 33 | 34 | 36 | 37 | 38 | 39 | 40 | 41 |
|---|---|---|---|---|---|---|---|---|---|---|---|---|---|---|---|---|---|---|---|
| 301 | 94-23.p4 | a | B | a | a | B | a | a | B | B | a | B | a | B | a | B | a | a | B |
| 305 | 94-23.p1 | a | B | a | a | a | B | B | a | a | a | a | a | a | a | a | a | B | a |
| 307 | 94-23.p5 | A | b | b | b | b | b | b | A | A | A | b | A | b | b | b | A | b | b |
| 309 | 94-23.p9 | A | b | b | A | b | A | b | b | b | b | A | b | A | A | b | b | A | b |
| 320 | 94-23.p6 | A | b | b | b | b | b | b | b | A | b | b | A | b | A | b | A | b | B |
| 322 | 94-23.p3 | A | B | B | H | H | A | B | B | H | H | B | H | A | H | B | A | A | B |
| 323 | 94-23.p7 | A | b | b | b | m | b | b | b | b | b | b | b | b | b | b | m | b | b |
| 324 | 94-23.P8a | a | B | a | a | a | a | a | B | a | B | a | a | B | a | B | B | a | a |
| 325 | 94-23.p8b | a | B | a | B | a | a | a | B | a | a | B | B | a | B | B | a | a | a |
| 326 | 94-23.p10 | a | B | a | a | a | B | a | a | a | a | B | a | a | B | a | a | B | a |
| 329 | 94-23.p12 | A | b | A | A | b | b | b | b | b | b | b | b | A | b | m | b | b | A |
| 331 | 94-23.p13 | A | b | b | b | b | b | A | b | b | b | b | A | b | b | b | A | b | A |
| 333 | 94-23.p14 | A | b | b | A | b | A | b | b | b | A | b | b | b | A | b | b | b |

| Marker Name | Band Name | PI81762 | Bonus | 42 | 43 | 44 | 45 | 46 | 47 | 48 | 49 | 50 | 51 | 52 | 53 | 54 | 56 | 57 | 58 |
|---|---|---|---|---|---|---|---|---|---|---|---|---|---|---|---|---|---|---|---|
| 301 | 94-23.p4 | a | B | a | a | a | a | a | B | a | a | a | a | a | B | B | B | a | B |
| 305 | 94-23.p1 | a | B | a | B | a | a | B | a | a | a | B | B | B | a | a | a | a | a |
| 307 | 94-23.p5 | A | b | A | A | b | b | b | A | A | b | b | b | A | b | A | b | b | b |
| 309 | 94-23.p9 | A | b | A | b | A | A | A | b | b | b | b | b | b | m | A | b | b | b |
| 320 | 94-23.p6 | A | b | m | b | b | A | b | b | b | b | A | b | A | b | A | b | A | b |
| 322 | 94-23.p3 | A | B | H | H | A | B | m | A | A | B | H | H | A | A | m | m | H | A |
| 323 | 94-23.p7 | A | b | b | b | b | b | A | b | b | b | b | A | b | m | b | b | b | b |
| 324 | 94-23.P8a | a | B | B | a | a | B | a | a | a | a | B | a | B | a | B | a | a | a |
| 325 | 94-23.p8b | a | B | a | a | a | a | a | a | a | a | a | a | a | a | a | a | a | a |
| 326 | 94-23.p10 | a | B | a | a | B | a | B | a | B | a | a | a | a | a | a | B | a | a |
| 329 | 94-23.p12 | A | b | b | b | A | A | b | b | A | b | b | A | b | A | b | b | b | b |
| 331 | 94-23.p13 | A | b | b | b | b | A | b | b | b | b | A | b | A | b | A | b | b | b |
| 333 | 94-23.p14 | A | b | b | A | b | A | b | b | b | b | b | b | A | A | b | A | b |

| Marker Name | Band Name | PI81762 | Bonus | 59 | 62 | 64 | 68 | 74 | 76 | 77 | 78 | 80 | 82 | 83 | 84 | 85 | 86 | 91 | 96 |
|---|---|---|---|---|---|---|---|---|---|---|---|---|---|---|---|---|---|---|---|
| 301 | 94-23.p4 | a | B | a | a | a | a | a | a | a | B | a | a | a | B | B | a | a | B |
| 305 | 94-23.p1 | a | B | a | B | a | a | B | a | a | B | a | a | a | a | a | a | a | a |
| 307 | 94-23.p5 | A | b | b | A | b | b | b | b | b | b | b | b | b | b | m | A | b | A |
| 309 | 94-23.p9 | A | b | b | b | b | b | b | b | A | b | b | b | b | b | m | b | b | b |
| 320 | 94-23.p6 | A | b | b | b | A | b | b | A | b | b | b | b | b | b | b | b | b | b |
| 322 | 94-23.p3 | A | B | H | A | A | H | H | H | H | A | B | B | A | A | m | m | m | H |
| 323 | 94-23.p7 | A | b | A | b | A | A | b | b | b | b | b | A | A | m | A | b | m |
| 324 | 94-23.P8a | a | B | B | B | B | a | a | a | a | B | a | B | a | a | a | m | a | a |
| 325 | 94-23.p8b | a | B | B | a | a | a | a | a | B | a | B | a | a | B | a | a | B |
| 326 | 94-23.p10 | a | B | a | a | a | B | a | a | a | B | B | a | a | m | a | a | a |
| 329 | 94-23.p12 | A | b | A | b | A | b | b | A | b | b | b | b | A | m | b | b | b |
| 331 | 94-23.p13 | A | b | b | b | b | b | A | A | b | b | b | A | b | A | b | b | A |
| 333 | 94-23.p14 | A | b | b | b | b | A | b | b | A | b | A | b | A | m | b | A | b |

| Marker Name | Band Name | PI81762 | Bonus | Linkage Group | Log-Likelihood of Linkage |
|---|---|---|---|---|---|
| 301 | 94-23.p4 | a | B | LG19 | 16.9 |
| 305 | 94-23.p1 | a | B | LG1 | 10.8 |
| 307 | 94-23.p5 | A | b | LG11 | 11.4 |
| 309 | 94-23.p9 | A | b | LG15 | 9.4 |
| 320 | 94-23.p6 | A | b | LG6 | 10.4 |
| 322 | 94-23.p3 | A | B | LG2 | 5.4 |
| 323 | 94-23.p7 | A | b | LG10 | 5.8 |

TABLE VI-continued

| | | Parents | | F2 Individual | Designation |
|---|---|---|---|---|---|
| 324 | 94-23.P8a | a | B | LG14 | 12.0 |
| 325 | 94-23.p8b | a | B | LG13 | 11.3 |
| 326 | 94-23.p10 | a | B | LG11 | 14.1 |
| 329 | 94-23.p12 | A | b | LG9 | 3.6 |
| 331 | 94-23.p13 | A | b | LG1 | 3.3 |
| 333 | 94-23.p14 | A | b | LG5 | 11.7 |

The $(CA)_{7.5}(TA)_{2.5}$ compound SSR-directed primer (Table V) was 5'-end labeled using [$\gamma$-$^{33}$P]ATP and then used in combination with Taq.pr6 adaptor-directed primer (Table I) for multiplexed amplifications on the parent and $F_2$ templates. These amplifications utilized the cold start, 56° C. touchdown thermocycling protocol detailed in Example 2. Amplification products were resolved on 6% denaturing polyacrylamide gels, then dried and exposed to Kodak Biomax X-ray film. The autoradiograph of these products is shown in FIG. 5a. At least 15 amplification products were decisively polymorphic between the parental templates, and demonstrated mendelian segregation among the F2 individuals. Most of these segregate as dominant polymorphisms, and the probability that each segregated in the F2 progeny at a 3:1 or a 1:2:1 mendelian ratio, simply by chance alone, was consistently less than 5%. The parental inheritance of each polymorphic product was determined for each of the 66 F2 individuals, and the scores for 13 of these polymorphisms are shown in Table VI. With this specific primer combination, most of the more unambiguous of the polymorphic bands appear to segregate as dominant markers; only a few polymorphisms appear to segregate codominantly. With other specific primer combinations, however, the incidence of codominant segregation is often higher. Most codominant polymorphisms were more problematic to score in that homozygotes sometimes could not be distinguished from heterozygotes. Therefore, each of the polymorphisms from this amplification were scored with a default assumption of dominance, and instances of true codominance were revealed following mapping.

In order to map these bands to the soybean genome, these inheritence scores were correlated with those of 600 RFLP and single-locus SSR markers previously mapped to the soybean genome (J. A. Rafalski and S. V. Tingey, in: Genetic Maps: Locus Maps of Complex Genomes. 6th Edition. Cold Spring Harbor Laboratory Press, Cold Spring Harbor, N.Y., 1993). This standard genetic map (data not shown) was constructed by standard RFLP methodology from analysis of the segregation patterns of many RFLP markers in the same F2 population as used in this example (for standard RFLP mapping technology, see T. Helentjaris, et al., 1986, Theor. Appl. Genet., 72, 761 which reference is incorporated herein). The basis for genetic mapping analysis is that markers located near to each other in the genome are inherited together in the F2 progeny, while markers located farther apart are co-inherited less frequently. Segregation analysis and marker map positions were then calculated using a computer segregation analysis program, MapMaker (E. S. Lander, et al., 1987 Genomics, 1, 174) which had been modified by Applicants for the Macintosh. The results indicated that nearly every polymorphic amplification product with an approximate 3:1 dominant segregation ratio, or a 1:2:1 codominant segregation ratio, among the F2 progeny can be mapped to the soybean genome. This is illustrated in FIG. 5b, where 6 polymorphisms from Table VI all map to independent sites on various linkage groups. In total, the 15 polymorphisms mapped from this single primer combination are distributed among 10 different linkage groups; in some instances, two or more polymorphisms localize to linked sites on the same linkage group. The probability that each of the polymorphisms in FIG. 5b localize to these positions purely by chance from the observed data varied from 1 in $10^{3.29}$ to 1 in $10^{16.88}$, indicating the strength of these map positions. This example demonstrates that polymorphisms revealed by the present invention, SSR-to-adaptor multiplexed amplification, have utility as genetic markers.

DNA was isolated and templates were made from each of 66 F2 individuals segregating from a cross between PI81762 and Bonus soybean lines. The genotype of each individual at each of the indicated marker loci was determined as follows: A score of "A" or "B" designates that the locus was inherited from the PI81762 or Bonus parent, respectively. A score of H designates that the locus was inherited from both PI81762 and Bonus. A scope of "a" designates that the locus was inherited only from PI81762 or that it was inherited from both Bonus and PI81762. A score of "b" designates that the locus was inherited only from Bonus or that it was inherited from both Bonus and PI81762. A score of "m" indicates missing data.

Example 4

Amplification Using Perfect Compound SSR
Primers in a Multiplexed SSR-to-Adaptor Reaction
to Detect Polymorphisms in Other Plant and
Animal Genomes Example 4 illustrates the use of perfect compound SSR primers for the amplification of genomic DNA from other non-soybean genomes including corn, salmon, human and mouse. Genomic DNA was isolated from the Z. mays inbred cultivars, B73, Mo17, ASKC28, LH82, LH119, LH204, AEC272, and CM37, using a urea extraction miniprep procedure (Chen et al., in: The Maize Handbook., M. Freeling and V. Walbot, eds., (1993) pp 526–527, New York). Genomic DNA from five different human sources, as well as from salmon and mouse (BALB/c) were purchased from commercial sources (Sigma, St. Louis, Mo. or Clontech, Palo Alto Calif.). All these DNAs were double digested either with Taq I+Pst I or Taq I+Hind III, the restriction fragments ligated to adaptors specific to these restriction sites, and biotin-streptavidin selections performed as described in Examples 1 and 2.

Amplification reactions were performed as described in Example 2, using several individual perfect compound SSR-directed primers ($^{33}$P-labeled), each primer in combination with individual Taq I adaptor-directed primers carrying either zero or one 3'-selective nucleotide. The amplifications were performed using cold start, 56° C. final touchdown thermocycling conditions, and the labeled products resolved on 6% denaturing polyacrylamide gels. Examples of the amplification products from these plant and mammalian genomes are shown in FIG. 6, panels a, b and c.

In all genomes tested, every specific compound SSR and Taq I adaptor primer combination produced a distinct set of amplification products (a fingerprint). In general, the degree to which any two fingerprints are similar is a function of the evolutionary distance between the individuals. These SSR-to-adaptor amplification product fingerprints have two components that can differ: the absolute number of fragments and their collective pattern on the gel. First, a given SSR-directed primer may generate a completely different relative number of amplification products in one species compared to another species, indicating that the compound SSR locus amplified by that primer may be present in entirely different copy numbers in one phylogenetic group compared to another. For example, the number of co-amplified fragments using the compound repeat, $(CA)_{7.5}(TA)_{2.5}$ appears to be much greater (by at least 2–5 fold) in the mammalian genomes than in soybean or corn (see FIG. 6) indicating that mammals contain a greater number of $(CA)_{\geq 7.5}(TA)_{\geq 2.5}$ target loci. This relationship is consistent with the greater estimated frequency of $(CA)_n$ repeats in mammalian versus soybean or corn genomes (Wang et al., *Theor. Applied Genetics*: 88, 1 (1994); Morgante & Olivieri, *Plant J* (1993); Beckmann & Weber *Genomics* 12.627 (1992)). Second, within a narrow phylogenetic group (species or genus), the pattern of amplification products between individuals is generally similar, reflecting the general conservation of restriction sites and SSR loci in the different, yet closely related genomes. Polymorphisms between individuals are detected whenever a particular restriction site or SSR locus that contributes to a given amplified fragment in one genome carries a base substitution, insertion/deletion, or repeat length difference compared to the other genomes of the same species. Virtually no similarities are obvious in the patterns of amplification products between individuals whose evolutionary distance extends beyond the same genus, consistent with the accepted idea that the more diverged the two genomes being compared, the more unlikely they will share common loci. The sets of amplified fragments are entirely different, for example, between individual genomes from human compared to mouse or rat, and the amplification patterns (and likely the set of amplified products) appear to share no similiarities between soybean and mammals, or even between soybean and corn.

Example 5

Effects of Varying the Primer Constitution and Thermocycling Conditions to Generate Different Sets of Amplification Products Viariability in the SSR-to-adaptor amplification reaction, and therefore in the products obtained, results not only from the reaction and thermocycle setup conditions described above, but also from subleties in the design of the primers and the thermocycling parameters used in these amplifications. Once a particular compound SSR has been chosen as the target locus sequence for this assay, then either partially or entirely different sets of amplification products still can be generated by altering any one of the following primer design criteria: 1) the number and composition of the 3'-extension nucleotide(s) on the adaptor-directed primer; 2) the relative lengths of the two constituent simple repeats that comprise the compound SSR primer; 3) the particular strand of the double-stranded compound SSR locus chosen to correspond to the single-stranded primer (i.e., the directionality of the SSR primer). In addition, the quality of the data generated by a particular amplification is affected by the mode by which thermocycling is initiated.

1. Design of the Adaptor-directed Primer:

This primer, which corresponds to the synthetic adaptor ligated to the restricted ends of the genomic DNA, can carry a variable number (zero to ten) and arbitrary sequence of nucleotides at its 3'-end. As described by Zabeau (EP 534,858), these variable 3'-nucleotides on the primer anneal specifically to "unknown" sequences that are directly adjacent to the adaptor and restriction site on a genomic DNA fragment, and the recognition by each of only a subset of all possible fragments in the template mixture provides exquisite specificity in the amplification reaction. Since such primers that are otherwise identical in sequence except for differences in the few 3'-most nucleotide(s) can amplify completely nonoverlapping sets of amplification products, they behave much like allele-specific amplification primers (Newton et al., (1989) *Nuc. Acids Res* 17: 2503; Kwok et al., (1990) *Nuc. Acids Res*. 18: 999; Wu et al., (1989) *Proc. Natl. Acad. Sci. USA* 86: 2757), except that their use requires no prior sequence knowledge of the genomic locus to be amplified, and each primer will selectively co-recognize multiple target sites in a template DNA mixture.

In general, the longer the 3'-extension the more selective the primer; as the variable 3'-extension is made longer, the adaptor primer becomes more restricted to recognize a smaller number of potential genomic target sites, leading to a smaller real number of coamplified products. The addition of each nondegenerate nucleotide onto the 3'-extension leads to approximately 4-fold greater template discrimination. In addition, different single nucleotides at the 3'-most base position(s) give unique template specificities to otherwise identical primers. These principles are illustrated by the examples shown in FIG. 7. The $^{33}$P-labeled perfect compound SSR primer, $(CA)_{7.5}(TA)_{2.5}$, was used for SSR-to-adaptor amplification to generate specific products from the genomes of several soybean cultivars, using the experimental conditions described in Example 2. This SSR primer was paired with each of several different Taq I adaptor-directed primers, which all differ only at their 3'-most nucleotide positions (see Table I):

| .AdF | .pr5 | .pr6 | .pr7 | .pr8 | .pr9 |
|------|------|------|------|------|------|
| 0 | 1 (-G) | 1 (-A) | 1 (-T) | 1 (-C) | 2 (-AC) |

The Taq I adaptor-directed primer with the shortest 3'-extension (zero nucleotides), Taq.AdF, is completely nonselective and generated the largest number of products; the primer with the longest extension (Taq.pr9) is the most selective and resulted in the fewest amplification products. All four of the primers carrying one nucleotide as a 3'-extension amplified approximately the same number of products; however, the set of products from each of these four primers is unique compared to the sets from the other three. The complex pattern of bands amplified using Taq.AdF is actually a composite of all four one-base extension primers. That is, the pattern generated by each of these four primers is approximately a ¼ subset of the pattern amplified by the zero-base extended primer. Thus, varying both the number and composition of the 3'-selective nucleotides on the adaptor-directed primer is sufficient to generate individual, either partially or completely, nonoverlapping sets of amplification products from the same template when paired with a given SSR-directed primer. The choice of which 3'-extensions to use will depend largely upon relative nucleotide frequencies in a target genome and upon the abundance in the genome of the specific SSR that serves as the other priming site.

2. Relative Lengths of the Two Constituent Simple Repeats Comprising the Compound SSR Primer:

Every simple and nearly every compound SSR locus in the genome is a double stranded structure whose individual strands carry different permutations of nucleotides. A single-stranded primer that may specifically anneal to one strand at a SSR locus will not anneal to the opposite strand (with the exception of the 9 specific palindromic compound SSR sequences combinations; see Table II). Therefore, a given SSR-directed primer will primer-extend from each genomic target locus in a polar, unidirectional manner, and any compound SSR locus can be recognized and primed from by any of four different primer classes. In addition, each of these four canonical primer classes can include a wide range of individual primers, all differing by the length of the two constituent repeats within the primer. Changes in the lengths of these constituent repeats have profound effects on primer efficacy and the fidelity of reproducible amplifications; in general, the longer the 5'-anchoring repeat relative to the 3'-priming repeat, the better the primer's specificity and priming efficiency in the amplification.

Multiple, individual primers, each differing from the others by the length of its two constituent repeats, have been tested for four different compound SSR sequences: $(CT)_x(AT)_y$, $(AT)_x(AG)_y$, $(CA)_x(TA)_y$, $(AT)_x(GT)_y$ (i.e., the values of x and y are varied for a particular SSR type). FIG. 8 shows the results of a test using three different $(CA)_x(TA)_y$ primers, $(CA)_{4.5}(TA)_{7.5}$, $(CA)_{6.5}(TA)_{4.5}$, and $(CA)_{7.5}(TA)_{2.5}$, and three different $(AT)_x(GT)_y$ primers, $(AT)_{3.5}(GT)_{6.5}$, $(AT)_{8.5}(GT)_{2.5}$, and $(AT)_{6.5}(GT)_{4.5}$. All five of these primers were calculated to have a Tm in the range of 38–42° C. Each was 5'-labeled with $^{33}P$ and paired individually with three different Taq I-directed primers (Taq.AdF, Taq.pr6 and Taq.pr8) in amplification reactions using biotin-selected soybean template DNAs, PI81762 and wolverine, as described in Example 2. Neither of the $(AT)_x(GT)_y$ primers performed very efficiently, although $(AT)_{3.5}(GT)_{6.5}$ generated at least some products, whereas the other two $(AT)_x(GT)_y$ primer versions failed completely to generate any amplification products. In contrast, all three $(CA)_x(TA)_y$ primers were able to generate products, although the number of amplified fragments varied among the three primers. These results demonstrate that the longer the 5'-anchoring repeat and the shorter the 3'-primer extension repeat, the more amplification products are produced. This same conclusion was drawn from similar experiments performed with $(CT)_x(AT)_y$ and $(AT)_x(AG)_y$ primers carrying variable constituent repeat lengths (not shown).

3. Polarity of the Single Stranded Compound SSR-directed Primer:

The choice of which strand of a double-stranded compound SSR locus to use as a primer can be extremely critical for determining the success of the SSR-to-adaptor amplification reaction. For some compound SSRs, one strand of the double-stranded SSR was found to serve as an efficient primer whereas the opposite strand failed completely, regardless of the relative lengths of the constituent repeats on the primer. This difference was most extreme for compound SSRs containing a $(AT)_n$ repeat; the only type of $(AT)_n$ containing primer that will lead to efficiently generated amplification products under standard conditions (described in Example 2) is one in which the $(AT)_n$ sequence is very short (1.5–3 repeat units) and is situated as the 3'-primer extension end. FIG. 8, for example, illustrates the superior efficiency of $(CA)_x(TA)_y$ primers in contrast to $(AT)_x(GT)_y$ primers, which represent the complementary strands of the same compound SSR. All three of the $(AT)_x(GT)_y$ primers tested were extremely inefficient at generating amplification products (two were failures), even though the calculated $T_m$ values of all the primers were approximately the same. It is likely that this difference in primer efficiency results from the difference in placement of the $(AT)_n$ stretch within the primer. A and T nucleotides display weak hydrogen bonding during base pairing, and oligonucleotides containing $(AT)_n$ stretches often have self-complementarity artifacts in competition with weak annealing to the template. Therefore, it is likely than an $(AT)_n$ stretch at the 5' end of a primer will serve poorly to anchor the primer to the template, whereas a short $(AT)_n$ at the 3' end will have been well-anchored by the upstream non-$(AT)_n$ portion of the primer.

Primers corresponding to compound SSRs that are devoid of $(AT)_n$ repeats are affected much less by the relative order of the two constituent repeats. For example, the individual primers in the two complementary primer sets, $(TC)_{4.5}(AC)_{4.5}$ versus $(TG)_{4.5}(AG)4.5$ (see FIG. 3) and $(CA)_{4.5}(GA)_{4.5}$ vs. $(TC)_{4.5}(AC)_{4.5}$, (not shown) appear to generate amplification products with approximately equivalent efficiencies.

4. Mode of Thermocycling Initiation

The reaction setup protcol described in the previous examples is essentially a cold start, and allows the possibility for primers to anneal under nonstringent conditions both to template sites that are not necessarily a perfect match, and to multiple, staggered sites within a target locus (the latter leads to a stuttering effect of the amplification products on the gel). This simple reaction setup protocol, nevertheless, routinely was sufficient to generate amplification products that could be distinguished as polymorphic between genomes. In fact, the cold start reaction products from compound SSR directed primers were consistently quite sharp and distinct; however, comparable products derived from 5'-anchored simple SSR primers generally lacked the same clarity and sharpness (compare FIGS. 2 and 3). Much of this indistinctness and individual product heterogeneity, for both types of SSR-directed primer, could be obviated by the use of a hot start initiation for the thermocycling. A hot start protocol (Chou et al., *Nuc. Acids Res.* 20, 1717, 1992) prevents spurious primer annealing to incorrect template sites prior to the first denaturation, and generates products that resolve more sharply and discretely on the gel.

Otherwise identical amplification reactions were performed using the cold start procedure described in Examples 1 and 2, and also using two different hot start initiation procedures. For one type of hot start, all the components of each amplification reaction were combined as described in MATERIALS AND METHODS, except that the SSR-directed primer (both 5'-end labeled and unlabeled versions) was excluded from the full primer cocktail. The reaction tubes were capped (18.5 uL reaction volume), and the first denaturation step of the thermocycling was performed (94° C., 3 min). The reactions were then held at 80° C. while 1.5 uL of the appropriate SSR primer (1.0 uL of 5 ng/uL $^{33}$P-labelled plus 0.5 uL of 50 ng/uL unlabelled) was added to each reaction. Exponential amplification was then initiated, using either a constant 58° C. annealing temperature or a touchdown (56° or 58° C. final) thermocycling protocol. For the second hot start method, Ampliwax PCR-50 gems were used essentially as described by the manufacturer (Stratagene, La Jolla, Calif.), except that a mixture of 10× buffer, $MgCl_2$, dNTPs, $H_2O$, and primers (5.4 uL total) was first heated with the Ampliwax and allowed to cool, then a second mixture (14.6 uL) consisting of template DNA, AmpliTaq DNA polymerase, PCR buffer and $H_2O$ was added over the top of the re-solidified wax layer (final concentrations of each match those in the standard cold start amplifications). Thermocycling was then initiated, using the touchdown annealing protocol detailed in Example 2.

The amplifications illustrated in FIGS. 2–8 all employed a cold start protocol. A direct comparison of the two initiation procedures, however, is shown in FIG. 9. Two sets of amplifications using the perfect compound SSR primer, $(CA)_{7.5}(TA)_{2.5}$, paired with three different Taq I adaptor primers (Taq.AdF, Taq.pr6, Taq.pr8) were performed using the conditions described in Example 2 (56° C. final touchdown temperature); one set was initiated with a standard cold start, the other with the first hot start protocol described above. These results demonstrate that a hot start is superior for generating the most discrete bands with the least amount of stutter, although the cold start is adequate for producing products that nonetheless are discernable as polymorphic between genotypes.

In general, a hot start produced the sharpest product bands on the gel for nearly every SSR-directed primer tested. The most extreme difference between these protocols were observed when 5'-anchored simple SSR primers were used. In fact, a cold start using 5'-anchored simple SSR primers often led to unacceptably smeared and fuzzy product bands. The differences were generally more subtle for compound SSR primers, although some SSR primers (those with long stretches of $(AT)_n$ as the 5'-anchor) failed to produce any product under hot start conditions.

Example 6

Amplification Using Perfect Compound SSR-Directed Primers for Inter-SSR Amplifications to Detect Polymorphisms Example 6 demonstrates the use of perfect,in-phase compound SSR primers in a single-primer amplification for the production and detection of genetic polymorphisms. Simple SSR sequences containing 3 degenerate bases at the extreme 5'-end have been shown previously to serve as efficient primers for amplification between neighboring SSR sequences in the genome (Zietkiewicz, et al., *Genomics*, 20, 176, (1994)). Similarly, primers corresponding to compound SSR sequences also are useful and extremely efficient for generating inter-SSR amplification products in a single-primer PCR reaction. Generally, the same compound SSR primers that are most efficient in SSR-to-adaptor amplifications, those with in-phase sequences and corresponding to the most abundant of the compound SSRs in the genome (see Table II) also are the most efficient for generating inter-SSR amplification products.

FIG. 10 illustrates the single-primer amplification products obtained using both 5'-anchored simple SSR primers and compound SSR primers, from three different cold start thermocycling protocols: 58° C. constant, 58° C. touchdown and 56° C. touchdown (described in Examples 1 and 2). SSR primers were 5'-end labeled with [γ-$^{33}$P]ATP as described in MATERIALS AND METHODS. Either 20 ng undigested genomic DNA or the standard amount of digested, biotin-selected adaptor modified template DNA were combined with the compound SSR primer (5 ng labeled primer combined with 25 ng unlabeled primer) and the other non-primer components of the amplification reactions described in the previous examples. No adaptor-directed primers were added. These reactions were performed using both hot start (not shown) and cold start conditions although the products resulting from hot start were more discrete and better resolved on the gels.

FIG. 10, panel a shows a comparison of the products from undigested genomic DNA for soybean (Bonus and PI 81762) and corn (B73 and CM37) cultivars using the 5'-anchored simple SSR primer, $DBD(AC)_{7.5}$, generated with the three thermocycling profiles indicated. Panel b illustrates a comparison of the amplification products obtained using the 5'-anchored simple SSR primers, $DBD(AC)_{7.5}$ and HBH $(AG)_{8.5}$, and perfect compound SSR primers, $(AT)_{3.5}(AG)_{7.5}$ and $(AT)_{3.5}(GT)_{6.5}$, from both undigested and Taq I+Pst I digested, biotin-selected template DNAs from soybean wolverine and PI 81762. Two different thermocycling methods were used, as indicated.

The undigested DNA templates produced a greater number of amplification products than did the digested templates. The reactions using digested, adaptor-ligated templates served as single-primer controls for the SSR-to-adaptor amplifications described in Examples 1 and 2; relatively few fragments were amplified by the single SSR primer from these cut DNA templates, indicating that most of the amplification products observed in the SSR-to-adaptor reactions are dependent upon the presence of both the SSR sequence and a neighboring adaptor sequence on each digested DNA fragment. The few single-primer products that are visible may result either from bona fide inter-SSR amplification within single DNA fragments, or perhaps from some sort of inter-fragment pairing.

These results demonstrate that compound, as well as simple, SSR primers can generate inter-SSR amplification products from the corn and soybean genomes. The multiple products generated from an individual SSR primer are a mixture of nonpolymorphic and polymorphic fragments. The polymorphic bands between genotypes indicate length differences between or within neighboring SSR sequences in the genome; these fragments are potential markers for genome identification, fingerprint analysis, or marker assisted selection.

Example 7

Conversion of SSR-to-Adaptor Band Polymorphisms to Single-Locus SSR Markers

Once a good SSR is found by using the SSR-to-adaptor amplification (or SAMPL) method, it often may be desirable to focus only on this single SSR, or just a few SSRs, for subsequent analysis of a species, and to examine variation at these few SSRs using a more a straightforward, nonradioactive, single-locus method.

To accomplish conversion of a band from a SAMPL gel to a single locus marker, this band is first excised from the dried gel (see FIG. 11). The DNA from the band is eluted from the gel by heating in 100 uL $H_2O$ at 95° C., 15 min. The debris is pelleted by centrifugation for 2 min at 12000 rpm, and the DNA in the supernate is precipitated by adding 0.1 volume 3M sodium acetate, pH 5.3, 0.025 volumes 20 mg/mL glycogen and 2.5 volumes ethanol, incubating at −70° C. 30 min, then centrifuging at 12000 rpm, 10 min. The pelleted DNA is washed once in 70% ethanol, air-dried, then resuspended in 10 uL $H_2O$. One uL of this DNA then is used as template for PCR amplification using conditions as described in Example 2, except that the SSR-directed primer and the adaptor-directed primer (each at 1.5 ng/uL final concentration; corresponding exactly to the primer pair used for the original amplification) each are unlabeled (see FIG. 11). These re-amplification products are purified using a Qiagen (Chatsworth, Calif.) PCR fragment cleanup kit, and the purified DNA fragments either are subcloned into a suitable T-vector (for example, pGEM-T, Promega, Madison, Wis.) and the insert sequenced using vector-directed primers, or are sequenced directly without subcloning, using the adaptor-directed primer as the sequencing primer. In either case, the DNA sequence for the amplified fragment is obtained, allowing design of the first locus-specific flanking primer (lsfp-1). This primer corresponds to the unique sequence flanking the SSR on the amplified fragment, and is oriented with its 3'-end toward the SSR (FIG. 11).

The lsfp-1 primer then is paired with a primer corresponding to the second adaptor used for the initial preparation of the restriction fragment templates, for amplification across the targeted SSR. This amplification can be performed with or without radiolabeling the lsfp-1 primer, although the nonspecific background is reduced with a radiolabled lsfp-1 primer. The specifically amplified adaptor-to-lsfp-1 band is excised from the gel and sequenced as described above.

From the resulting DNA sequence of the other flanking region of the SSR, a second locus-specific flanking primer, lsfp-2, then is designed. The 3'-end of this primer is oriented toward the SSR, oppositely to lsfp-1.

Finally, the lsfp-1 and lsfp-2 unique primers are paired and used for PCR amplification either using restriction fragmented DNA template mixtures or using unrestricted genomic DNA templates. Use of this primer pair generates a locus-specific marker that spans the targeted SSR. However, repeat length variation at this SSR now can be detected quickly and nonradioactively from any undigested genome using these specific flanking region primers.

What is claimed is:

1. An improved method of detecting polymorphisms between two individual nucleic acid samples comprising amplifying segments of nucleic acid from each sample using primer-directed amplification and comparing said amplified segments to detect differences, the improvement comprising wherein at least one of the primers used in said amplification consists of a perfect compound simple sequence repeat wherein said primer further comprises sequences that span the junction between two adjacent constituent simple sequence repeats.

2. The process of claim 1 wherein said perfect compound simple sequence repeat primer is described by formula I $$5' \ (XY)_n(NM)_n \ 3' \qquad I$$

wherein:

n is independently 2–15;

X is A, C, T or G;

Y is A, C, T or G;

N is A, C, T or G;

M is A, C, T or G;

and provided that: X≠Y;

N≠M; and

XY≠NM.

3. The process of claim 1 wherein n is independently 4 to 8.

4. The process of claim 1 wherein said perfect compound simple sequence repeat primer is described by formula II $$5' \ (XYZ)_m(LMP)_m \ 3' \qquad II$$

wherein:

m is independently 2–10;

X is A, C, T or G;

Y is A, C, T or G;

Z is A, C, T or G;

M is A, C, T or G;

N is A, C, T or G;

P is A, C, T or g;

and provided that: X, Y and Z are not all the same;

L, M and P are not all the same; and;

XYZ≠NMP.

5. The process of claim 4 wherein m is independently 2 to 4.

6. The process of claim 1 wherein said perfect compound simple sequence repeat primer is in-phase, described by Formula III or IV $$5' \ (XY)_n(XZ)_n \ 3' \qquad III$$
$$5' \ (YX)_n(ZX)_n \ 3' \qquad IV$$

wherein:

n is independently 2–15;

X is A, C, T or G;

Y is A, C, T or G;

Z is A, C, T or G;

and provided that: Y≠X

Z≠X and

Y≠Z.

7. The process of claim 6 wherein n is independently 4 to 8.

8. The process of claim 6 wherein the value of n for the 5' repeating dinucleotide is greater than the value of n for the 3' repeating dinucleotide.

9. The process of claim 6 wherein said in-phase perfect compound simple sequence repeat primer is selected from the group consisting of:

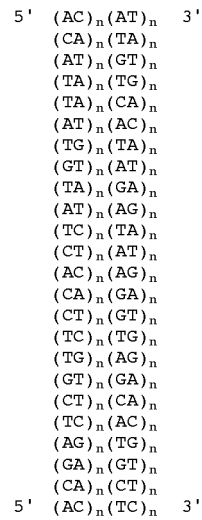

wherein n is independently 2 to 15.

10. The process of claim 1 wherein said primer-directed amplification is performed using a single primer consisting of a perfect compound simple sequence repeat.

11. The process of claim 1 wherein said perfect compound simple sequence repeat is in-phase.

12. A process for detecting polymorphisms between two samples of nucleic acid comprising separately treating each nucleic acid sample according to the steps of a–d:

a) digesting the nucleic acid with at least one restriction enzyme whereby restriction fragments are generated;

b) ligating adaptor segments to the ends of the restriction fragments of step a);

c) amplifying the fragments of step b) using primer-directed amplification wherein the amplification primers comprise a first primer consisting of a perfect compound simple sequence repeat, and a second primer comprising a sequence which is complementary to an adaptor segment of step b) wherein said primers further comprises sequences that span the junction between two adjacent constituent simple sequence repeats; and d) comparing the amplified nucleic acid products of step c) from each nucleic acid sample to detect differences.

13. The process of claim 12 in step c) wherein said first primer consists of a perfect compound simple sequence repeat which is in-phase.

14. The process of claim 12 in step c) wherein said second primer further comprises at the 3' end from 1 to 10 arbitrary nucleotides.

15. The process of claim 12 at step a) wherein two different restriction enzymes are used to digest said nucleic acid, one restriction enzyme recognizing a tetranucleotide site on the sample nucleic acid and the other restriction enzyme recognizing a hexanucleotide site on the sample nucleic acid; and further wherein at step b) two different adaptor segments are ligated to the restriction fragments generated at step a).

16. The process of claim 15 wherein at step b) one of the two adaptor segments carries a member of a binding pair.

17. The process of claim 16 wherein said member of a binding pair is biotin.

18. The process of claim 16 further comprising an additional step performed after step b):

b) (i) separating those fragments of step b) which carry a member of a binding pair from those fragments of step b) which do not carry a member of a binding pair; and further at step c) wherein only those fragments at step b)(i) which carry a member of a binding pair are amplified according to step c).

19. The process of claim 12 at step c) wherein said first primer carries a reporter molecule.

20. The process of claim 19 wherein said reporter is $^{32}$P or $^{33}$P.

21. The process of claim 12 at step c) wherein said amplification is performed using a touchdown thermocycling protocol.

22. The process of claim 12 at step c) wherein said amplification is initiated using a hot start protocol.

23. The process of claim 13 wherein said in-phase perfect compound simple sequence repeat is selected from the group consisting of:

```
5'  (AC)n(AT)n   3'
    (CA)n(TA)n
    (AT)n(GT)n
    (AT)n(GT)n
```

-continued
```
    (TA)n(TG)n
    (TA)n(CA)n
    (AT)n(AC)n
    (TG)n(TA)n
    (GT)n(AT)n
    (TA)n(GA)n
    (AT)n(AG)n
    (TC)n(TA)n
    (CT)n(AT)n
    (AC)n(AG)n
    (CA)n(GA)n
    (CT)n(GT)n
    (TC)n(TG)n
    (TG)n(AG)n
    (GT)n(GA)n
    (CT)n(CA)n
    (CA)n(CT)n
    (AG)n(TG)n
    (GA)n(GT)n
    (CA)n(CT)n
5'  (AC)n(TC)n   3'
``` wherein n is independently 2 to 15.

24. The process of claim 23 wherein the value of n for the 5' repeating dinucleotide is greater than the value of n for the 3' repeating dinucleotide.

* * * * *

SEQUENCE LISTING (1) GENERAL INFORMATION:

(iii) NUMBER OF SEQUENCES: 89

(2) INFORMATION FOR SEQ ID NO:1:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

CACACACACA CACACACACA CATATATATA TATATATATA      40

(2) INFORMATION FOR SEQ ID NO:2:

(i) SEQUENCE CHARACTERISTICS:
      (A) LENGTH: 40 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

TATATATATA TATATATATG TGTGTGTGTG TGTGTGTGTG      40

(2) INFORMATION FOR SEQ ID NO:3:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:3:

AGAGAGAGAG AGAGAGA      17

(2) INFORMATION FOR SEQ ID NO:4:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:4:

GAGAGAGAGA GAGAGAG                                                   17

(2) INFORMATION FOR SEQ ID NO:5:

(i) SEQUENCE CHARACTERISTICS:
        (A) LENGTH:  17 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:5:

TCTCTCTCTC TCTCTCT                                                   17

(2) INFORMATION FOR SEQ ID NO:6:

(i) SEQUENCE CHARACTERISTICS:
        (A) LENGTH:  17 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:6:

CTCTCTCTCT CTCTCTC                                                   17

(2) INFORMATION FOR SEQ ID NO:7:

(i) SEQUENCE CHARACTERISTICS:
        (A) LENGTH:  15 base pairs
        (B) TYPE:  nucleic acid
        (C) STRANDEDNESS: single
        (D) TOPOLOGY:  linear (ii) MOLECULE TYPE:  DNA (genomic)

(xi) SEQUENCE DESCRIPTION:  SEQ ID NO:7:

ACACACACAC ACACA                                                     15

(2) INFORMATION FOR SEQ ID NO:8:

(i) SEQUENCE CHARACTERISTICS:
        (A) LENGTH:  15 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:8:

CACACACACA CACAC                                                     15

(2) INFORMATION FOR SEQ ID NO:9:

(i) SEQUENCE CHARACTERISTICS:
        (A) LENGTH:  15 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:9:

TGTGTGTGTG TGTGT                                                     15

(2) INFORMATION FOR SEQ ID NO:10:

```
       (i) SEQUENCE CHARACTERISTICS:
            (A) LENGTH:  15 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:10:

GTGTGTGTGT GTGTG                                                        15

(2) INFORMATION FOR SEQ ID NO:11:

(i) SEQUENCE CHARACTERISTICS:
            (A) LENGTH:  14 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:11:

CCGGTTTTTT TTTT                                                         14

(2) INFORMATION FOR SEQ ID NO:12:

(i) SEQUENCE CHARACTERISTICS:
            (A) LENGTH:  14 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:12:

GCGCAAAAAA AAAA                                                         14

(2) INFORMATION FOR SEQ ID NO:13:

(i) SEQUENCE CHARACTERISTICS:
            (A) LENGTH:  13 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:13:

ACACACACAC ACA                                                          13

(2) INFORMATION FOR SEQ ID NO:14:

(i) SEQUENCE CHARACTERISTICS:
            (A) LENGTH:  13 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:14:

AGAGAGAGAG AGA                                                          13

(2) INFORMATION FOR SEQ ID NO:15:

(i) SEQUENCE CHARACTERISTICS:
            (A) LENGTH:  13 base pairs
            (B) TYPE:  nucleic acid
            (C) STRANDEDNESS:  single
```

(D) TOPOLOGY:  linear (ii) MOLECULE TYPE:  DNA (genomic)

(xi) SEQUENCE DESCRIPTION:  SEQ ID NO:15:

TGTGTGTGTG TGT                                                          13

(2) INFORMATION FOR SEQ ID NO:16:

(i) SEQUENCE CHARACTERISTICS:
        (A) LENGTH:  17 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:16:

CGGCACACAC ACACACA                                                      17

(2) INFORMATION FOR SEQ ID NO:17:

(i) SEQUENCE CHARACTERISTICS:
        (A) LENGTH:  21 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:17:

CTCGTAGACT GCGTACATGC A                                                 21

(2) INFORMATION FOR SEQ ID NO:18:

(i) SEQUENCE CHARACTERISTICS:
        (A) LENGTH:  14 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:18:

TGTACGCAGT CTAC                                                         14

(2) INFORMATION FOR SEQ ID NO:19:

(i) SEQUENCE CHARACTERISTICS:
        (A) LENGTH:  17 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:19:

CTCGTAGACT GCGTACC                                                      17

(2) INFORMATION FOR SEQ ID NO:20:

(i) SEQUENCE CHARACTERISTICS:
        (A) LENGTH:  15 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:20:

AGCTGGTACG CAGTC                                            15

(2) INFORMATION FOR SEQ ID NO:21:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

GACGATGAGT CCTGAC                                           16

(2) INFORMATION FOR SEQ ID NO:22:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

CGGTCAGGAC TCAT                                             14

(2) INFORMATION FOR SEQ ID NO:23:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

GGAATTCTGG ACTCAGT                                          17

(2) INFORMATION FOR SEQ ID NO:24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

GATCACTGAG TCCAGAATTC C                                     21

(2) INFORMATION FOR SEQ ID NO:25:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

TGGCCTTTAC AGCGTC                                           16

(2) INFORMATION FOR SEQ ID NO:26:

(i) SEQUENCE CHARACTERISTICS:
    (A) LENGTH: 14 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:26:

TACACGCTGT AAAG                                                14

(2) INFORMATION FOR SEQ ID NO:27:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

CTCGTAGACT GCGTACC                                             17

(2) INFORMATION FOR SEQ ID NO:28:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

CTGCGTACCA GCTTACA                                             17

(2) INFORMATION FOR SEQ ID NO:29:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

CTGCGTACCA GCTTACC                                             17

(2) INFORMATION FOR SEQ ID NO:30:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

CTGCGTACCA GCTTAAC                                             17

(2) INFORMATION FOR SEQ ID NO:31:

(i) SEQUENCE CHARACTERISTICS:
        (A) LENGTH: 17 base pairs
        (B) TYPE: nucleic acid
        (C) STRANDEDNESS: single (D) TOPOLOGY:  linear (ii) MOLECULE TYPE:  DNA (genomic)

(xi) SEQUENCE DESCRIPTION:  SEQ ID NO:31:

CTGCGTACCA GCTTGTC                                                17

(2) INFORMATION FOR SEQ ID NO:32:

(i) SEQUENCE CHARACTERISTICS:
          (A) LENGTH:  16 base pairs
          (B) TYPE:  nucleic acid
          (C) STRANDEDNESS:  single
          (D) TOPOLOGY:  linear (ii) MOLECULE TYPE:  DNA (genomic)

(xi) SEQUENCE DESCRIPTION:  SEQ ID NO:32:

CTGCGTACCA GCTTAC                                                 16

(2) INFORMATION FOR SEQ ID NO:33:

(i) SEQUENCE CHARACTERISTICS:
          (A) LENGTH:  16 base pairs
          (B) TYPE:  nucleic acid
          (C) STRANDEDNESS:  single
          (D) TOPOLOGY:  linear (ii) MOLECULE TYPE:  DNA (genomic)

(xi) SEQUENCE DESCRIPTION:  SEQ ID NO:33:

CTGCGTACCA GCTTAA                                                 16

(2) INFORMATION FOR SEQ ID NO:34:

(i) SEQUENCE CHARACTERISTICS:
          (A) LENGTH:  21 base pairs
          (B) TYPE:  nucleic acid
          (C) STRANDEDNESS:  single
          (D) TOPOLOGY:  linear (ii) MOLECULE TYPE:  DNA (genomic)

(xi) SEQUENCE DESCRIPTION:  SEQ ID NO:34:

CTCGTAGACT GCGTACATGC A                                           21

(2) INFORMATION FOR SEQ ID NO:35:

(i) SEQUENCE CHARACTERISTICS:
          (A) LENGTH:  18 base pairs
          (B) TYPE:  nucleic acid
          (C) STRANDEDNESS:  single
          (D) TOPOLOGY:  linear (ii) MOLECULE TYPE:  DNA (genomic)

(xi) SEQUENCE DESCRIPTION:  SEQ ID NO:35:

GACTGCGTAC ATGCAGAC                                               18

(2) INFORMATION FOR SEQ ID NO:36:

(i) SEQUENCE CHARACTERISTICS:
          (A) LENGTH:  18 base pairs
          (B) TYPE:  nucleic acid
          (C) STRANDEDNESS:  single
          (D) TOPOLOGY:  linear (ii) MOLECULE TYPE:  DNA (genomic)

(xi) SEQUENCE DESCRIPTION:  SEQ ID NO:36:

```
GACTGCGTAC ATGCAGAA                                                    18

(2) INFORMATION FOR SEQ ID NO:37:

(i) SEQUENCE CHARACTERISTICS:
        (A) LENGTH:  18 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:37:

GACTGCGTAC ATGCAGCA                                                    18

(2) INFORMATION FOR SEQ ID NO:38:

(i) SEQUENCE CHARACTERISTICS:
        (A) LENGTH:  18 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:38:

GACTGCGTAC ATGCAGTT                                                    18

(2) INFORMATION FOR SEQ ID NO:39:

(i) SEQUENCE CHARACTERISTICS:
        (A) LENGTH:  17 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:39:

GACTGCGTAC ATGCAGA                                                     17

(2) INFORMATION FOR SEQ ID NO:40:

(i) SEQUENCE CHARACTERISTICS:
        (A) LENGTH:  17 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:40:

GACTGCGTAC ATGCAGC                                                     17

(2) INFORMATION FOR SEQ ID NO:41:

(i) SEQUENCE CHARACTERISTICS:
        (A) LENGTH:  16 base pairs
        (B) TYPE:  nucleic acid
        (C) STRANDEDNESS:  single
        (D) TOPOLOGY:  linear (ii) MOLECULE TYPE: DNA (genomic)

(xi) SEQUENCE DESCRIPTION:  SEQ ID NO:41:

GACGATGAGT CCTGAC                                                      16

(2) INFORMATION FOR SEQ ID NO:42:
```

(i) SEQUENCE CHARACTERISTICS:
           (A) LENGTH: 15 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:42:

ATGAGTCCTG ACCGA                                                        15

(2) INFORMATION FOR SEQ ID NO:43:

(i) SEQUENCE CHARACTERISTICS:
           (A) LENGTH: 17 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:43:

TGAGTCCTGA CCGAACC                                                      17

(2) INFORMATION FOR SEQ ID NO:44:

(i) SEQUENCE CHARACTERISTICS:
           (A) LENGTH: 17 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:44:

TGAGTCCTGA CCGAACA                                                      17

(2) INFORMATION FOR SEQ ID NO:45:

(i) SEQUENCE CHARACTERISTICS:
           (A) LENGTH: 17 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:45:

TGAGTCCTGA CCGACAC                                                      17

(2) INFORMATION FOR SEQ ID NO:46:

(i) SEQUENCE CHARACTERISTICS:
           (A) LENGTH: 17 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:46:

TGAGTCCTGA CCGACAA                                                      17

(2) INFORMATION FOR SEQ ID NO:47:

(i) SEQUENCE CHARACTERISTICS:
           (A) LENGTH: 16 base pairs
           (B) TYPE: nucleic acid
           (C) STRANDEDNESS: single

```
        (D) TOPOLOGY:  linear (ii) MOLECULE TYPE:  DNA (genomic)

(xi) SEQUENCE DESCRIPTION:  SEQ ID NO:47:

ATGAGTCCTG ACCGAG                                                    16

(2) INFORMATION FOR SEQ ID NO:48:

(i) SEQUENCE CHARACTERISTICS:
        (A) LENGTH:  16 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:48:

ATGAGTCCTG ACCGAA                                                    16

(2) INFORMATION FOR SEQ ID NO:49:

(i) SEQUENCE CHARACTERISTICS:
        (A) LENGTH:  16 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:49:

ATGAGTCCTG ACCGAT                                                    16

(2) INFORMATION FOR SEQ ID NO:50:

(i) SEQUENCE CHARACTERISTICS:
        (A) LENGTH:  16 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:50:

ATGAGTCCTG ACCGAC                                                    16

(2) INFORMATION FOR SEQ ID NO:51:

(i) SEQUENCE CHARACTERISTICS:
        (A) LENGTH:  16 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:51:

TGAGTCCTGA CCGAAC                                                    16

(2) INFORMATION FOR SEQ ID NO:52:

(i) SEQUENCE CHARACTERISTICS:
        (A) LENGTH:  16 base pairs
        (B) TYPE:  nucleic acid
        (C) STRANDEDNESS:  single
        (D) TOPOLOGY:  linear (ii) MOLECULE TYPE:  DNA (genomic)

(xi) SEQUENCE DESCRIPTION:  SEQ ID NO:52:
```

TGAGTCCTGA CCGAAA                                                     16

(2) INFORMATION FOR SEQ ID NO:53:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:53:

TGAGTCCTGA CCGACA                                                     16

(2) INFORMATION FOR SEQ ID NO:54:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:54:

GGAATTCTGG ACTCAGT                                                    17

(2) INFORMATION FOR SEQ ID NO:55:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:55:

GGAATTCTGG ACTCAGTGAT C                                               21

(2) INFORMATION FOR SEQ ID NO:56:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:56:

TTCTGGACTC AGTGATCT                                                   18

(2) INFORMATION FOR SEQ ID NO:57:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:57:

TCTGGACTCA GTGATCTT                                                   18

(2) INFORMATION FOR SEQ ID NO:58:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:58:

CTGGACTCAG TGATCTTC    18

(2) INFORMATION FOR SEQ ID NO:59:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:59:

TGGCCTTTAC AGCGTC    16

(2) INFORMATION FOR SEQ ID NO:60:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:60:

GCCTTTACAG CGTCTAAT    18

(2) INFORMATION FOR SEQ ID NO:61:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:61:

CCTTTACAGC GTCTAATC    18

(2) INFORMATION FOR SEQ ID NO:62:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:62:

CCTTTACAGC GTCTAATCA    19

(2) INFORMATION FOR SEQ ID NO:63:

(i) SEQUENCE CHARACTERISTICS:
        (A) LENGTH: 22 base pairs
        (B) TYPE: nucleic acid
        (C) STRANDEDNESS: single (D) TOPOLOGY:  linear (ii) MOLECULE TYPE:  DNA (genomic)

(xi) SEQUENCE DESCRIPTION:  SEQ ID NO:63:

TATATATAGA GAGAGAGAGA GA                                                22

(2) INFORMATION FOR SEQ ID NO:64:

(i) SEQUENCE CHARACTERISTICS:
            (A) LENGTH:  24 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:64:

ATATATATAT ATATAGAGAG AGAG                                              24

(2) INFORMATION FOR SEQ ID NO:65:

(i) SEQUENCE CHARACTERISTICS:
            (A) LENGTH:  24 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:65:

CTCTCTCTCT ATATATATAT ATAT                                              24

(2) INFORMATION FOR SEQ ID NO:66:

(i) SEQUENCE CHARACTERISTICS:
            (A) LENGTH:  22 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:66:

TCTCTCTCTC TCTCTATATA TA                                                22

(2) INFORMATION FOR SEQ ID NO:67:

(i) SEQUENCE CHARACTERISTICS:
            (A) LENGTH:  19 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:67:

CTCTCTCTCT CTCTCTATA                                                    19

(2) INFORMATION FOR SEQ ID NO:68:

(i) SEQUENCE CHARACTERISTICS:
            (A) LENGTH:  20 base pairs
            (B) TYPE:  nucleic acid
            (C) STRANDEDNESS:  single
            (D) TOPOLOGY:  linear (ii) MOLECULE TYPE:  DNA (genomic)

(xi) SEQUENCE DESCRIPTION:  SEQ ID NO:68:

TATATATGTG TGTGTGTGTG                                       20

(2) INFORMATION FOR SEQ ID NO:69:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:69:

TATATATATA TATGTGTGTG TG                                    22

(2) INFORMATION FOR SEQ ID NO:70:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:70:

TATATATATA TATATATGTG TGTG                                  24

(2) INFORMATION FOR SEQ ID NO:71:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:71:

ACACACACAT ATATATATAT ATAT                                  24

(2) INFORMATION FOR SEQ ID NO:72:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:72:

ACACACACAC ACATATATAT AT                                    22

(2) INFORMATION FOR SEQ ID NO:73:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:73:

ACACACACAC ACACATATAT                                       20

(2) INFORMATION FOR SEQ ID NO:74:

```
       (i) SEQUENCE CHARACTERISTICS:
             (A) LENGTH:  19 base pairs
             (B) TYPE:  nucleic acid
             (C) STRANDEDNESS:  single
             (D) TOPOLOGY:  linear (ii) MOLECULE TYPE:  DNA (genomic)

(xi) SEQUENCE DESCRIPTION:  SEQ ID NO:74:

TGTGTGTGTG TGTGTATAT                                                       19

(2) INFORMATION FOR SEQ ID NO:75:

(i) SEQUENCE CHARACTERISTICS:
             (A) LENGTH:  19 base pairs
             (B) TYPE:  nucleic acid
             (C) STRANDEDNESS:  single
             (D) TOPOLOGY:  linear (ii) MOLECULE TYPE:  DNA (genomic)

(xi) SEQUENCE DESCRIPTION:  SEQ ID NO:75:

GAGAGAGAGA GAGAGATAT                                                       19

(2) INFORMATION FOR SEQ ID NO:76:

(i) SEQUENCE CHARACTERISTICS:
             (A) LENGTH:  18 base pairs
             (B) TYPE:  nucleic acid
             (C) STRANDEDNESS:  single
             (D) TOPOLOGY:  linear (ii) MOLECULE TYPE:  DNA (genomic)

(xi) SEQUENCE DESCRIPTION:  SEQ ID NO:76:

CTCTCTCACA CACACACA                                                        18

(2) INFORMATION FOR SEQ ID NO:77:

(i) SEQUENCE CHARACTERISTICS:
             (A) LENGTH:  18 base pairs
             (B) TYPE:  nucleic acid
             (C) STRANDEDNESS:  single
             (D) TOPOLOGY:  linear (ii) MOLECULE TYPE:  DNA (genomic)

(xi) SEQUENCE DESCRIPTION:  SEQ ID NO:77:

CTCTCTCTCA CACACACA                                                        18

(2) INFORMATION FOR SEQ ID NO:78:

(i) SEQUENCE CHARACTERISTICS:
             (A) LENGTH:  18 base pairs
             (B) TYPE:  nucleic acid
             (C) STRANDEDNESS:  single
             (D) TOPOLOGY:  linear (ii) MOLECULE TYPE:  DNA (genomic)

(xi) SEQUENCE DESCRIPTION:  SEQ ID NO:78:

GTGTGTGTGA GAGAGAGA                                                        18

(2) INFORMATION FOR SEQ ID NO:79:

(i) SEQUENCE CHARACTERISTICS:
             (A) LENGTH:  18 base pairs
             (B) TYPE:  nucleic acid
             (C) STRANDEDNESS:  single
```

(D) TOPOLOGY:  linear (ii) MOLECULE TYPE:  DNA (genomic)

(xi) SEQUENCE DESCRIPTION:  SEQ ID NO:79:

ACACACACAG AGAGAGAG                                                           18

(2) INFORMATION FOR SEQ ID NO:80:

(i) SEQUENCE CHARACTERISTICS:
           (A) LENGTH:  18 base pairs
           (B) TYPE:  nucleic acid
           (C) STRANDEDNESS:  single
           (D) TOPOLOGY:  linear (ii) MOLECULE TYPE:  DNA (genomic)

(xi) SEQUENCE DESCRIPTION:  SEQ ID NO:80:

CTCTCTCTCT GTGTGTGT                                                           18

(2) INFORMATION FOR SEQ ID NO:81:

(i) SEQUENCE CHARACTERISTICS:
           (A) LENGTH:  18 base pairs
           (B) TYPE:  nucleic acid
           (C) STRANDEDNESS:  single
           (D) TOPOLOGY:  linear (ii) MOLECULE TYPE:  DNA (genomic)

(xi) SEQUENCE DESCRIPTION:  SEQ ID NO:81:

AGAGAGAGTG TGTGTGTG                                                           18

(2) INFORMATION FOR SEQ ID NO:82:

(i) SEQUENCE CHARACTERISTICS:
           (A) LENGTH:  20 base pairs
           (B) TYPE:  nucleic acid
           (C) STRANDEDNESS:  single
           (D) TOPOLOGY:  linear (ii) MOLECULE TYPE:  DNA (genomic)

(xi) SEQUENCE DESCRIPTION:  SEQ ID NO:82:

TATATATGTG TGTGTGTGTG                                                         20

(2) INFORMATION FOR SEQ ID NO:83:

(i) SEQUENCE CHARACTERISTICS:
           (A) LENGTH:  22 base pairs
           (B) TYPE:  nucleic acid
           (C) STRANDEDNESS:  single
           (D) TOPOLOGY:  linear (ii) MOLECULE TYPE:  DNA (genomic)

(xi) SEQUENCE DESCRIPTION:  SEQ ID NO:83:

TATATATATA TATGTGTGTG TG                                                      22

(2) INFORMATION FOR SEQ ID NO:84:

(i) SEQUENCE CHARACTERISTICS:
           (A) LENGTH:  22 base pairs
           (B) TYPE:  nucleic acid
           (C) STRANDEDNESS:  single
           (D) TOPOLOGY:  linear (ii) MOLECULE TYPE:  DNA (genomic)

(xi) SEQUENCE DESCRIPTION:  SEQ ID NO:84:

```
TATATATATA TATATATGTG TG                                                    22

(2) INFORMATION FOR SEQ ID NO:85:

(i) SEQUENCE CHARACTERISTICS:
          (A) LENGTH:  43 base pairs
          (B) TYPE:  nucleic acid
          (C) STRANDEDNESS:  single
          (D) TOPOLOGY:  linear (ii) MOLECULE TYPE:  DNA (genomic)

(xi) SEQUENCE DESCRIPTION:  SEQ ID NO:85:

TATATATATA TATATATATA TATGTGTGTG TGTGTGTGTG TGT                             43

(2) INFORMATION FOR SEQ ID NO:86:

(i) SEQUENCE CHARACTERISTICS:
          (A) LENGTH:  43 base pairs
          (B) TYPE:  nucleic acid
          (C) STRANDEDNESS:  single
          (D) TOPOLOGY:  linear (ii) MOLECULE TYPE:  DNA (genomic)

(xi) SEQUENCE DESCRIPTION:  SEQ ID NO:86:

TATATATATA TATATATATA TATCACACAC ACACACACAC ACA                             43

(2) INFORMATION FOR SEQ ID NO:87:

(i) SEQUENCE CHARACTERISTICS:
          (A) LENGTH:  24 base pairs
          (B) TYPE:  nucleic acid
          (C) STRANDEDNESS:  single
          (D) TOPOLOGY:  linear (ii) MOLECULE TYPE:  DNA (genomic)

(xi) SEQUENCE DESCRIPTION:  SEQ ID NO:87:

TATATATATA TATATACACA CACA                                                  24

(2) INFORMATION FOR SEQ ID NO:88:

(i) SEQUENCE CHARACTERISTICS:
          (A) LENGTH:  22 base pairs
          (B) TYPE:  nucleic acid
          (C) STRANDEDNESS:  single
          (D) TOPOLOGY:  linear (ii) MOLECULE TYPE:  DNA (genomic)

(xi) SEQUENCE DESCRIPTION:  SEQ ID NO:88:

TATATATATA CACACACACA CA                                                    22

(2) INFORMATION FOR SEQ ID NO:89:

(i) SEQUENCE CHARACTERISTICS:
          (A) LENGTH:  20 base pairs
          (B) TYPE:  nucleic acid
          (C) STRANDEDNESS:  single
          (D) TOPOLOGY:  linear (ii) MOLECULE TYPE:  DNA (genomic)

(xi) SEQUENCE DESCRIPTION:  SEQ ID NO:89:

TATATACACA CACACACACA                                                       20
```